(12) United States Patent
Punt

(10) Patent No.: US 9,255,284 B2
(45) Date of Patent: *Feb. 9, 2016

(54) CELLULOSE AND LIGNO-CELLULOSE ACTIVE PROTEINS

(71) Applicant: NEDERLANDSE ORGANISATIE VOOR TOEGEPAST-NATUURWETENS CHAPPELIJK ONDERZOEK TNO, Delft (NL)

(72) Inventor: Peter Jan Punt, Houten (NL)

(73) Assignee: NEDERLANDSE ORGANISATIE VOOR TOEGEPAST-NATUURWETENS CHAPPELIJK ONDERZOEK TNO, Delft (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/253,511

(22) Filed: Apr. 15, 2014

(65) Prior Publication Data

US 2014/0315260 A1     Oct. 23, 2014

Related U.S. Application Data

(62) Division of application No. 13/257,255, filed as application No. PCT/NL2010/050138 on Mar. 17, 2010, now Pat. No. 8,735,100.

(30) Foreign Application Priority Data

Mar. 17, 2009   (EP) ..................... 09155380

(51) Int. Cl.
   *C12P 19/00*     (2006.01)
   *C07K 14/00*     (2006.01)
   *C12P 19/14*     (2006.01)
   *C12P 19/02*     (2006.01)

(52) U.S. Cl.
   CPC ................. *C12P 19/14* (2013.01); *C12P 19/02* (2013.01); *C12P 2201/00* (2013.01)

(58) Field of Classification Search
   CPC ............................... C12P 19/00; C07K 14/00
   USPC .......................................................... 435/72
   See application file for complete search history.

(56) References Cited

U.S. PATENT DOCUMENTS

2005/0191736 A1     9/2005    Brown et al.

OTHER PUBLICATIONS

Bayer et al., "The potential of cellulases and cellulosomes for cellulosic waste management," Current Opinion in Biotechnology (2007) 18(3):237-245.
Database UniProt, EBI accession No. B2AVA7 (2008).
Database UniProt, EBI accession No. B2ACZ4 (2008).
GenBank: CAP61309.1, Aug. 21, 2013.
International Search Report for PCT/NL2010/050138, mailed Aug. 11, 2011, 5 pages.

*Primary Examiner* — Maryam Monshipouri
(74) *Attorney, Agent, or Firm* — Morrison & Foerster LLP

(57) ABSTRACT

Methods to digest carbohydrates, especially lignocelluloses and hemicelluloses, using fungal proteins previously not recognized as having this activity are described.

2 Claims, 1 Drawing Sheet

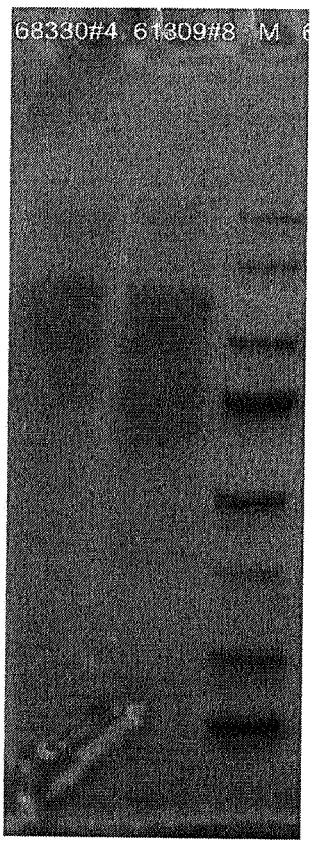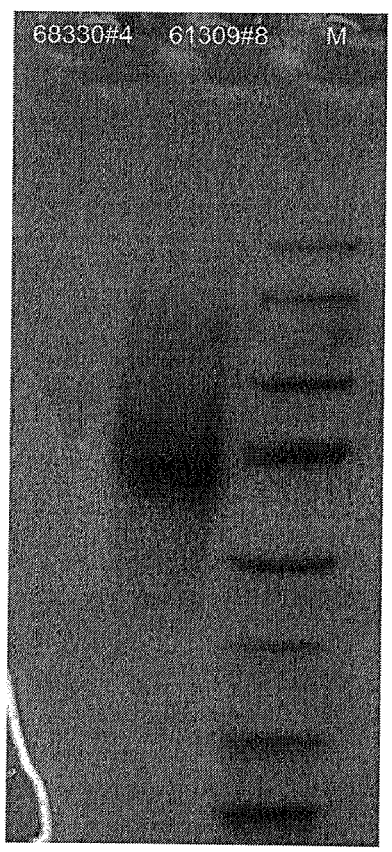

CELLULOSE AND LIGNO-CELLULOSE ACTIVE PROTEINS

CROSS-REFERENCE TO RELATED APPLICATIONS

This application is a divisional of copending U.S. Ser. No. 13/257,255 having an international filing date of 17 Mar. 2010, which is the national phase of PCT application PCT/NL2010/050138 having an international filing date of 17 Mar. 2010, which claims benefit of European application No. 09155380.0 filed 17 Mar. 2009. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 313632012110CorrectedSeqList.txt | Jul. 1, 2014 | 267,079 bytes |

FIELD OF THE INVENTION

This invention is related to the field of enzymatic digest of carbohydrate polymers, more specifically enzymatic modification, conversion and degradation of lignocellulose and (hemi-)cellulose containing substrates.

BACKGROUND ART

Carbohydrates constitute the most abundant organic compounds on earth. However, much of this carbohydrate is sequestered in complex polymers including starch (the principle storage carbohydrate in seeds and grain), and a collection of carbohydrates and lignin known as lignocellulose. The main carbohydrate components of lignocellulose are cellulose, hemicellulose, and glucans. These complex polymers are often referred to collectively as lignocellulose. Cellulose is a linear polysaccharide composed of glucose residues linked by beta-1,4 bonds. The linear nature of the cellulose fibers, as well as the stoichiometry of the beta-linked glucose (relative to alpha) generates structures more prone to interstrand hydrogen bonding than the highly branched alpha-linked structures of starch. Thus, cellulose polymers are generally less soluble, and form more tightly bound fibers than the fibers found in starch. Hemicellulose is a complex polymer, and its composition often varies widely from organism to organism, and from one tissue type to another. In general, a main component of hemicellulose is beta-1,4-linked xylose, a five carbon sugar. However, this xylose is often branched as beta-1,3 linkages, and can be substituted with linkages to arabinose, galactose, mannose, glucuronic acid, or by esterification to acetic acid. Hemicellulose can also contain glucan, which is a general term for beta-linked six carbon sugars. The composition, nature of substitution, and degree of branching of hemicellulose is very different in dicot plants as compared to monocot plants. In dicots, hemicellulose is comprised mainly of xyloglucans that are 1,4-beta-linked glucose chains with 1,6-beta-linked xylosyl side chains. In monocots, including most grain crops, the principle components of hemicellulose are heteroxylans. These are primarily comprised of 1,4-beta-linked xylose backbone polymers with 1,3-beta linkages to arabinose, galactose and mannose as well as xylose modified by ester-linked acetic acids. Also present are branched beta glucans comprised of 1,3- and 1,4-beta-linked glucosyl chains. In monocots, cellulose, heteroxylans and beta glucans are present in roughly equal amounts, each comprising about 15-25% of the dry matter of cell walls.

The sequestration of such large amounts of carbohydrates in plant biomass provides a plentiful source of potential energy in the form of sugars, both five carbon and six carbon sugars that could be utilized for numerous industrial and agricultural processes. However, the enormous energy potential of these carbohydrates is currently under-utilized because the sugars are locked in complex polymers, and hence are not readily accessible for fermentation. Methods that generate sugars from plant biomass would provide plentiful, economically-competitive feedstocks for fermentation into chemicals, plastics, and fuels. Current processes to generate soluble sugars from lignocellulose are complex. A key step in the process is referred to as pretreatment. The aim of pretreatment is to increase the accessibility of cellulose to cellulose-degrading enzymes, such as the cellulase mixture derived from fermentation of the fungus *Trichoderma reesei*. Current pretreatment processes involve steeping lignocellulosic material such as corn stover in strong acids or bases under high temperatures and pressures. Such chemical pretreatments degrade hemicellulose and/or lignin components of lignocellulose to expose cellulose, but also create unwanted by-products such as acetic acid, furfural, hydroxymethyl furfural and gypsum. These products must be removed in additional processes to allow subsequent degradation of cellulose with enzymes or by a co-fermentation process known as simultaneous saccharification and fermentation (SSF). The conditions currently used for chemical pretreatments require expensive reaction vessels, and are energy intensive. Chemical pretreatment occurring at high temperatures and extreme pH conditions (for example 160° C. and 1.1% sulfuric acid at 12 atm. pressure) are not compatible with known cellulose-degrading enzymes. Further, these reactions produce compounds that must be removed before fermentation can proceed. As a result, chemical pretreatment processes currently occur in separate reaction vessels from cellulose degradation, and must occur prior to cellulose degradation.

Thus, methods that are more compatible with the cellulose degradation process, do not require high temperatures and pressures, do not generate toxic waste products, and require less energy, are desirable. For these reasons, efficient methods are needed for biomass conversion.

Filamentous fungi are efficient producers of a large variety of enzymes, and, therefore, they are exploited already for decades for the production of enzymes at industrial scale. Numerous hydrolytic activities have been identified for hydrolysis of starch, (hemi)cellulose and inulin. For many of these enzymes industrial processes have been developed.

Based on extensive research on these carbohydrolytic enzymes, besides catalytic domains also domains involved in substrate binding have been identified. For fungal enzymes in particular, most of the lignocellulose and (hemi-)cellulose degrading enzymes are characterized by having a cellulose binding domain, denominated as CBM1 (see also www.cazy.org/fam/acc_CBM.html. Interestingly, in particular for CBM1, which is unique to fungi, proteins with completely different catalytic activities have been identified. Besides different types of (hemi)cellulases, xylanases, pectinases, esterases, chitinases and lipases amongst others also CBM-1 proteins with unknown activity have been identified. The largest gene family of this latter class is the GH61 protein/gene family. However, there is still need for further enzymes involved in lignocellulose and (hemi-)cellulose degradation.

SUMMARY OF THE INVENTION

The inventors have now discovered two novel gene families of lignocellulose active enzymes, sharing a hitherto unknown domain (sometimes in addition to a CBM1 domain). Therefore the invention comprises a lignocellulose and/or (hemi-)cellulose active protein comprising the domain with the amino acid sequence (SEQ ID NOS: 1-2)
[DN]-P-[IVL]-[MAIV]-X-[PAF]-[GNQ]-$X_{3-4}$-[SAP]-$X_{1-2}$-

H-X-H-$X_3$-G-$X_{16-21}$-C-[ST]-[ST]-$X_5$-D-X-S-[AN]-Y-[YW]-

X-[AP]-X-[LVM]-$X_{2-9}$-G or a sequence that has an identity of more than 70%, preferably more than 75%, more preferably more than 80%, more preferably more than 85%, more preferably more than 90%, more preferably more than 95%, more preferably more than 98% with said amino acid sequence. Preferably said protein comprises the sequence DPLVFPGAM QSPHVHQIVG GNMFNVTMDP NRHNIGEEAT CTTCTFSEDF SNYW-TAILYF RARNGTLIRV PQRPNIDFDG ARGGGMTVYY TATYQNHKPT AFQPGFRMIV GNPMYRTQAE ASRYRQMTFT CLETLSTRTG ETTEMPKQPC REGIM-SNVRF PTCWDGKTLD PPDHSSHVAY PSSGTFESGG PCPASHPVRI PQLFYEVLWD TRRFNDRSLW PEDG-SQPFVW SYGDYTGYGT HGDYVFGWKG I, (SEQ ID NO:4) or, alternatively, the sequence GAPSVHAVLR FSC-SELVTER LDPLVFPGAM QSPHVHQIVG GNMFNVT-MDP NRHNIGEEAT CTTCTFSEDF SNYWTAILYF RARNGTLIRV PQRPNIDFDG ARGGGMTVYY TATYQNHKPT AFQPGFRMIV GNPMYRTQAE ASRYRQMTFT CLETLSTRTG ETTEMPKQPC REGIM-SNVRF PTCWDGKTLD PPDHSSHVAY PSSGTFESGG PCPASHPVRI PQLFYEVLWD TRRFNDRSLW PEDG-SQPFVW SYGDYTGYGT HGDYVFGWKG DSLQRAM-DAN CDFYCPQLKT QSIATGNQCR QNQKVAENID1 GPFDRLPGNV EITGPQPGAS (SEQ ID NO:5) or a sequence that has an identity of more than 70%, preferably more than 75%, more preferably more than 80%, more preferably more than 85%, more preferably more than 90%, more preferably more than 95%, more preferably more than 98% with said amino acid sequences. Said protein is preferably selected from the group consisting of the proteins with the NCBI accession no. XP_001907658.1 (SEQ ID NO:16), XP_001904981.1 (SEQ ID NO:17), XP_001911253.1 (SEQ ID NO:18), XP_001911467.1 (SEQ ID NO:19), XP_001908261.1 (SEQ ID NO:20), XP_001907671.1 (SEQ ID NO:21), XP_001906312.1 (SEQ ID NO:22), XP_001912166.1 (SEQ ID NO:23), XP_001904033.1 (SEQ ID NO:24), XP_001905336.1 (SEQ ID NO:25), XP_001904002.1 (SEQ ID NO:26), XP_001905175.1 (SEQ ID NO:27), XP_001911617.1 (SEQ ID NO:28), XP_001907672.1 (SEQ ID NO:29), XP_001903756.1 (SEQ ID NO:30), XP_001903833.1 (SEQ ID NO:31), XP_001904389.1 (SEQ ID NO:32), XP_001904303.1 (SEQ ID NO:33), XP_001903094.1 (SEQ ID NO:34), XP_001904583.1 (SEQ ID NO:35), XP_001904957.1 (SEQ ID NO:36), XP_001906851.1 (SEQ ID NO:37), XP_001903754.1 (SEQ ID NO:38), XP_001911708.1 (SEQ ID NO:39), XP_001907931.1 (SEQ ID NO:40), and XP_001903118.1 (SEQ ID NO:41) from *Podospora anserina*, BAE61525.1 (SEQ ID NO:42), BAE54784.1 (SEQ ID NO:43) and BAE66576.1 (SEQ ID NO:44) from *Aspergillus oryzae*, CAK38435.1 (SEQ ID NO:45) and CAK40357.1 (SEQ ID NO:46) from *Aspergillus niger* and three proteins from *Trichoderma reesei* (proteins 108655 (SEQ ID NO:47), 37665 (SEQ ID NO:48) and 102735 (SEQ ID NO:49) from the *T. reesei* protein database at JTI, genome.jgi-psf.org/Trire2/Trire2.home.html). Also preferred is a protein according to the invention that additionally comprises a CBM1 domain, preferably wherein said CBM1 domain comprises the consensus sequence C-$G_{(2)}$-$X_{(4-7)}$-G-$X_{(3)}$-C-$X_{(4,5)}$-C-$X_{(3-5)}$-[NHGS]-X-[FYWMI]-$X_{(2)}$-Q-C (SEQ ID NO:9), more preferably wherein said protein is the protein from *Podospora anserina* with the NCBI accession no. CAP68330.1 (SEQ ID NO:81).

In another embodiment, the invention comprises a lignocellulose and/or (hemi-)cellulose active protein comprising the domain with the amino acid sequence [GA]-[ST]-[IV]-[ILV]-W-[DS]-G-[RIFS]-F-[ND]-[DS]-$X_2$-[TS]-$X_2$-D-[LIF]-[ND]-K-W-S-W-[GSA]-N-Q-[IV]-[GP]-[PS]-[YW]-$X_{0-4}$-Q-[YW]-Y-I-H-G-S-$X_2$-[VT]-$X_2$-Y-[ILV]-X[ILV]-S-$X_2$-[FY]-K-N-P-$X_{5-7}$-Q-G-X-[KR]-I-T-[LI]-D-X-[ST]-[AS]-X-W-N-G-Q-[NT]-M-X-R-[IST]-E-L-I-P-Q-T-$X_{6-13}$-G-X-[KLV]-[FY]-Y-H-F-S-[ILV]-$X_5$-N-A-P-$X_4$-E-H-Q-[ILV]-[AC]-F-F-E-$X_{0-13}$-S-H-F-T-E-[LM]-K-[YST]-G-W-$X_{0-2}$-G-$X_{6-33}$-[LF]-$X_{1-24}$-I-D-F-[ASD]-$X_{3-8}$-V-[FL]-[FWY]-X-S-[ENT]-G-$X_{2-5}$-[AP]-L-$X_{2-4}$-[AV]-[AV]-X-[PAN]-$X_{3-5}$-[ANS]-[AT]-[AFS]-[ST]-[DN]-[GS]-[AQ]-D-[FW]-H-{FILV}-G-[EIQV]-L-[ERK]-[ILV]-P-$X_{8-18}$-E-D-[FWY]-[FY]-[FW]-S-G-[IV]-[FY]-[IV]-E (SEQ ID NOS:6-7) or a sequence that has an identity of more than 70%, preferably more than 75%, more preferably more than 80%, more preferably more than 85%, more preferably more than 90%, more preferably more than 95%, more preferably more than 98% with said amino acid sequence. Preferably such a protein comprises the sequence GT ILWDGRFNDM TSSADLNKWS WGNQVGPYQY YIHGSSPVSA YVNL-SPDYKN PADTGSRQGA KITLDNTAYW NGQNMRR-TEL IPQTTAAINQ GKVYYHFSLM RKDINAPATT REH-QIAFFES HFTELKSGWL SGAPGISDTL LRWCIDFAAG TVGFWHSTGS DPLTRKVAPV KTSTSSNGAD WHVGVLELPR SGYPDSNEDF YWSGVYIESG SLTTS-VAGPG QPIPGDGG (SEQ ID NO:3) or a sequence that has an identity of more than 70%, preferably more than 75%, more preferably more than 80%, more preferably more than 85%, more preferably more than 90%, more preferably more than 95%, more preferably more than 98% with said amino acid sequence. Preferably said protein is selected from the group consisting of the proteins from *Podospora anserina* with the NCBI accession numbers XP_001903534.1 (CAP61309.1) (SEQ ID NO:50) and XP_001907960.1 (CAP68633.1) (SEQ ID NO:51), from *Aspergillus flavus* (EED52126.1 (SEQ ID NO:52) and EED54304.1 (SEQ ID NO:53)), from *Aspergillus fumigatus* (XP_751054.2 (SEQ ID NO:54), XP_755877.1 (SEQ ID NO:55) and EDP49742.1 (SEQ ID NO:56)), *Aspergillus clavatus* (XP_001275827.1) (SEQ ID NO:57), *Aspergillus oryzae* (XP_001825707.1) (SEQ ID NO:58), *Aspergillus terreus* (XP_001211584.1) (SEQ ID NO:59), *Aspergillus nidulans* (XP_680867.1) (SEQ ID NO:60), *Aspergillus niger* (XP_001392581.1) (SEQ ID NO:61), *Magnaporthe griseae* (XP_362641.1 (SEQ ID NO:62) and XP_001408874.1 (SEQ ID NO:63)), *Phaeosphaeria nodorum* (XP_001793212.1 (SEQ ID NO:64) and XP_001799980.1 (SEQ ID NO:65)), *Neurospra crassa* (XP_958348.1 (SEQ ID NO:66) and XP_956768.1 (SEQ ID NO:67)), *Pyrenophora tritici-repentis* (XP_001932168.1 (SEQ ID NO:68) and XP_001931381.1 (SEQ ID NO:69)), *Neosartorya fischeri* (XP_001258287.1 (SEQ ID NO:70) and XP_001261005.1 (SEQ ID NO:71)), *Chaetomiun globosum* (XP_001228503) (SEQ ID NO:72), *Botryotinia fuckeliana* (XP_001546653.1) (SEQ ID NO:73), *Sclerotinia sclerotiorum* (XP_001593519.1) (SEQ ID NO:74), *Moniliophthora perniciosa* (EEB91913.1) (SEQ ID NO:75) and *Coprionopsis cinerea* (XP_001835742) (SEQ ID NO:76).

In another embodiment, said protein additionally comprises a CBM1 domain, and is preferably selected from the group consisting of the proteins with NCBI accession no. CAP61309.1 (SEQ ID NO:77), BAE64574.1 (SEQ ID NO:78) and CAK45436.1 (SEQ ID NO:79).

In a preferred embodiment the protein from the invention is from fungal origin, preferably wherein the fungus is chosen from the group consisting of *Aspergillus, Neurospora, Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus, Trichoderma Penicillium* and *Chrysosporium*.

Also part of the invention is a nucleic acid encoding a protein according to the invention, a vector comprising said nucleic acid and a host cell capable of expressing a protein according to the invention by harbouring said nucleic acid or vector.

Further, also comprised in the invention is the use of a protein according to the invention in the modification of a raw carbohydrate, preferably lignocellulose and/or (hemi-)cellulose, most preferably non-soluble cellulose, preferably wherein the protein has or enhances cellulase activity.

LEGENDS TO THE FIGURES

FIG. 1. SDS PAGE of proteins produced by *A. niger* transformants transgenic for CAP68330 and CAP61309. M indicates marker lane.

DETAILED DESCRIPTION

The term "sequence identity," as used herein, is generally expressed as a percentage and refers to the percent of amino acid residues or nucleotides, as appropriate, that are identical as between two sequences when optimally aligned. For the purposes of this invention, sequence identity means the sequence identity determined using the well-known Basic Local Alignment Search Tool (BLAST), which is publicly available through the National Cancer Institute/National Institutes of Health (Bethesda, Md.) and has been described in printed publications (see, e.g., Altschul et al., J. Mol. Biol, 215(3), 403-10 (1990)). Preferred parameters for amino acid sequences comparison using BLASTP are gap open 11.0, gap extend 1, Blosum 62 matrix. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

The term "signal peptide" or "signal sequence" as used herein, refers to an amino acid sequence, typically located at the amino terminus of an immature protein or polypeptide (e.g., prior to secretion from a cell and associated processing and cleavage), which directs the secretion of the protein or polypeptide from the cell in which it is produced. The signal peptide typically is removed from an immature protein or polypeptide prior to or during secretion and, thus, is not present in the mature, secreted polypeptide.

As used herein, the term "recombinant nucleic acid molecule" refers to a recombinant DNA molecule or a recombinant RNA molecule. A recombinant nucleic acid molecule is any synthetic nucleic acid construct or nucleic acid molecule containing joined nucleic acid molecules from different original sources or and not naturally occurring or attached together and prepared by using recombinant DNA techniques.

The term "recombinant host cell" as used herein, refers to a host cell strain containing nucleic acid not naturally occurring in that strain and which has been introduced into that strain using recombinant DNA techniques.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" (a polymeric form of nucleotides, either ribonucleotides or deoxyribonucleotides, double- or single-stranded of any length) as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refer to those nucleic acids which encode identical or conservatively modified variants of the amino acid sequences due to the degeneracy of the genetic code.

The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The term "gene", as used herein, refers to a nucleic acid sequence containing a template for a nucleic acid polymerase, in eukaryotes, RNA polymerase II. Genes are transcribed into mRNAs that are then translated into protein.

"Expression" refers to the transcription of a gene into structural RNA (rRNA, tRNA) or messenger RNA (mRNA) with subsequent translation into a protein.

The term "complementary", as used herein, refers to a sequence of nucleotides which forms a hydrogen-bonded duplex with another sequence of nucleotides according to Watson-Crick base-paring rules. For example, the complementary base sequence for 5'-AAGGCT-3' is 3'-TTCCGA-5'. As used herein, "substantially complementary" means that two nucleic acid sequences have at least about 40, preferably about 50% more preferably at least 55%, more preferably about 60%, more preferably about 70%, more preferably about 80%, even more preferably 90%, and most preferably about 98%, sequence complementarity to each other.

The term "hybridise" refers to the process by which single strands of nucleic acid sequences form double-helical segments through hydrogen bonding between complementary nucleotides.

As used herein, the term "expression control sequence" refers to a nucleic acid sequence that regulates the transcription and translation of a gene to which it is operatively linked. An expression control sequence is "operatively linked" to a gene when the expression control sequence controls and regulates the transcription and, where appropriate, translation of the gene. The term "operatively linked" includes the provision of an appropriate start codon (e.g. ATG), in front of a polypeptide-encoding gene and maintaining the correct reading frame of that gene to permit proper translation of the mRNA.

As used herein, the term "operably linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e., operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleotide sequence that comprises in the 5' to 3' direction and operably linked: (a) a fungal-recognized transcription and translation initiation region, (b) a coding sequence for a polypeptide of interest, and (c) a fungal-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e., operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the host cell, but which has a replicon which is nonfunctional in that organism. Integration of the segment comprising the gene of interest may be selected if an appropriate marker is included within that segment.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

By "host cell" is meant a cell which contains a vector or recombinant nucleic acid molecule and supports the replication and/or expression of the vector or recombinant nucleic acid molecule. Host cells may be prokaryotic cells such as *E. coli*, or eukaryotic cells such as yeast, fungus, plant, insect, amphibian, or mammalian cells. Preferably, host cells are fungal cells.

The term "fungus" or "fungi" includes a wide variety of nucleated, spore-bearing organisms which are devoid of chlorophyll. Examples of fungi include yeasts, mildews, molds, rusts and mushrooms. Preferred fungi in aspects of the present invention are organisms of the genera *Aspergillus, Neurospora, Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus Penicillium* and *Chrysospsorium*.

The terms "isolated" or "purified" as used herein refer to a nucleic acid or protein or peptide that is removed from at least one component with which it is naturally associated. In the present invention, an isolated nucleic acid can include a vector comprising the nucleic acid. Purified as used herein to describe a polypeptide produced by cultivation of a recombinant host cell refers to removing that polypeptide from at least one component with which it is naturally associated in the host cell or culture medium.

The CBM1 domain that is present in many of the proteins that are held to have activity on cellulose, chitin, sepharose, xylan has a consensus amino acid sequence that can be denoted as:

(SEQ ID NO: 9)
C-G$_{(2)}$-X$_{(4-7)}$-G-X$_{(3)}$-C-X$_{(4-5)}$-C-X$_{(3-5)}$-[NHGS]-X-
[FYWMI]-X$_{(2)}$-Q-C in which the amino acids between square brackets are alternatives on that position, and X$_n$ denotes a series of n freely chosen amino acids. Alternatively, the CBM1 domain is a sequence that has a high identity with the above consensus sequence. However, no or only very limited catalytic activity has been shown to reside in or be linked to said CBM1 domain.

Now, the inventors have discovered two novel classes of starch active proteins wherein the first class shares a common domain of unknown function (D-U-F), also called the DUF1996 domain, partly represented by the consensus sequence:

(SEQ ID NOS: 1-2)
[DN]-P-[IVL]-[MAIV]-x-[PAF]-[GNQ]-X$_{3-4}$-[SAP]-X$_{1-2}$-

H-X-H-X$_3$-G-X$_{16-21}$-C-[ST]-[ST]-X$_5$-D-X-S-[AN]-Y-[YW]-

X-[AP]-X-[LVM]-X$_{2-9}$-G in which the amino acids between square brackets are alternatives at the same position and X$_n$ denotes a series of n freely chosen amino acids, or an amino acid sequence that has a high degree of identity with said consensus sequence.

An example of such a domain is the sequence:

(SEQ ID NO: 4)
DPLVFPGAM QSPHVHQIVG GNMFNVTMDP NRHNIGEEAT

CTTCTFSEDF SNYWTAILYF RARNGTLIRV PQRPNIDFDG

ARGGGMTVYY TATYQNHKPT AFQPGFRMIV GNPMYRTQAE

ASRYRQMTFT CLETLSTRTG ETTEMPKQPC REGIMSNVRF

PTCWDGKTLD PPDHSSHVAY PSSGTFESGG PCPASHPVRI

PQLFYEVLWD TRRFNDRSLW PEDGSQPFVW SYGDYTGYGT

HGDYVFGWKG I, and also the sequence:

(SEQ ID NO: 5)
GAPSVHAVLR FSCSELVTER LDPLVFPGAM QSPHVHQIVG

GNMFNVTMDP NRHNIGEEAT CTTCTFSEDF SNYWTAILYF

RARNGTLIRV PQRPNIDFDG ARGGGMTVYY TATYQNHKPT

AFQPGFRMIV GNPMYRTQAE ASRYRQMTFT CLETLSTRTG

ETTEMPKQPC REGIMSNVRF PTCWDGKTLD PPDHSSHVAY

PSSGTFESGG PCPASHPVRI PQLFYEVLWD TRRFNDRSLW

PEDGSQPFVW SYGDYTGYGT HGDYVFGWKG DSLQRAMDAN

CDFYCPQLKT QSIATGNQCR QNQKVAENID1 GPFDRLPGNV

EITGPQPGAS or an amino acid sequence that has a high degree of identity with said sequences. A high degree of identity is herein defined as an identity of more than 70%, preferably more than 75%, more preferably more than 80%, more preferably more than 85%, more preferably more than 90%, more preferably more than 95%, more preferably more than 98%. Species of proteins with this new domain are 26 proteins from *Podospora anserina* (accession numbers XP_001907658.1 (SEQ ID NO:16), XP_001904981.1 (SEQ ID NO:17), XP_001911253.1, (SEQ ID NO:18) XP_001911467.1 (SEQ ID NO:19), XP_001908261.1 (SEQ ID NO:20), XP_001907671.1 (SEQ ID NO:21), XP_001906312.1 (SEQ ID NO:22), XP_001912166.1 (SEQ ID NO:23), XP_001904033.1 (SEQ ID NO:24), XP_001905336.1 (SEQ ID NO:25), XP_001904002.1 (SEQ ID NO:26), XP_001905175.1 (SEQ ID NO:27), XP_001911617.1 (SEQ ID NO:28), XP_001907672.1 (SEQ ID NO:29), XP_001903756.1 (SEQ ID NO:30), XP_001903833.1 (SEQ ID NO:31), XP_001904389.1 (SEQ ID NO:32), XP_001904303.1 (SEQ ID NO:33), XP_001903094.1 (SEQ ID NO:34), XP_001904583.1 (SEQ ID NO:35), XP_001904957.1 (SEQ ID NO:36), XP_001906851.1 (SEQ ID NO:37), XP_001903754.1 (SEQ ID NO:38), XP_001911708.1 (SEQ ID NO:39), XP_001907931.1 (SEQ ID NO:40), XP_001903118.1 (SEQ ID NO:41), BAE61525.1 (SEQ ID NO:42), BAE54784.1 (SEQ ID NO:43) and BAE66576.1 (SEQ ID NO:44) from *Aspergillus oryzae*, CAK38435.1 (SEQ ID NO:45) and CAK40357.1 (SEQ ID NO:46) from *Aspergillus niger* and three proteins from *Trichoderma reesei* (proteins 108655 (SEQ ID NO:47), 37665 (SEQ ID NO:48) and 102735 (SEQ ID NO:49) from the *T. reesei* protein database at JTI, genome.jgi-psf.org/Trire2/Trire2.home.html, see Martinez, D. et al., 2008, *Nature Biotechnology* 26, 553-560).

This new class of proteins has been discovered in the search for proteins with CBM1 domains. It appeared that several of the proteins, especially those from fungal origin contained the above conserved DUF1996 domain next to the CBM1 domain. Further search for more proteins that also comprised the conserved DUF1996 domain has led to the proteins of the present invention. It is submitted that for all currently known proteins with said domain that are listed above and/or in the experimental part no function was hitherto known from any of these proteins. A species of a protein with both CBM1 and DUF1996 domains is CAP68330.1 from *Podospora anserine* (SEQ ID NO:81).

A further new class of proteins concerns proteins that have the domain with the consensus sequence: [GA]-[ST]-[IV]-[ILV]-W-[DS]-G-[RIFS]-F-[ND]-[DS]-X$_2$-[TS]-X$_2$-D-[LIF]-[ND]-K-W-S-W-[GSA]-N-Q-[IV]-[GP]-[PS]-[YW]-X$_{0-4}$-Q-[YW]-Y-I-H-G-S-X$_2$-[VT]-X$_2$-Y-[ILV]-X[ILV]-S-X$_2$-[FY]-K-N-P-X$_{5-7}$-Q-G-X-[KR]-I-T-[LI]-D-X-[ST]-[AS]-X-W-N-G-Q-[NT]-M-X-R-[IST]-E-L-I-P-Q-T-X$_{6-13}$-G-X-[KLV]-[FY]-Y-H-F-S-[ILV]-X$_5$-N-A-P-X$_4$-E-H-Q-[ILV]-[AC]-F-F-E-X$_{0-13}$-S-H-F-T-E-[LM]-K-[YST]-G-W-X$_{0-2}$-G-X$_{6-33}$-[LF]-X$_{1-24}$-I-D-F-[ASD]-X$_{3-8}$-V-[FL]-[FWY]-X-S-[ENT]-G-X$_{2-5}$-[AP]-L-X$_{2-4}$-[AV]-[AV]-X-[PAN]-X$_{3-5}$-[ANS]-[AT]-[AFS]-[ST]-[DN]-[GS]-[AQ]-D-[FW]-H-{FILV}-G-[EIQV]-L-[ERK]-[ILV]-P-X$_{8-18}$-E-D-[FWY]-[FY]-[FW]-S-G-[IV]-[FY]-[IV]-E (SEQ ID NOS:6-7) or an amino acid sequence that has a high degree of identity with this sequence. Particularly, the domain comprises the sequence GT ILWDGRFNDM TSSADLNKWS WGNQVG-PYQY YIHGSSPVSA YVNLSPDYKN PADTGSRQGA KITLDNTAYW NGQNMRRTEL IPQTTAAINQ GKVYY-HFSLM RKDINAPATT REHQIAFFES HFTELKSGWL SGAPGISDTL LRWCIDFAAG TVGFWHSTGS DPL-TRKVAPV KTSTSSNGAD WHVGVLELPR SGYPD-SNEDF YWSGVYIESG SLTTSVAGPG QPIPGDGG (SEQ ID NO:3) or an amino acid sequence that has a high degree of identity therewith. A high degree of identity is herein defined as an identity of more than 70%, preferably more than 75%, more preferably more than 80%, more preferably more than 85%, more preferably more than 90%, more preferably more than 95%, more preferably more than 98%. Species of a protein with this new domain are two proteins from *Podospora anserina* with accession numbers XP_001903534.1 (CAP61309.1) and XP_001907960.1 (CAP68633.1), wherein CAP61309 comprises the sequence (SEQ ID NO: 10)
19  GTILWDGRFNDMTSSADLNKWSWGNQVGPYQYYIHGSSP
    VSAYVNLSPDYKNPADTGSRQ

79  GAKITLDNTAYWNGQNMRRTELIPQTTAAINQGKVYYHF
    SLMRKDINAPATTREHQIAFF

```
139   ESHFTELKSGWLSGAPGISDTLLRWCIDFAAGTVGFWHS
      TGSDPLTRKVAPVKTSTSSNG

199   ADWHVGVLELPRSGYPDSNEDFYWSGVYIESGSLTTSVA    248
      GPGQPIPGDGG
``` and CAP68633 comprises the sequence

```
                                        (SEQ ID NO: 11)
 19   GAVLWDGRFNDFTSSADLNKWSWANQVGPYPFTNKEYY
      IHGSGTVNRYINLSPDYKNPND

79   TVSKQGARFTLDSTAYWNGQTMRRIELIPQTKAAINRG
      KVFYHFSISRRDTNAPSVNKEH

139   QICFFESHFTELKYGWISGEQGAANPALQWMTNQRTQW
      KLSEWKANVWHNFAYEIDFSGN

199   RVGLWYSEGGADLKQVVAPVGGVSTSSNGQDWHLGVLE
      LPRSGYPNTNEDYYFSGVFIED

259   GAITTKIGGPGE                              270
```

Other examples of this new class of proteins are hitherto hypothetical proteins with unknown function from *Aspergillus flavus* (EED52126.1 (SEQ ID NO:52) and EED54304.1 (SEQ ID NO:53)), from *Aspergillus fumigatus* (XP_751054.2 (SEQ ID NO:54), XP_755877.1 (SEQ ID NO:55) and EDP49742.1 (SEQ ID NO:56)), *Aspergillus clavatus* (XP_001275827.1) (SEQ ID NO:57), *Aspergillus oryzae* (XP_001825707.1) (SEQ ID NO:58), *Aspergillus terreus* (XP_001211584.1) (SEQ ID NO:59), *Aspergillus nidulans* (XP_680867.1) (SEQ ID NO:60), *Aspergillus niger* (XP_001392581.1) (SEQ ID NO:61), *Magnaporthe griseae* (XP_362641.1 (SEQ ID NO:62) and XP_001408874.1 (SEQ ID NO:63)), *Phaeosphaeria nodorum* (XP_001793212.1 (SEQ ID NO:64) and XP_001799980.1 (SEQ ID NO:65)), *Neurospra crassa* (XP_958348.1 (SEQ ID NO:66) and XP_956768.1 (SEQ ID NO:67)), *Pyrenophora tritici-repentis* (XP_001932168.1 (SEQ ID NO:68) and XP_001931381.1 (SEQ ID NO:69)), *Neosartorya fischeri* (XP_001258287.1 (SEQ ID NO:70) and XP_001261005.1 (SEQ ID NO:71)), *Chaetomiun globosum* (XP_001228503) (SEQ ID NO:72), *Botryotinia fuckeliana* (XP_001546653.1) (SEQ ID NO:73), *Sclerotinia sclerotiorum* (XP_001593519.1) (SEQ ID NO:74), *Moniliophthora perniciosa* (EEB91913.1) (SEQ ID NO:75) and *Coprionopsis cinerea* (XP_001835742) (SEQ ID NO:76).

This second new class of proteins has also been discovered in the search of proteins with CBM1 domains. It appeared that several of the proteins, especially those from fungal origin contained the above conserved new domain next to the CBM1 domain. Further search for more proteins that also comprised the conserved new domain has led to the proteins of the present invention. It is submitted that all currently known proteins with said domain or a domain which is highly identical thereto are listed in the experimental part and that no function was hitherto known from any of these proteins. Species of the proteins with both domains are CAP61309.1 (SEQ ID NO:77) from *Podospora anserina*, BAE64574.1 (SEQ ID NO:78) from *Aspergillus oryzae*, CAK45436.1 (SEQ ID NO:79) from *Aspergillus niger* and AN7598.2 from *Aspergillus nidulans* (SEQ ID NO:80).

The proteins of the invention are generally derived from fungi.

Also part of the invention is a nucleotide sequence encoding one or more of the lignocellulose or (hemi-)cellulose active proteins described above. Such a nucleotide sequence can be any nucleotide sequence that encodes said protein(s), but preferably it is the natural coding sequence found in the organisms from which the lignocellulose or (hemi-)cellulose active proteins are derived. However, if these nucleotide sequences are meant for expression in a different host organism, the nucleotide sequence(s) may be adapted to optimize expression is said host organism (codon optimization). For expression purposes, the nucleotide sequence is included in an expression vector that also provides for regulatory sequences, operably linked with the coding nucleotide sequence.

The proteins of the invention can be used in isolated form for addition to a raw carbohydrate (lignocellulose or (hemi-)cellulose) substrate, alone or together with other lignocellulose or (hemi-)cellulose degrading enzymes, such as (hemi) cellulase, xylanase and/or pectinase. The proteins of the invention may yield a lignocellulose or (hemi-)cellulose hydrolytic activity per se, or they increase the accessibility of the lignocellulose or (hemi-)cellulose by other lignocellulose or (hemi-)cellulose degrading enzymes.

In another embodiment, the proteins of the invention can be (over)expressed in a host cell. Overexpression of the proteins of the present invention can be effected in several ways. It can be caused by transforming a host cell with a gene coding for a protein of the invention. Alternatively, another method for effecting overexpression is to provide a stronger promoter in front of and regulating the expression of said gene. This can be achieved by use of a strong heterologous promoter or by providing mutations in the endogenous promoter. An increased expression of the protein can also be caused by removing possible inhibiting regulatory proteins, e.g. that inhibit the expression of such proteins. The person skilled in the art will know other ways of increasing the activity of the above mentioned starch active proteins.

In another aspect of the invention, host cells overexpressing at least one of the above mentioned nucleotide sequences, encoding at least one lignocellulose or (hemi-)cellulose active protein of the invention, are produced and used, for production of said protein(s).

Host cells used in the invention are preferably cells of filamentous fungi, yeasts and/or bacteria, such as, but not limited to, *Aspergillus* sp., such as the fungi *A. terreus*, *A. itaconicus* and *A. niger*, *Aspergillus nidulans*, *Aspergillus oryzae* or *Aspergillus fuminagates*, *Trichoderma*, *Penicillium Chrysosporium*, *Ustilago zeae*, *Ustilago maydis*, *Ustilago* sp., *Candida* sp., *Yarrowia lipolytica*, *Rhodotorula* sp. and *Pseudozyma antarctica*, the bacterium *E. coli* and the yeast *Saccharomyces cerevisiae*. Especially preferred are host cells that also produce one or more lignocellulose degrading enzymes, such as (hemi)cellulase, xylanase or pectinase.

Recombinant host cells described above can be obtained using methods known in the art for providing cells with recombinant nucleic acids. These include transformation, transconjugation, transfection or electroporation of a host cell with a suitable plasmid (also referred to as vector) comprising the nucleic acid construct of interest operationally coupled to a promoter sequence to drive expression. Host cells of the invention are preferably transformed with a nucleic acid construct as further defined below and may comprise a single but preferably comprises multiple copies of the nucleic acid construct. The nucleic acid construct may be maintained episomally and thus comprise a sequence for autonomous replication, such as an ARS sequence. Suitable episomal nucleic acid constructs may e.g. be based on the yeast 2μ or pKD1 (Fleer et al., 1991, Biotechnology 9: 968-975) plasmids. Preferably, however, the nucleic acid construct is integrated in one or more copies into the genome of the host cell. Integration into the host cell's genome may occur at random by illegitimate recombination but preferably the nucleic acid construct is integrated into the host cell's genome by homologous recombination as is well known in the art of fungal molecular genetics (see e.g. WO 90/14423, EP-A-0 481 008, EP-A-0 635 574 and U.S. Pat. No. 6,265,186). Most preferably for homologous recombination the ku70Δ/ku80Δ, technique is used as described for instance in WO 02/052026.

Transformation of host cells with the nucleic acid constructs of the invention and additional genetic modification of the fungal host cells of the invention as described above may be carried out by methods well known in the art. Such methods are e.g. known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

In another aspect the invention relates to a vector comprising a nucleotide sequence encoding a starch active protein as defined above and usable for transformation of a host cell as defined above. In the nucleic acid construct, the coding nucleotide sequences preferably is/are operably linked to a promoter for control and initiation of transcription of the nucleotide sequence in a host cell as defined below. The promoter preferably is capable of causing sufficient expression of the starch active protein described above, in the host cell. Promoters useful in the nucleic acid constructs of the invention include the promoter that in nature provides for expression of the coding genes. Further, both constitutive and inducible natural promoters as well as engineered promoters can be used. Promoters suitable to drive expression of the genes in the hosts of the invention include e.g. promoters from glycolytic genes (e.g. from a glyceraldehyde-3-phosphate dehydrogenase gene), ribosomal protein encoding gene promoters, alcohol dehydrogenase promoters (ADH1, ADH4, and the like), promoters from genes encoding amylo- or cellulolytic enzymes (glucoamylase, TAKA-amylase and cellobiohydrolase). Other promoters, both constitutive and inducible and enhancers or upstream activating sequences will be known to those of skill in the art. The promoters used in the nucleic acid constructs of the present invention may be modified, if desired, to affect their control characteristics. Preferably, the promoter used in the nucleic acid construct for expression of the genes is homologous to the host cell in which genes are expressed.

In the nucleic acid construct, the 3'-end of the coding nucleotide acid sequence(s) preferably is/are operably linked to a transcription terminator sequence. Preferably the terminator sequence is operable in a host cell of choice. In any case the choice of the terminator is not critical; it may e.g. be from any fungal gene, although terminators may sometimes work if from a non-fungal, eukaryotic, gene. The transcription termination sequence further preferably comprises a polyadenylation signal.

Optionally, a selectable marker may be present in the nucleic acid construct. As used herein, the term "marker" refers to a gene encoding a trait or a phenotype which permits the selection of, or the screening for, a host cell containing the marker. A variety of selectable marker genes are available for use in the transformation of fungi. Suitable markers include auxotrophic marker genes involved in amino acid or nucleotide metabolism, such as e.g. genes encoding ornithine-transcarbamylases (argB), orotidine-5'-decarboxylases (pyrG, URA3) or glutamine-amido-transferase indoleglycerol-phosphate-synthase phosphoribosyl-anthranilate isomerases (trpC), or involved in carbon or nitrogen metabolism, such e.g. niaD or facA, and antibiotic resistance markers such as genes providing resistance against phleomycin, bleomycin or neomycin (G418). Preferably, bidirectional selection markers are used for which both a positive and a negative genetic selection is possible. Examples of such bidirectional markers are the pyrG (URA3), facA and amdS genes. Due to their bidirectionality these markers can be deleted from transformed filamentous fungus while leaving the introduced recombinant DNA molecule in place, in order to obtain fungi that do not contain selectable markers. This essence of this MARKER GENE FREE™ transformation technology is disclosed in EP-A-0 635 574, which is herein incorporated by reference. Of these selectable markers the use of dominant and bidirectional selectable markers such as acetamidase genes like the amdS genes of A. nidulans, A. niger and P. chrysogenum is most preferred. In addition to their bidirectionality these markers provide the advantage that they are dominant selectable markers that, the use of which does not require mutant (auxotrophic) strains, but which can be used directly in wild type strains.

Optional further elements that may be present in the nucleic acid constructs of the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence. Suitable episomal nucleic acid constructs may e.g. be based on the yeast 2μ or pKD1 (Fleer et al., 1991, Biotechnology 9: 968-975) plasmids. Alternatively the nucleic acid construct may comprise sequences for integration, preferably by homologous recombination (see e.g. WO98/46772). Such sequences may thus be sequences homologous to the target site for integration in the host cell's genome. The nucleic acid constructs of the invention can be provided in a manner known per se, which generally involves techniques such as restricting and linking nucleic acids/ nucleic acid sequences, for which reference is made to the standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987).

In a further aspect the invention relates to fermentation processes in which the transformed host cells of the invention are used for the conversion of a lignocellulose or (hemi-) cellulose substrate. A preferred fermentation process is an aerobic fermentation process. The fermentation process may either be a submerged or a solid state fermentation process.

In a solid state fermentation process (sometimes referred to as semi-solid state fermentation) the transformed host cells are fermenting on a solid medium that provides anchorage points for the fungus in the absence of any freely flowing substance. The amount of water in the solid medium can be any amount of water. For example, the solid medium could be almost dry, or it could be slushy. A person skilled in the art knows that the terms "solid state fermentation" and "semi-solid state fermentation" are interchangeable. A wide variety of solid state fermentation devices have previously been described (for review see, Larroche et al., "Special Transformation Processes Using Fungal Spores and Immobilized Cells", Adv. Biochem. Eng. Biotech., (1997), Vol 55, pp. 179; Roussos et al., "Zymotis: A large Scale Solid State Fermenter", Applied Biochemistry and Biotechnology, (1993), Vol. 42, pp. 37-52; Smits et al., "Solid-State Fermentation-A Mini Review, 1998), Agro-Food-Industry Hi-Tech, March/April, pp. 29-36). These devices fall within two categories, those categories being static systems and agitated systems. In static systems, the solid media is stationary throughout the fermentation process. Examples of static systems used for solid state fermentation include flasks, petri dishes, trays, fixed bed columns, and ovens. Agitated systems provide a means for mixing the solid media during the fermentation process. One example of an agitated system is a rotating drum (Larroche et al., supra). In a submerged fermentation process on the other hand, the transformed fungal host cells are fermenting while being submerged in a liquid medium, usually in a stirred tank fermenter as are well known in the art, although also other types of fermenters such as e.g. airlift-type fermenters may also be applied (see e.g. U.S. Pat. No. 6,746,862).

Preferred in the invention is a submerged fermentation process, which is performed fed-batch. This means that there is a continuous input of feed containing a carbon source and/or other relevant nutrients in order to improve protein yields. The input of the feed can, for example, be at a constant rate or when the concentration of a specific substrate or fermentation parameter falls below some set point.

Further comprised in the invention is the use of an active protein according to the invention for modification of raw carbohydrate substrate (lignocellulose or (hemi-)cellulose). Preferably said use encompasses hydrolysis of the carbohydrate substrate. Also included in this use is the modification of the substrate by the active protein, thereby allowing other carbohydrate substrate hydrolyzing enzymes to approach the substrate more easily and exert their function in resulting in improved hydrolysis.

EXAMPLES

Examples

Expression of Genes Encoding Lignocellulose and/or (Hemi-)Cellulose Active Proteins in *Aspergillus niger*

In order to unambiguously establish that the discovered proteins aid to the increased saccharification of beta-glucan containing plant derived substrates, a host naturally not expressing these genes was (co-)transformed with the respective genes under control of a suitable promoter.

(I) Gene Design

Synthetic (codon-optimized) full length gene copies from two selected *Podospora anserine* genes were generated CAP 61309: CBM1 Protein A synthetic gene was designed by back translation from the reannotated protein for further reference called CAP61309, originally deposited under number XM_001903499.1, with codon bias for *Aspergillus niger*. The start codon of the protein is part of a BspHI site, so as to fit to the NcoI cloning site of vector pAN52-5doubleNotamdS. At the 3' end of the gene two consecutive stop codons were introduced, followed by a BamHI cloning site.

```
        KpnI BspHI
    1   GGTACCTCATGAAGTTCCACGTCCTCTCCGGCCTCGTCGCCCAGGTCCTCTCCGTTAGCG
    1       M  K  F  H  V  L  S  G  L  V  A  Q  V  L  S

61   CCGGCACCATTCTCTGGGATGGCCGCTTCAACGATATGACCTCCTCCGCCGATCTCAACA
   18    A  G  T  I  L  W  D  G  R  F  N  D  M  T  S  S  A  D  L  N

121   AGTGGTCCTGGGGCAACCAGGTCGGCCCCTACCAGTACTATATCCACGGCTCCTCCCCGG
   38    K  W  S  W  G  N  Q  V  G  P  Y  Q  Y  Y  I  H  G  S  S  P

181    TGTCCGCCTACGTCAACCTGTCCCCCGATTACAAGAACCCCGCCGATACCGGCTCCCGCC
   58    V  S  A  Y  V  N  L  S  P  D  Y  K  N  P  A  D  T  G  S  R

241    AGGGCGCCAAGATCACCCTCGATAACACCGCCTACTGGAACGGCCAGAACATGCGCCGCA
   78    Q  G  A  K  I  T  L  D  N  T  A  Y  W  N  G  Q  N  M  R  R

301    CCGAGCTGATCCCCCAGACTACCGCCGCTATCAACCAGGGCAAGGTCTACTACCACTTCA
   98    T  E  L  I  P  Q  T  T  A  A  I  N  Q  G  K  V  Y  Y  H  F

361   GCCTCATGCGCAAGGATATCAACGCCCCTGCCACCACCCGCGAGCACCAGATCGCTTTCT
  118    S  L  M  R  K  D  I  N  A  P  A  T  T  R  E  H  Q  I  A  F

421   TCGAGTCCCACTTCACCGAGCTGAAGTCCGGCTGGCTCTCCGGCGCTCCCGGCATCTCCG
  138    F  E  S  H  F  T  E  L  K  S  G  W  L  S  G  A  P  G  I  S

481   ATACCCTGCTCCGCTGGTGCGTCGGCGGCCAGACCCAGTGGTCCGTCGAGTGGGCCGCTG
  158    D  T  L  L  R  W  C  V  G  G  Q  T  Q  W  S  V  E  W  A  A

541   ATGTCTGGCACAACGTCGCCTACGAGATCGATTTCGCCGCTGGCACCGTCGGTTTCTGGC
  178    D  V  W  H  N  V  A  Y  E  I  D  F  A  A  G  T  V  G  F  W

601   ACTCCACCGGCTCCGACCCCCTCACCCGCAAGGTCGCCCCCGTCAAGACCAGCACCAGCT
  198    H  S  T  G  S  D  P  L  T  R  K  V  A  P  V  K  T  S  T  S

661   CCAACGGTGCTGACTGGCACGTCGGCGTCCTCGAGCTGCCCCGCTCCGGCTACCCCGATT
  218    S  N  G  A  D  W  H  V  G  V  L  E  L  P  R  S  G  Y  P  D

721   CCAACGAGGATTTCTACTGGTCCGGCGTCTACATCGAGTCCGGCTCCCTCACCACCTCCG
  238    S  N  E  D  F  Y  W  S  G  V  Y  I  E  S  G  S  L  T  T  S
```

```
781  TCGCTGGTCCTGGCCAGCCCATCCCTGGTGACGGCGGCTCCTCCAGCTCCAGCTCCTCCT
258   V  A  G  P  G  Q  P  I  P  G  D  G  G  S  S  S  S  S  S

841  CCTCCGTCCCTTCCTCCACCTCCACCCGCGTGTCCAGCACCTCCACCCCTGCCCCGTGT
278   S  S  V  P  S  S  T  S  T  R  V  S  S  T  S  T  P  A  P  V

901  CCTCCACAACCCTCGTTACCAGCACCACTCGCGTCAGCTCCACCTCTACCTCCAGCGCCG
298   S  S  T  T  L  V  T  S  T  T  R  V  S  S  T  S  T  S  S  A

961  CTCCCGTCCAGACCACCCCCTCCGGCTGCACCGCTGGCCAGTACGCCCAGTGCGACGGCA
318   A  P  V  Q  T  T  P  S  G  C  T  A  G  Q  Y  A  Q  C  D  G

1021 TCGGCTTCTCCGGCTGCAAGACCTGCGCCGCTCCCTACACCTGCAAGTACGGCAACGATT
338   I  G  F  S  G  C  K  T  C  A  A  P  Y  T  C  K  Y  G  N  D

BamHI   SacI
1081 GGTACTCCCAGTGCCTCTGATGAGGATCCGAGCTC
358   W  Y  S  Q  C  L  *  *
```

CAP 68330 DUF1996-CBM1 Protein

A synthetic gene was designed by back translation from the reannotated protein, for further reference called CAP68330, deposited originally under number XM_001907623.1, with codon bias for *Aspergillus niger*. Since the start of the coding sequence thus obtained (MHSRN . . . ) cannot be comprised in a restriction enzyme recognition site that is compatible with NcoI (that serves as the 5' cloning site in vector pAN52-5doubleNotamdS) it was decided to include at the 5' end of the synthetic gene the 3' end of the *Aspergillus* specific gpdA promoter sequence (from SalI to NcoI). SalI is the nearest unique site upstream of NcoI in vector pAN52-5doubleNotamdS.

At the 3' end of the gene two consecutive stop codons were introduced, followed by a BamHI cloning site.

```
          KpnI SalI
1    GGTACCGTCGACCCATCCGGTGCTCTGCACTCGACCTGCTGAGGTCCCTCAGTCCCTGGT

61   AGGCAGCTTTGCCCCGTCTGTCCGCCCGGTGTGTCGGCGGGGTTGACAAGGTCGTTGCGT

121  CAGTCCAACATTTGTTGCCATATTTTCCTGCTCTCCCCACCAGCTGCTCTTTTCTTTTCT

181  CTTTCTTTTCCCATCTTCAGTATATTCATCTTCCCATCCAAGAACCTTTATTTCCCCTAA

241  GTAAGTACTTTGCTACATCCATACTCCATCCTTCCCATCCCTTATTCCTTTGAACCTTTC

301  AGTTCGAGCTTTCCCACTTCATCGCAGCTTGACTAACAGCTACCCCGCTTGAGCAGACAT

361  CACCATGCACTCCCGCAACGTCCTCGCCGCTGCCGTCGCTCTCGCTGGCGCCCCTTCCGT
1     M  H  S  R  N  V  L  A  A  A  V  A  L  A  G  A  P  S  V

421  CCACGCCGTCCTCCGCTTCAGCTGCTCCGAGCTGGTCACCGAGCGCCTCGACCCCCTCGT
20    H  A  V  L  R  F  S  C  S  E  L  V  T  E  R  L  D  P  L  V

481  GTTCCCTGGCGCCATGCAGTCCCCCCACGTCCACCAGATCGTCGGCGGCAACATGTTCAA
40    F  P  G  A  M  Q  S  P  H  V  H  Q  I  V  G  G  N  M  F  N

541  CGTCACTATGGACCCCAACCGCCACAACATCGGCGAGGAAGCCACCTGCACCACCTGTAC
60    V  T  M  D  P  N  R  H  N  I  G  E  E  A  T  C  T  T  C  T

601  CTTCTCCGAGGATTTCTCCAACTACTGGACCGCCATCCTCTACTTCCGCGCTCGCAACGG
80    F  S  E  D  F  S  N  Y  W  T  A  I  L  Y  F  R  A  R  N  G

661  CACCCTCATCCGCGTCCCCCAGCGCCCCAATATCGATTTCGATGGCGCTCGCGGCGGTGG
100   T  L  I  R  V  P  Q  R  P  N  I  D  F  D  G  A  R  G  G

721  CATGACCGTCTACTACACCGCCACCTACCAGAACCACAAGCCCACCGCCTTCCAGCCCGG
120   M  T  V  Y  Y  T  A  T  Y  Q  N  H  K  P  T  A  F  Q  P  G

781  CTTCCGCATGATCGTCGGCAACCCCATGTACCGCACCCAGGCCGAGGCTTCCCGCTACCG
140   F  R  M  I  V  G  N  P  M  Y  R  T  Q  A  E  A  S  R  Y  R

841  CCAGATGACCTTCACCTGCCTCGAAACCCTCTCCACCCGCACCGGCGAAACCACCGAGAT
160   Q  M  T  F  T  C  L  E  T  L  S  T  R  T  G  E  T  T  E  M

901  GCCCAAGCAGCCCTGCCGCGAGGGCATCATGTCCAACGTCCGCTTCCCCACCTGCTGGGA
180   P  K  Q  P  C  R  E  G  I  M  S  N  V  R  F  P  T  C  W  D

961  TGGCAAGACCCTCGATCCCCCCGATCACTCCTCCCACGTCGCCTACCCGTCCTCCGGCAC
200   G  K  T  L  D  P  P  D  H  S  S  H  V  A  Y  P  S  S  G  T
```

```
1021  CTTCGAGTCCGGCGGTCCCTGCCCTGCTTCCCACCCTGTCCGCATCCCCCAGCTGTTCTA
 220    F  E  S  G  G  P  C  P  A  S  H  P  V  R  I  P  Q  L  F  Y

1081  CGAGGTCCTCTGGGATACCCGCCGCTTCAACGATCGCTCCCTCTGGCCCGAGGATGGCTC
 240    E  V  L  W  D  T  R  R  F  N  D  R  S  L  W  P  E  D  G  S

1141  CCAGCCCTTCGTCTGGTCCTACGGCGATTACACCGGCTACGGCACCCACGGCGATTACGT
 260    Q  P  F  V  W  S  Y  G  D  Y  T  G  Y  G  T  H  G  D  Y  V

1201  GTTCGGCTGGAAGGGCGATTCCCTCCAGCGCGCTATGGATGCCAACTGCGATTTCTACTG
 280    F  G  W  K  G  D  S  L  Q  R  A  M  D  A  N  C  D  F  Y  C

1261  CCCCCAGCTCAAGACCCAGTCTATCGCCACCGGCAACCAGTGCCGCCAGAACCAGAAGGT
 300    P  Q  L  K  T  Q  S  I  A  T  G  N  Q  C  R  Q  N  Q  K  V

1321  CGCCGAGAACATCGATGGCCCCTTCGATCGCCTCCCTGGTAACGTCGAGATCACCGGCCC
 320    A  E  N  I  D  G  P  F  D  R  L  P  G  N  V  E  I  T  G  P

1381  TCAGCCTGGCGCCTCCAACCCCAACCCCGGCAATGGCGGTGGCTCTACTCAGACTCCTGT
 360    Q  P  G  A  S  N  P  N  P  G  N  G  G  G  S  T  Q  T  P  V

1441  CCAGCCCACCCCCGTCCCTAACCCTGGCAACGGTGGCGGCTGCTCCGTCCAAAAGTGGGG
 380    Q  P  T  P  V  P  N  P  G  N  G  G  G  C  S  V  Q  K  W  G

1501  CCAGTGCGGCGGTCAGGGCTGGTCCGGTTGCACCGTCTGCGCCTCCGGCTCCACCTGCCG
 400    Q  C  G  G  Q  G  W  S  G  C  T  V  C  A  S  G  S  T  C  R

BamHI SacI
1561  CGCTCAGAACCAGTGGTACTCCCAGTGCCTCTGATGAGGATCCGAGCTC
 420    A  Q  N  Q  W  Y  S  Q  C  L  *  *
```

(II) Overexpression of Synthetic Genes Copies

The synthetic gene copies were inserted in an expression vector based on the *A. nidulans* gpdA promoter, carrying also the amdS selection marker. This *Aspergillus* expression vector pAN52-4-amdSdoubleNotI was derived by cloning the *Aspergillus* selection marker amdS and an additional NotI cloning site into the *Aspergillus* expression vector pAN52-4 (EMBL accession #Z32699).

The resulting expression vectors were introduced in a protease deficient *A. niger* host strain AB1.13 (Punt et al., 2008). AmdS+ transformants were selected using acrylamide selection.

(III) Protocol MicroTiterPlate Cultivation of *Aspergillus*

For cultivation of the strains, standard round bottom 96-well microtiter plates (Corning #3799) were used using a Multitron shaker (Infors) designed for the use with MTP.

Volume: 200 µl MM *Aspergillus* medium per well (MM+ casamino acids+vitamins)

- Each separate well was inoculated with spores (from colonies on plates), using toothpicks.
- MTP was incubated for 48 hours at 33° C., 850 rpm Good growth was confirmed by visual inspection
- MTP was centrifuged 10 min 3500 rpm to allow biomass separation.

(IV) DNS-CMCase Method in MTP

Reagents:

Carboxymethyl cellulose sodium salt (CMC), Avicel or non soluble cellulose 3-5, dinitrosalicylic acid, sodium salt (DNS)
Potassium/sodium tartrate (tetrahydrate)
Sodium hydroxide
Glacial acetic acid Reagent preparation protocol:

1. 0.05M NaAc, pH 4.8: Add 2.85 ml of glacial acetic acid to 900 ml of distilled water, adjust the pH to 4.8 with 50% Sodium hydroxide. Bring to total volume of one liter with distilled water.
2. 1% CMC substrate solution: Add 1 gm CMC to 99 ml NaAc buffer, pH4.8. Keep at 4° C. for at least 1 hour before using. The solution is stable for 3 days at 4° C.
3. 10.67% (w/v) Sodium hydroxide solution: add 32 gm of sodium hydroxide pellets to 300 ml of distilled water.
4. 1% 3-5, dinitrosalicylic acid, sodium salt (DNS): suspend 2 gram of DNS in 100 ml of distilled water and gradually add 30 ml of the 10.67% sodium hydroxide solution while mixing. Warm the suspension in water bath set at 50° C. until the solution is clear. Gradually add 60 gm of potassium/sodium artrate (tetrahydrate) to the solution with continuous mixing. Dilute the solution to 200 ml with distilled water. The solution is stable for 2 months. The solution must be clear when used.

Assay Procedure Protocol:

Making Standard Curve

Choose a lot of cellulase preparation as a standard
Standard Curve: dilute the standard using acetate buffer such that the absorbance (at 540 nm) is between 0.1 and 0.5.
Blank solution: use acetate buffer 0.05M NaAc, pH 4.8 as a blank solution 1. Mix 10 µl of each sample with 90 µl buffer 0.05M NaAc, pH 4, 8 using a 1.1 ml volume, 96-deep well Micro Titer Plate (Oxygen; cat. no. P-DW-11-C). At the same time prepare the standard in the same MTP in duplicate.
2. pre-equilibrate the CMC substrate in a (plastic test plate) in a water bath set at 50° C. for 5 minutes
3. At 20 second intervals, add 100 µl of the CMC substrate (pre-equilibrated at 50° C.) to the enzyme dilution using a multichannel pipette (12 channel). Mix and incubate at 50° C. for 10 minutes. (Incubation time can be adjusted depending on activity level of parental strain).
4. at the same time interval as in step 3, add 300 µl of DNS solution and mix
5. boil the reaction mixture+DNS for exactly 5 minutes by placing the test microtiterplate in a boiling water bath. Cover the tops to prevent evaporation during boiling. As a blanc for remaining glucose in the samples prior to incubation also a duplicate MTP is included in which the reaction is terminated by boiling directly upon addition of the cellulase substrate. All samples, standard and blanks should be boiled together. After boiling, cool the plate in an ice bath 6. Measure the absorbance of the enzyme samples, standard and blancs at 540 nm in a Tecan Infinite 200 microplate reader
   (Measurement range 0-3 OD)

(V) Cellulose Binding Assay

For qualitative evaluation of cellulose binding capacity the following assay was used:
   Incubate 1 ml fermentation samples 1 hour with 10 mg Avicel at 4° C. with gentle mixing.
   Centrifuge 10 min, 3000 g
   Wash the cellulose once with 0.5 ml of 50 mM sodium phosphate pH 7.0
   Elute the bound protein by boiling the cellulose pellet for 10 min in 50 µl of 10% SDS
   Subject 20 µl to SDS-PAGE gel.

(VI) Transformant Screening

For a number of transformants obtained from each of the two expression vectors described MTP cultures were performed.

For both the CAP68330 and CAP61309 transformants the culture supernatant was used in a DNS-CMCase activity assay to identify the transformants with the highest activity level. For each expression vector transformants with increased CMCase activity were identified.

(VII) Fermentation

Transformants selected from the transformant screening were cultivated in standard fed-batch fermentation and the lignocellulose and/or (hemi-)cellulose active proteins produced were analyzed in various cellulase related assays VIII Analysis of *A. niger* Transformants in Controlled Fermentation Medium samples during the various fermentations were taken and samples at the end of fermentation (around 70-100 h) were analyzed for cellulase related activity using both soluble (CMC) and non-soluble (non-soluble cellulose, avicel) cellulase substrates. In addition, as the produced CAP68330 or CAP61309 proteins could also be non-enzymatic accessory proteins potentiating cellulase activity also an assay was performed in the presence of a fixed amount of a commercial cellulase preparation and samples from the culture fluid of the CAP68330 and CAP61309 strains was added Results of these assays are shown in the table below

| | | Substrate | | | |
|---|---|---|---|---|---|
| | | non-soluble cellulose | | Avicel | |
| Strains | CMC | −cellulase | +cellulase | −cellulase | +cellulase |
| Blanc | ND | ND | 0.07 | ND | 1.00 |
| cap68330#4 | 0.25 | 0.15 | 0.26 | 1.92 | 2.06 |
| cap61309#8 | 0.22 | 0.21 | 0.23 | 1.90 | 2.09 |
| CONTROL | 0.31 | 0.17 | 0.21 | 1.53 | 1.86 |

As shown in the table the activity towards CMC and non-soluble cellulose was not increased compared to the control strain not expressing CAP68330 or CAP61309 protein. The background activity level observed in the Control strain originates from native *Aspergillus* proteins releasing reducing sugar equivalents from the various substrates.

In contrast as shown in the table, with Avicel as a substrate the cellulase-related activity was higher for the CAP68330/61309 strains than for the control, indicating the presence of cellulase and/or cellulase enhancing activity due to the presence of the CAP68330 or CAP61309 protein.

IX SDS PAGE and Cellulose Binding Analysis

In addition to activity assays also SDS PAGE was carried out with concentrated fermentation samples. In addition cellulose binding analysis followed by SDS PAGE analysis was carried out. As shown in FIG. 1 for CAP61309 protein an additional protein band was observed in SDS PAGE. This band was also identified by binding to Avicel

The invention claimed is:

1. A method to degrade a raw carbohydrate which method comprises treating the raw carbohydrate with an effective amount of a protein selected from the group consisting of proteins having the following amino acid sequences
  a protein having the amino acid sequence of SEQ ID NO:50
  having the amino acid sequence of SEQ ID NO:51,
  having the amino acid sequence of SEQ ID NO:52,
  having the amino acid sequence of SEQ ID NO:53,
  having the amino acid sequence of SEQ ID NO:55,
  having the amino acid sequence of SEQ ID NO:56,
  having the amino acid sequence of SEQ ID NO:57,
  having the amino acid sequence of SEQ ID NO:58,
  having the amino acid sequence of SEQ ID NO:59,
  having the amino acid sequence of SEQ ID NO:60,
  having the amino acid sequence of SEQ ID NO:61,
  having the amino acid sequence of SEQ ID NO:62,
  having the amino acid sequence of SEQ ID NO:63,
  having the amino acid sequence of SEQ ID NO:64,
  having the amino acid sequence of SEQ ID NO:65,
  having the amino acid sequence of SEQ ID NO:66,
  having the amino acid sequence of SEQ ID NO:67,
  having the amino acid sequence of SEQ ID NO:68,
  having the amino acid sequence of SEQ ID NO:69,
  having the amino acid sequence of SEQ ID NO:70,
  having the amino acid sequence of SEQ ID NO:71,
  having the amino acid sequence of SEQ ID NO:72,
  having the amino acid sequence of SEQ ID NO:73,
  having the amino acid sequence of SEQ ID NO:74,
  having the amino acid sequence of SEQ ID NO:75,
  having the amino acid sequence of SEQ ID NO:76,
  and a protein having a sequence that has an identity of more than 95% with any of said amino acid sequences that retains lignocellulose and/or hemicellulose degrading activity,
  whereby the raw carbohydrate is degraded,
  wherein the raw carbohydrate comprises lignocellulose and/or hemicellulose.

2. The method of claim 1, wherein the protein is a protein having the amino acid sequence of SEQ ID NO:58 or having the amino acid sequence of SEQ ID NO:61.

* * * * *

SEQUENCE LISTING

```
<160> NUMBER OF SEQ ID NOS: 82

<210> SEQ ID NO 1
<211> LENGTH: 56
<212> TYPE: PRT
<213> ORGANISM: Artificial
<220> FEATURE:
<223> OTHER INFORMATION: synthetically constructed consensus DUF 1996
      domain short
<220> FEATURE:
<221> NAME/KEY: VARIANT
<222> LOCATION: (1)..(1)
<223> OTHER INFORMATION: may be N or D
<220> FEATURE:
<221> NAME/KEY: VARIANT
<222> LOCATION: (3)..(3)
<223> OTHER INFORMATION: may be V, L or I
<220> FEATURE:
<221> NAME/KEY: VARIANT
<222> LOCATION: (4)..(4)
<223> OTHER INFORMATION: may be A, I, V or M
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: may be A, F or P
<220> FEATURE:
<221> NAME/KEY: VARIANT
<222> LOCATION: (7)..(7)
```

```
<223> OTHER INFORMATION: may be N, Q or G
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: VARIANT
<222> LOCATION: (11)..(11)
<223> OTHER INFORMATION: may be A, P or S
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (20)..(35)
<223> OTHER INFORMATION: Xaa can be any naturally occurring amino acid
<220> FEATURE:
<221> NAME/KEY: VARIANT
<222> LOCATION: (37)..(37)
<223> OTHER INFORMATION: may be T or S
<220> FEATURE:
<221> NAME/KEY: VARIANT
<222> LOCATION: (38)..(38)
<223> OTHER INFORMATION: may be T or S
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: VARIANT
<222> LOCATION: (47)..(47)
<223> OTHER INFORMATION: may be N or A
<220> FEATURE:
<221> NAME/KEY: VARIANT
<222> LOCATION: (49)..(49)
<223> OTHER INFORMATION: may be W or Y
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: VARIANT
<222> LOCATION: (51)..(51)
<223> OTHER INFORMATION: may be P or A
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: VARIANT
<222> LOCATION: (53)..(53)
<223> OTHER INFORMATION: may be V, M or L
<220> FEATURE:
<221> NAME/KEY: misc_feature
<222> LOCATION: (54)..(55)
<223> OTHER INFORMATION: Xaa can be any naturally occurring amino acid

<400> SEQUENCE: 1

Xaa Pro Xaa Xaa Xaa Xaa Xaa Xaa Xaa Xaa Xaa His Xaa His Xaa
1               5                   10                  15

Xaa Xaa Gly Xaa Xaa Xaa Xaa Xaa Xaa Xaa Xaa Xaa Xaa Xaa Xaa
            20                  25                  30

Xaa Xaa Xaa Cys Xaa Xaa Xaa Xaa Xaa Xaa Xaa Asp Xaa Ser Xaa Tyr
```

```
                35                  40                  45
Xaa Xaa Xaa Xaa Xaa Xaa Xaa Gly
    50                  55

<210> SEQ ID NO 2
<211> LENGTH: 70
<212> TYPE: PRT
<213> ORGANISM: Artificial
<220> FEATURE:
<223> OTHER INFORMATION: synthetically constructed consensus DUF1996
      domain long
<220> FEATURE:
<221> NAME/KEY: VARIANT
<222> LOCATION: (1)..(1)
<223> OTHER INFORMATION: May be N or D
<220> FEATURE:
<221> NAME/KEY: VARIANT
<222> LOCATION: (3)..(3)
<223> OTHER INFORMATION: May be V, L or I
<220> FEATURE:
<221> NAME/KEY: VARIANT
<222> LOCATION: (4)..(4)
<223> OTHER INFORMATION: May be A, I, V or M
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: May be A, F or P
<220> FEATURE:
<221> NAME/KEY: VARIANT
<222> LOCATION: (7)..(7)
<223> OTHER INFORMATION: May be N, Q or G
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: May be A, P or S
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (22)..(42)
<223> OTHER INFORMATION: Xaa can be any naturally occurring amino acid
<220> FEATURE:
<221> NAME/KEY: VARIANT
<222> LOCATION: (44)..(44)
<223> OTHER INFORMATION: May be T or S
<220> FEATURE:
<221> NAME/KEY: VARIANT
<222> LOCATION: (45)..(45)
<223> OTHER INFORMATION: May be T or S
<220> FEATURE:
<221> NAME/KEY: misc_feature
<222> LOCATION: (46)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: VARIANT
```

```
<222> LOCATION: (54)..(54)
<223> OTHER INFORMATION: May be N or A
<220> FEATURE:
<221> NAME/KEY: VARIANT
<222> LOCATION: (56)..(56)
<223> OTHER INFORMATION: May be W or Y
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: VARIANT
<222> LOCATION: (58)..(58)
<223> OTHER INFORMATION: May be P or A
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: VARIANT
<222> LOCATION: (60)..(60)
<223> OTHER INFORMATION: May be V, M or L
<220> FEATURE:
<221> NAME/KEY: misc_feature
<222> LOCATION: (61)..(69)
<223> OTHER INFORMATION: Xaa can be any naturally occurring amino acid

<400> SEQUENCE: 2

Xaa Pro Xaa Xaa Xaa Xaa Xaa Xaa Xaa Xaa Xaa Xaa Xaa His Xaa
1               5                   10                  15

His Xaa Xaa Xaa Gly Xaa Xaa Xaa Xaa Xaa Xaa Xaa Xaa Xaa Xaa
            20                  25                  30

Xaa Xaa Xaa Xaa Xaa Xaa Xaa Xaa Xaa Cys Xaa Xaa Xaa Xaa Xaa
        35                  40                  45

Xaa Xaa Asp Xaa Ser Xaa Tyr Xaa Xaa Ala Xaa Xaa Xaa Xaa Xaa
    50                  55                  60

Xaa Xaa Xaa Xaa Xaa Gly
65                  70

<210> SEQ ID NO 3
<211> LENGTH: 230
<212> TYPE: PRT
<213> ORGANISM: Artificial
<220> FEATURE:
<223> OTHER INFORMATION: synthetically constructed cellulose active
      domain

<400> SEQUENCE: 3

Gly Thr Ile Leu Trp Asp Gly Arg Phe Asn Asp Met Thr Ser Ser Ala
1               5                   10                  15

Asp Leu Asn Lys Trp Ser Trp Gly Asn Gln Val Gly Pro Tyr Gln Tyr
            20                  25                  30

Tyr Ile His Gly Ser Ser Pro Val Ser Ala Tyr Val Asn Leu Ser Pro
        35                  40                  45

Asp Tyr Lys Asn Pro Ala Asp Thr Gly Ser Arg Gln Gly Ala Lys Ile
    50                  55                  60

Thr Leu Asp Asn Thr Ala Tyr Trp Asn Gly Gln Asn Met Arg Arg Thr
65                  70                  75                  80

Glu Leu Ile Pro Gln Thr Thr Ala Ala Ile Asn Gln Gly Lys Val Tyr
                85                  90                  95

Tyr His Phe Ser Leu Met Arg Lys Asp Ile Asn Ala Pro Ala Thr Thr
            100                 105                 110

Arg Glu His Gln Ile Ala Phe Phe Glu Ser His Phe Thr Glu Leu Lys
        115                 120                 125
```

```
Ser Gly Trp Leu Ser Gly Ala Pro Gly Ile Ser Asp Thr Leu Leu Arg
    130                 135                 140

Trp Cys Ile Asp Phe Ala Ala Gly Thr Val Gly Phe Trp His Ser Thr
145                 150                 155                 160

Gly Ser Asp Pro Leu Thr Arg Lys Val Ala Pro Val Lys Thr Ser Thr
                165                 170                 175

Ser Ser Asn Gly Ala Asp Trp His Val Gly Val Leu Glu Leu Pro Arg
                180                 185                 190

Ser Gly Tyr Pro Asp Ser Asn Glu Asp Phe Tyr Trp Ser Gly Val Tyr
            195                 200                 205

Ile Glu Ser Gly Ser Leu Thr Thr Ser Val Ala Gly Pro Gly Gln Pro
210                 215                 220

Ile Pro Gly Asp Gly Gly
225             230

<210> SEQ ID NO 4
<211> LENGTH: 250
<212> TYPE: PRT
<213> ORGANISM: Artificial
<220> FEATURE:
<223> OTHER INFORMATION: synthetically constructed DUF1996 domain

<400> SEQUENCE: 4

Asp Pro Leu Val Phe Pro Gly Ala Met Gln Ser Pro His Val His Gln
1               5                   10                  15

Ile Val Gly Gly Asn Met Phe Asn Val Thr Met Asp Pro Asn Arg His
            20                  25                  30

Asn Ile Gly Glu Glu Ala Thr Cys Thr Thr Cys Thr Phe Ser Glu Asp
        35                  40                  45

Phe Ser Asn Tyr Trp Thr Ala Ile Leu Tyr Phe Arg Ala Arg Asn Gly
50                  55                  60

Thr Leu Ile Arg Val Pro Gln Arg Pro Asn Ile Asp Phe Asp Gly Ala
65                  70                  75                  80

Arg Gly Gly Gly Met Thr Val Tyr Tyr Thr Ala Thr Tyr Gln Asn His
                85                  90                  95

Lys Pro Thr Ala Phe Gln Pro Gly Phe Arg Met Ile Val Gly Asn Pro
            100                 105                 110

Met Tyr Arg Thr Gln Ala Glu Ala Ser Arg Tyr Arg Gln Met Thr Phe
        115                 120                 125

Thr Cys Leu Glu Thr Leu Ser Thr Arg Thr Gly Glu Thr Thr Glu Met
130                 135                 140

Pro Lys Gln Pro Cys Arg Gly Glu Ile Met Ser Asn Val Arg Phe Pro
145                 150                 155                 160

Thr Cys Trp Asp Gly Lys Thr Leu Asp Pro Pro Asp His Ser Ser His
                165                 170                 175

Val Ala Tyr Pro Ser Ser Gly Thr Phe Glu Ser Gly Gly Pro Cys Pro
            180                 185                 190

Ala Ser His Pro Val Arg Ile Pro Gln Leu Phe Tyr Glu Val Leu Trp
        195                 200                 205

Asp Thr Arg Arg Phe Asn Asp Arg Ser Leu Trp Pro Glu Asp Gly Ser
210                 215                 220

Gln Pro Phe Val Trp Ser Tyr Gly Asp Tyr Thr Gly Tyr Gly Thr His
225                 230                 235                 240

Gly Asp Tyr Val Phe Gly Trp Lys Gly Ile
                245                 250
```

<210> SEQ ID NO 5
<211> LENGTH: 330
<212> TYPE: PRT
<213> ORGANISM: Artificial
<220> FEATURE:
<223> OTHER INFORMATION: synthetically constructed DUF1996 domain

<400> SEQUENCE: 5

```
Gly Ala Pro Ser Val His Ala Val Leu Arg Phe Ser Cys Ser Glu Leu
1               5                   10                  15

Val Thr Glu Arg Leu Asp Pro Leu Val Phe Pro Gly Ala Met Gln Ser
            20                  25                  30

Pro His Val His Gln Ile Val Gly Gly Asn Met Phe Asn Val Thr Met
        35                  40                  45

Asp Pro Asn Arg His Asn Ile Gly Glu Ala Thr Cys Thr Thr Cys
    50                  55                  60

Thr Phe Ser Glu Asp Phe Ser Asn Tyr Trp Thr Ala Ile Leu Tyr Phe
65                  70                  75                  80

Arg Ala Arg Asn Gly Thr Leu Ile Arg Val Pro Gln Arg Pro Asn Ile
                85                  90                  95

Asp Phe Asp Gly Ala Arg Gly Gly Met Thr Val Tyr Tyr Thr Ala
            100                 105                 110

Thr Tyr Gln Asn His Lys Pro Thr Ala Phe Gln Pro Gly Phe Arg Met
        115                 120                 125

Ile Val Gly Asn Pro Met Tyr Arg Thr Gln Ala Glu Ala Ser Arg Tyr
130                 135                 140

Arg Gln Met Thr Phe Thr Cys Leu Glu Thr Leu Ser Thr Arg Thr Gly
145                 150                 155                 160

Glu Thr Thr Glu Met Pro Lys Gln Pro Cys Arg Glu Gly Ile Met Ser
                165                 170                 175

Asn Val Arg Phe Pro Thr Cys Trp Asp Gly Lys Thr Leu Asp Pro Pro
            180                 185                 190

Asp His Ser Ser His Val Ala Tyr Pro Ser Ser Gly Thr Phe Glu Ser
        195                 200                 205

Gly Gly Pro Cys Pro Ala Ser His Pro Val Arg Ile Pro Gln Leu Phe
    210                 215                 220

Tyr Glu Val Leu Trp Asp Thr Arg Arg Phe Asn Asp Arg Ser Leu Trp
225                 230                 235                 240

Pro Glu Asp Gly Ser Gln Pro Phe Val Trp Ser Tyr Gly Asp Tyr Thr
                245                 250                 255

Gly Tyr Gly Thr His Gly Asp Tyr Val Phe Gly Trp Lys Gly Asp Ser
            260                 265                 270

Leu Gln Arg Ala Met Asp Ala Asn Cys Asp Phe Tyr Cys Pro Gln Leu
        275                 280                 285

Lys Thr Gln Ser Ile Ala Thr Gly Asn Gln Cys Arg Gln Asn Gln Lys
    290                 295                 300

Val Ala Glu Asn Ile Asp Gly Pro Phe Asp Arg Leu Pro Gly Asn Val
305                 310                 315                 320

Glu Ile Thr Gly Pro Gln Pro Gly Ala Ser
                325                 330
```

<210> SEQ ID NO 6
<211> LENGTH: 202
<212> TYPE: PRT
<213> ORGANISM: Artificial
<220> FEATURE:

```
<223> OTHER INFORMATION: synthetically constructed cellulose active
      domain consensus short
<220> FEATURE:
<221> NAME/KEY: VARIANT
<222> LOCATION: (1)..(1)
<223> OTHER INFORMATION: May be A or G
<220> FEATURE:
<221> NAME/KEY: VARIANT
<222> LOCATION: (2)..(2)
<223> OTHER INFORMATION: May be T or S
<220> FEATURE:
<221> NAME/KEY: VARIANT
<222> LOCATION: (3)..(3)
<223> OTHER INFORMATION: May be V or I
<220> FEATURE:
<221> NAME/KEY: VARIANT
<222> LOCATION: (4)..(4)
<223> OTHER INFORMATION: May be L, V or I
<220> FEATURE:
<221> NAME/KEY: VARIANT
<222> LOCATION: (6)..(6)
<223> OTHER INFORMATION: May be S or D
<220> FEATURE:
<221> NAME/KEY: VARIANT
<222> LOCATION: (8)..(8)
<223> OTHER INFORMATION: May be I, F, S or R
<220> FEATURE:
<221> NAME/KEY: VARIANT
<222> LOCATION: (10)..(10)
<223> OTHER INFORMATION: May be D or N
<220> FEATURE:
<221> NAME/KEY: VARIANT
<222> LOCATION: (11)..(11)
<223> OTHER INFORMATION: May be S or D
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: VARIANT
<222> LOCATION: (14)..(14)
<223> OTHER INFORMATION: May be S or T
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: VARIANT
<222> LOCATION: (18)..(18)
<223> OTHER INFORMATION: May be I, F or L
<220> FEATURE:
<221> NAME/KEY: VARIANT
<222> LOCATION: (19)..(19)
<223> OTHER INFORMATION: May be D or N
<220> FEATURE:
<221> NAME/KEY: VARIANT
<222> LOCATION: (24)..(24)
<223> OTHER INFORMATION: May be S, A or G
<220> FEATURE:
<221> NAME/KEY: VARIANT
<222> LOCATION: (27)..(27)
<223> OTHER INFORMATION: May be V or I
<220> FEATURE:
<221> NAME/KEY: VARIANT
<222> LOCATION: (28)..(28)
<223> OTHER INFORMATION: May be P or G
<220> FEATURE:
<221> NAME/KEY: VARIANT
<222> LOCATION: (29)..(29)
<223> OTHER INFORMATION: May be S or P
<220> FEATURE:
<221> NAME/KEY: VARIANT
<222> LOCATION: (30)..(30)
<223> OTHER INFORMATION: May be W or Y
<220> FEATURE:
<221> NAME/KEY: VARIANT
<222> LOCATION: (32)..(32)
<223> OTHER INFORMATION: May be W or Y
<220> FEATURE:
```

```
<221> NAME/KEY: misc_feature
<222> LOCATION: (38)..(39)
<223> OTHER INFORMATION: Xaa can be any naturally occurring amino acid
<220> FEATURE:
<221> NAME/KEY: VARIANT
<222> LOCATION: (40)..(40)
<223> OTHER INFORMATION: May be T or V
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: VARIANT
<222> LOCATION: (44)..(44)
<223> OTHER INFORMATION: May be L, V or I
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: VARIANT
<222> LOCATION: (46)..(46)
<223> OTHER INFORMATION: May be L, V or I
<220> FEATURE:
<221> NAME/KEY: misc_feature
<222> LOCATION: (48)..(49)
<223> OTHER INFORMATION: Xaa can be any naturally occurring amino acid
<220> FEATURE:
<221> NAME/KEY: VARIANT
<222> LOCATION: (50)..(50)
<223> OTHER INFORMATION: May be Y or F
<220> FEATURE:
<221> NAME/KEY: misc_feature
<222> LOCATION: (54)..(58)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: VARIANT
<222> LOCATION: (62)..(62)
<223> OTHER INFORMATION: May be R or K
<220> FEATURE:
<221> NAME/KEY: VARIANT
<222> LOCATION: (65)..(65)
<223> OTHER INFORMATION: May be I or L
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: VARIANT
<222> LOCATION: (68)..(68)
<223> OTHER INFORMATION: May be T or S
<220> FEATURE:
<221> NAME/KEY: VARIANT
<222> LOCATION: (69)..(69)
<223> OTHER INFORMATION: May be S or A
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: VARIANT
<222> LOCATION: (75)..(75)
<223> OTHER INFORMATION: May be T or N
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: VARIANT
<222> LOCATION: (79)..(79)
<223> OTHER INFORMATION: May be T, S or I
<220> FEATURE:
<221> NAME/KEY: misc_feature
<222> LOCATION: (86)..(91)
<223> OTHER INFORMATION: Xaa can be any naturally occurring amino acid
```

```
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: VARIANT
<222> LOCATION: (94)..(94)
<223> OTHER INFORMATION: May be L, V or K
<220> FEATURE:
<221> NAME/KEY: VARIANT
<222> LOCATION: (95)..(95)
<223> OTHER INFORMATION: May be Y or F
<220> FEATURE:
<221> NAME/KEY: VARIANT
<222> LOCATION: (100)..(100)
<223> OTHER INFORMATION: May be L, V or I
<220> FEATURE:
<221> NAME/KEY: misc_feature
<222> LOCATION: (101)..(105)
<223> OTHER INFORMATION: Xaa can be any naturally occurring amino acid
<220> FEATURE:
<221> NAME/KEY: misc_feature
<222> LOCATION: (109)..(112)
<223> OTHER INFORMATION: Xaa can be any naturally occurring amino acid
<220> FEATURE:
<221> NAME/KEY: VARIANT
<222> LOCATION: (116)..(116)
<223> OTHER INFORMATION: May be L, V or I
<220> FEATURE:
<221> NAME/KEY: VARIANT
<222> LOCATION: (117)..(117)
<223> OTHER INFORMATION: May be C or A
<220> FEATURE:
<221> NAME/KEY: VARIANT
<222> LOCATION: (126)..(126)
<223> OTHER INFORMATION: May be M or L
<220> FEATURE:
<221> NAME/KEY: VARIANT
<222> LOCATION: (128)..(128)
<223> OTHER INFORMATION: May be S, T or Y
<220> FEATURE:
<221> NAME/KEY: misc_feature
<222> LOCATION: (132)..(137)
<223> OTHER INFORMATION: Xaa can be any naturally occurring amino acid
<220> FEATURE:
<221> NAME/KEY: VARIANT
<222> LOCATION: (138)..(138)
<223> OTHER INFORMATION: May be F or L
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: VARIANT
<222> LOCATION: (143)..(143)
<223> OTHER INFORMATION: May be S, D or A
<220> FEATURE:
<221> NAME/KEY: misc_feature
<222> LOCATION: (144)..(146)
<223> OTHER INFORMATION: Xaa can be any naturally occurring amino acid
<220> FEATURE:
<221> NAME/KEY: VARIANT
<222> LOCATION: (148)..(148)
<223> OTHER INFORMATION: May be L or F
<220> FEATURE:
<221> NAME/KEY: VARIANT
<222> LOCATION: (149)..(149)
<223> OTHER INFORMATION: May be W, Y or F
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: VARIANT
<222> LOCATION: (152)..(152)
<223> OTHER INFORMATION: May be N, T or E
<220> FEATURE:
<221> NAME/KEY: misc_feature
<222> LOCATION: (154)..(155)
```

```
<223> OTHER INFORMATION: Xaa can be any naturally occurring amino acid
<220> FEATURE:
<221> NAME/KEY: VARIANT
<222> LOCATION: (156)..(156)
<223> OTHER INFORMATION: May be P or A
<220> FEATURE:
<221> NAME/KEY: misc_feature
<222> LOCATION: (158)..(159)
<223> OTHER INFORMATION: Xaa can be any naturally occurring amino acid
<220> FEATURE:
<221> NAME/KEY: VARIANT
<222> LOCATION: (160)..(160)
<223> OTHER INFORMATION: May be V or A
<220> FEATURE:
<221> NAME/KEY: VARIANT
<222> LOCATION: (161)..(161)
<223> OTHER INFORMATION: May be V or A
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: VARIANT
<222> LOCATION: (163)..(163)
<223> OTHER INFORMATION: May be A, N or P
<220> FEATURE:
<221> NAME/KEY: misc_feature
<222> LOCATION: (164)..(166)
<223> OTHER INFORMATION: Xaa can be any naturally occurring amino acid
<220> FEATURE:
<221> NAME/KEY: VARIANT
<222> LOCATION: (167)..(167)
<223> OTHER INFORMATION: May be S, N or A
<220> FEATURE:
<221> NAME/KEY: VARIANT
<222> LOCATION: (168)..(168)
<223> OTHER INFORMATION: May be T or A
<220> FEATURE:
<221> NAME/KEY: VARIANT
<222> LOCATION: (169)..(169)
<223> OTHER INFORMATION: May be F, S or A
<220> FEATURE:
<221> NAME/KEY: VARIANT
<222> LOCATION: (170)..(170)
<223> OTHER INFORMATION: May be T or S
<220> FEATURE:
<221> NAME/KEY: VARIANT
<222> LOCATION: (171)..(171)
<223> OTHER INFORMATION: May be N or D
<220> FEATURE:
<221> NAME/KEY: VARIANT
<222> LOCATION: (172)..(172)
<223> OTHER INFORMATION: May be S or G
<220> FEATURE:
<221> NAME/KEY: VARIANT
<222> LOCATION: (173)..(173)
<223> OTHER INFORMATION: May be Q or A
<220> FEATURE:
<221> NAME/KEY: VARIANT
<222> LOCATION: (175)..(175)
<223> OTHER INFORMATION: May be W or F
<220> FEATURE:
<221> NAME/KEY: VARIANT
<222> LOCATION: (177)..(177)
<223> OTHER INFORMATION: May be I, L, V or F
<220> FEATURE:
<221> NAME/KEY: VARIANT
<222> LOCATION: (179)..(179)
<223> OTHER INFORMATION: May be E, I, Q or V
<220> FEATURE:
<221> NAME/KEY: VARIANT
<222> LOCATION: (181)..(181)
<223> OTHER INFORMATION: May be R, K or E
<220> FEATURE:
<221> NAME/KEY: VARIANT
<222> LOCATION: (182)..(182)
<223> OTHER INFORMATION: May be L, V or I
<220> FEATURE:
<221> NAME/KEY: misc_feature
```

```
<222> LOCATION: (184)..(191)
<223> OTHER INFORMATION: Xaa can be any naturally occurring amino acid
<220> FEATURE:
<221> NAME/KEY: VARIANT
<222> LOCATION: (194)..(194)
<223> OTHER INFORMATION: May be W, Y or F
<220> FEATURE:
<221> NAME/KEY: VARIANT
<222> LOCATION: (195)..(195)
<223> OTHER INFORMATION: May be Y or F
<220> FEATURE:
<221> NAME/KEY: VARIANT
<222> LOCATION: (196)..(196)
<223> OTHER INFORMATION: May be W or F
<220> FEATURE:
<221> NAME/KEY: VARIANT
<222> LOCATION: (199)..(199)
<223> OTHER INFORMATION: May be V or I
<220> FEATURE:
<221> NAME/KEY: VARIANT
<222> LOCATION: (200)..(200)
<223> OTHER INFORMATION: May be Y or F
<220> FEATURE:
<221> NAME/KEY: VARIANT
<222> LOCATION: (201)..(201)
<223> OTHER INFORMATION: May be V or I

<400> SEQUENCE: 6

Xaa Xaa Xaa Xaa Trp Xaa Gly Xaa Phe Xaa Xaa Xaa Xaa Xaa Xaa
 1               5                  10                  15

Asp Xaa Xaa Lys Trp Ser Trp Xaa Asn Gln Xaa Xaa Xaa Xaa Gln Xaa
            20                  25                  30

Tyr Ile His Gly Ser Xaa Xaa Xaa Xaa Tyr Xaa Xaa Xaa Ser Xaa
            35                  40                  45

Xaa Xaa Lys Asn Pro Xaa Xaa Xaa Xaa Xaa Gln Gly Xaa Xaa Ile Thr
 50                  55                  60

Xaa Asp Xaa Xaa Xaa Xaa Trp Asn Gly Gln Xaa Met Xaa Arg Xaa Glu
 65                  70                  75                  80

Leu Ile Pro Gln Thr Xaa Xaa Xaa Xaa Xaa Gly Xaa Xaa Xaa Tyr
            85                  90                  95

His Phe Ser Xaa Xaa Xaa Xaa Xaa Xaa Asn Ala Pro Xaa Xaa Xaa Xaa
            100                 105                 110

Glu His Gln Xaa Xaa Phe Phe Glu Ser His Phe Thr Glu Xaa Lys Xaa
            115                 120                 125

Gly Trp Gly Xaa Xaa Xaa Xaa Xaa Xaa Xaa Xaa Ile Asp Phe Ala Xaa
            130                 135                 140

Xaa Xaa Val Xaa Xaa Xaa Ser Xaa Gly Xaa Xaa Xaa Leu Xaa Xaa Xaa
145                 150                 155                 160

Xaa Xaa Xaa Xaa Xaa Xaa Xaa Xaa Xaa Xaa Xaa Xaa Xaa Asp Xaa His
            165                 170                 175

Xaa Gly Xaa Leu Xaa Xaa Pro Xaa Xaa Xaa Xaa Xaa Xaa Xaa Glu
            180                 185                 190

Asp Xaa Xaa Xaa Ser Gly Xaa Xaa Xaa Glu
            195                 200

<210> SEQ ID NO 7
<211> LENGTH: 302
<212> TYPE: PRT
<213> ORGANISM: Artificial
<220> FEATURE:
<223> OTHER INFORMATION: synthetically constructed cellulose active
      domain consensus long
<220> FEATURE:
<221> NAME/KEY: VARIANT
<222> LOCATION: (1)..(1)
```

```
<223> OTHER INFORMATION: May be A or G
<220> FEATURE:
<221> NAME/KEY: VARIANT
<222> LOCATION: (2)..(2)
<223> OTHER INFORMATION: May be T or S
<220> FEATURE:
<221> NAME/KEY: VARIANT
<222> LOCATION: (3)..(3)
<223> OTHER INFORMATION: May be V or I
<220> FEATURE:
<221> NAME/KEY: VARIANT
<222> LOCATION: (4)..(4)
<223> OTHER INFORMATION: May be L, V or I
<220> FEATURE:
<221> NAME/KEY: VARIANT
<222> LOCATION: (6)..(6)
<223> OTHER INFORMATION: May be S or D
<220> FEATURE:
<221> NAME/KEY: VARIANT
<222> LOCATION: (8)..(8)
<223> OTHER INFORMATION: May be I, F, S or R
<220> FEATURE:
<221> NAME/KEY: VARIANT
<222> LOCATION: (10)..(10)
<223> OTHER INFORMATION: May be D or N
<220> FEATURE:
<221> NAME/KEY: VARIANT
<222> LOCATION: (11)..(11)
<223> OTHER INFORMATION: May be S or D
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: VARIANT
<222> LOCATION: (14)..(14)
<223> OTHER INFORMATION: May be S or T
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: VARIANT
<222> LOCATION: (18)..(18)
<223> OTHER INFORMATION: May be I, F or L
<220> FEATURE:
<221> NAME/KEY: VARIANT
<222> LOCATION: (19)..(19)
<223> OTHER INFORMATION: May be D or N
<220> FEATURE:
<221> NAME/KEY: VARIANT
<222> LOCATION: (24)..(24)
<223> OTHER INFORMATION: May be S, A or G
<220> FEATURE:
<221> NAME/KEY: VARIANT
<222> LOCATION: (27)..(27)
<223> OTHER INFORMATION: May be V or I
<220> FEATURE:
<221> NAME/KEY: VARIANT
<222> LOCATION: (28)..(28)
<223> OTHER INFORMATION: May be P or G
<220> FEATURE:
<221> NAME/KEY: VARIANT
<222> LOCATION: (29)..(29)
<223> OTHER INFORMATION: May be S or P
<220> FEATURE:
<221> NAME/KEY: VARIANT
<222> LOCATION: (30)..(30)
<223> OTHER INFORMATION: May be W or Y
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: VARIANT
<222> LOCATION: (36)..(36)
<223> OTHER INFORMATION: May be W or Y
<220> FEATURE:
<221> NAME/KEY: misc_feature
```

```
<222> LOCATION: (42)..(43)
<223> OTHER INFORMATION: Xaa can be any naturally occurring amino acid
<220> FEATURE:
<221> NAME/KEY: VARIANT
<222> LOCATION: (44)..(44)
<223> OTHER INFORMATION: May be T or V
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: VARIANT
<222> LOCATION: (48)..(48)
<223> OTHER INFORMATION: May be L, V or I
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: VARIANT
<222> LOCATION: (50)..(50)
<223> OTHER INFORMATION: May be L, V or I
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: VARIANT
<222> LOCATION: (54)..(54)
<223> OTHER INFORMATION: May be Y or F
<220> FEATURE:
<221> NAME/KEY: misc_feature
<222> LOCATION: (58)..(64)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: VARIANT
<222> LOCATION: (68)..(68)
<223> OTHER INFORMATION: May be R or K
<220> FEATURE:
<221> NAME/KEY: VARIANT
<222> LOCATION: (71)..(71)
<223> OTHER INFORMATION: May be I or L
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: VARIANT
<222> LOCATION: (74)..(74)
<223> OTHER INFORMATION: May be T or S
<220> FEATURE:
<221> NAME/KEY: VARIANT
<222> LOCATION: (75)..(75)
<223> OTHER INFORMATION: May be S or A
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: VARIANT
<222> LOCATION: (81)..(81)
<223> OTHER INFORMATION: May be T or N
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: VARIANT
<222> LOCATION: (85)..(85)
<223> OTHER INFORMATION: May be S, T or I
<220> FEATURE:
<221> NAME/KEY: misc_feature
<222> LOCATION: (92)..(104)
<223> OTHER INFORMATION: Xaa can be any naturally occurring amino acid
<220> FEATURE:
```

```
<221> NAME/KEY: misc_feature
<222> LOCATION: (106)..(106)
<223> OTHER INFORMATION: Xaa can be any naturally occurring amino acid
<220> FEATURE:
<221> NAME/KEY: VARIANT
<222> LOCATION: (107)..(107)
<223> OTHER INFORMATION: May be L, V or K
<220> FEATURE:
<221> NAME/KEY: VARIANT
<222> LOCATION: (108)..(108)
<223> OTHER INFORMATION: May be Y or F
<220> FEATURE:
<221> NAME/KEY: VARIANT
<222> LOCATION: (113)..(113)
<223> OTHER INFORMATION: May be L, V or I
<220> FEATURE:
<221> NAME/KEY: misc_feature
<222> LOCATION: (114)..(118)
<223> OTHER INFORMATION: Xaa can be any naturally occurring amino acid
<220> FEATURE:
<221> NAME/KEY: misc_feature
<222> LOCATION: (122)..(125)
<223> OTHER INFORMATION: Xaa can be any naturally occurring amino acid
<220> FEATURE:
<221> NAME/KEY: VARIANT
<222> LOCATION: (129)..(129)
<223> OTHER INFORMATION: May be L, V or I
<220> FEATURE:
<221> NAME/KEY: VARIANT
<222> LOCATION: (130)..(130)
<223> OTHER INFORMATION: May be C or A
<220> FEATURE:
<221> NAME/KEY: misc_feature
<222> LOCATION: (134)..(146)
<223> OTHER INFORMATION: Xaa can be any naturally occurring amino acid
<220> FEATURE:
<221> NAME/KEY: VARIANT
<222> LOCATION: (152)..(152)
<223> OTHER INFORMATION: May be M or L
<220> FEATURE:
<221> NAME/KEY: VARIANT
<222> LOCATION: (154)..(154)
<223> OTHER INFORMATION: May be S, T or Y
<220> FEATURE:
<221> NAME/KEY: misc_feature
<222> LOCATION: (157)..(158)
<223> OTHER INFORMATION: Xaa can be any naturally occurring amino acid
<220> FEATURE:
<221> NAME/KEY: misc_feature
<222> LOCATION: (160)..(192)
<223> OTHER INFORMATION: Xaa can be any naturally occurring amino acid
<220> FEATURE:
<221> NAME/KEY: VARIANT
<222> LOCATION: (193)..(193)
<223> OTHER INFORMATION: May be F or L
<220> FEATURE:
<221> NAME/KEY: misc_feature
<222> LOCATION: (194)..(217)
<223> OTHER INFORMATION: Xaa can be any naturally occurring amino acid
<220> FEATURE:
<221> NAME/KEY: VARIANT
<222> LOCATION: (221)..(221)
<223> OTHER INFORMATION: May be S, D or A
<220> FEATURE:
<221> NAME/KEY: misc_feature
<222> LOCATION: (222)..(229)
<223> OTHER INFORMATION: Xaa can be any naturally occurring amino acid
<220> FEATURE:
<221> NAME/KEY: VARIANT
<222> LOCATION: (231)..(231)
<223> OTHER INFORMATION: May be L or F
<220> FEATURE:
<221> NAME/KEY: VARIANT
<222> LOCATION: (232)..(232)
<223> OTHER INFORMATION: May be W, Y or F
<220> FEATURE:
<221> NAME/KEY: misc_feature
<222> LOCATION: (233)..(233)
<223> OTHER INFORMATION: Xaa can be any naturally occurring amino acid
```

```
<220> FEATURE:
<221> NAME/KEY: VARIANT
<222> LOCATION: (235)..(235)
<223> OTHER INFORMATION: May be N, T or E
<220> FEATURE:
<221> NAME/KEY: misc_feature
<222> LOCATION: (237)..(241)
<223> OTHER INFORMATION: Xaa can be any naturally occurring amino acid
<220> FEATURE:
<221> NAME/KEY: VARIANT
<222> LOCATION: (242)..(242)
<223> OTHER INFORMATION: May be P or A
<220> FEATURE:
<221> NAME/KEY: misc_feature
<222> LOCATION: (244)..(247)
<223> OTHER INFORMATION: Xaa can be any naturally occurring amino acid
<220> FEATURE:
<221> NAME/KEY: VARIANT
<222> LOCATION: (248)..(248)
<223> OTHER INFORMATION: May be V or A
<220> FEATURE:
<221> NAME/KEY: VARIANT
<222> LOCATION: (249)..(249)
<223> OTHER INFORMATION: May be V or A
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: VARIANT
<222> LOCATION: (251)..(251)
<223> OTHER INFORMATION: May be A, N or P
<220> FEATURE:
<221> NAME/KEY: misc_feature
<222> LOCATION: (252)..(256)
<223> OTHER INFORMATION: Xaa can be any naturally occurring amino acid
<220> FEATURE:
<221> NAME/KEY: VARIANT
<222> LOCATION: (257)..(257)
<223> OTHER INFORMATION: May be S, N or A
<220> FEATURE:
<221> NAME/KEY: VARIANT
<222> LOCATION: (258)..(258)
<223> OTHER INFORMATION: May be T or A
<220> FEATURE:
<221> NAME/KEY: VARIANT
<222> LOCATION: (259)..(259)
<223> OTHER INFORMATION: May be F, S or A
<220> FEATURE:
<221> NAME/KEY: VARIANT
<222> LOCATION: (260)..(260)
<223> OTHER INFORMATION: May be T or S
<220> FEATURE:
<221> NAME/KEY: VARIANT
<222> LOCATION: (261)..(261)
<223> OTHER INFORMATION: May be N or D
<220> FEATURE:
<221> NAME/KEY: VARIANT
<222> LOCATION: (262)..(262)
<223> OTHER INFORMATION: May be S or G
<220> FEATURE:
<221> NAME/KEY: VARIANT
<222> LOCATION: (263)..(263)
<223> OTHER INFORMATION: May be Q or A
<220> FEATURE:
<221> NAME/KEY: VARIANT
<222> LOCATION: (265)..(265)
<223> OTHER INFORMATION: May be W or F
<220> FEATURE:
<221> NAME/KEY: VARIANT
<222> LOCATION: (267)..(267)
<223> OTHER INFORMATION: May be I, L, V or F
<220> FEATURE:
<221> NAME/KEY: VARIANT
<222> LOCATION: (269)..(269)
<223> OTHER INFORMATION: May be E, I, Q, V or E
<220> FEATURE:
<221> NAME/KEY: VARIANT
<222> LOCATION: (271)..(271)
```

```
<223> OTHER INFORMATION: May be R, K or E
<220> FEATURE:
<221> NAME/KEY: VARIANT
<222> LOCATION: (272)..(272)
<223> OTHER INFORMATION: May be L, V or I
<220> FEATURE:
<221> NAME/KEY: misc_feature
<222> LOCATION: (274)..(291)
<223> OTHER INFORMATION: Xaa can be any naturally occurring amino acid
<220> FEATURE:
<221> NAME/KEY: VARIANT
<222> LOCATION: (294)..(294)
<223> OTHER INFORMATION: May be W, Y or F
<220> FEATURE:
<221> NAME/KEY: VARIANT
<222> LOCATION: (295)..(295)
<223> OTHER INFORMATION: May be Y or F
<220> FEATURE:
<221> NAME/KEY: VARIANT
<222> LOCATION: (296)..(296)
<223> OTHER INFORMATION: May be W or F
<220> FEATURE:
<221> NAME/KEY: VARIANT
<222> LOCATION: (299)..(299)
<223> OTHER INFORMATION: May be V or I
<220> FEATURE:
<221> NAME/KEY: VARIANT
<222> LOCATION: (300)..(300)
<223> OTHER INFORMATION: May be Y or F
<220> FEATURE:
<221> NAME/KEY: VARIANT
<222> LOCATION: (301)..(301)
<223> OTHER INFORMATION: May be V or I

<400> SEQUENCE: 7

Xaa Xaa Xaa Xaa Trp Xaa Gly Xaa Phe Xaa Xaa Xaa Xaa Xaa Xaa
1               5                   10                  15

Asp Xaa Xaa Lys Trp Ser Trp Xaa Asn Gln Xaa Xaa Xaa Xaa Xaa
            20                  25                  30

Xaa Xaa Gln Xaa Tyr Ile His Gly Ser Xaa Xaa Xaa Xaa Tyr Xaa
        35                  40                  45

Xaa Xaa Ser Xaa Xaa Xaa Lys Asn Pro Xaa Xaa Xaa Xaa Xaa Xaa
    50                  55                  60

Gln Gly Xaa Xaa Ile Thr Xaa Asp Xaa Xaa Xaa Trp Asn Gly Gln
65                  70                  75                  80

Xaa Met Xaa Arg Xaa Glu Leu Ile Pro Gln Thr Xaa Xaa Xaa Xaa
            85                  90                  95

Xaa Xaa Xaa Xaa Xaa Xaa Xaa Gly Xaa Xaa Xaa Tyr His Phe Ser
                100                 105                 110

Xaa Xaa Xaa Xaa Xaa Xaa Asn Ala Pro Xaa Xaa Xaa Glu His Gln
        115                 120                 125

Xaa Xaa Phe Phe Glu Xaa Xaa Xaa Xaa Xaa Xaa Xaa Xaa Xaa Xaa
    130                 135                 140

Xaa Xaa Ser His Phe Thr Glu Xaa Lys Xaa Gly Trp Xaa Gly Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Ile Asp Phe Xaa Xaa Xaa Xaa
        210                 215                 220

Xaa Xaa Xaa Xaa Xaa Val Xaa Xaa Xaa Ser Xaa Gly Xaa Xaa Xaa Xaa
```

```
225                 230                 235                 240

Xaa Ala Leu Xaa Xaa Xaa Xaa Ala Ala Xaa Pro Xaa Xaa Xaa Xaa Xaa
                245                 250                 255

Xaa Xaa Xaa Xaa Xaa Xaa Xaa Asp Xaa His Xaa Gly Xaa Leu Xaa Xaa
            260                 265                 270

Pro Xaa Xaa Xaa Xaa Xaa Xaa Xaa Xaa Xaa Xaa Xaa Xaa Xaa Xaa Xaa
        275                 280                 285

Xaa Xaa Xaa Glu Asp Xaa Xaa Xaa Ser Gly Xaa Xaa Xaa Glu
    290                 295                 300
```

<210> SEQ ID NO 8
<211> LENGTH: 27
<212> TYPE: PRT
<213> ORGANISM: Artificial
<220> FEATURE:
<223> OTHER INFORMATION: synthetically constructed consensus SBM1 domain short
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: VARIANT
<222> LOCATION: (21)..(21)
<223> OTHER INFORMATION: May be H, G, S or N
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: VARIANT
<222> LOCATION: (23)..(23)
<223> OTHER INFORMATION: May be Y, W, M, I or F
<220> FEATURE:
<221> NAME/KEY: misc_feature
<222> LOCATION: (24)..(25)
<223> OTHER INFORMATION: Xaa can be any naturally occurring amino acid

<400> SEQUENCE: 8

```
Cys Gly Gly Xaa Xaa Xaa Xaa Gly Xaa Xaa Xaa Cys Xaa Xaa Xaa Xaa
1               5                   10                  15

Cys Xaa Xaa Xaa Xaa Xaa Xaa Xaa Xaa Gln Cys
            20                  25
```

<210> SEQ ID NO 9
<211> LENGTH: 33
<212> TYPE: PRT
<213> ORGANISM: Artificial
<220> FEATURE:
<223> OTHER INFORMATION: synthetically constructed CBMI domain consensus long
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid

```
<220> FEATURE:
<221> NAME/KEY: misc_feature
<222> LOCATION: (16)..(20)
<223> OTHER INFORMATION: Xaa can be any naturally occurring amino acid
<220> FEATURE:
<221> NAME/KEY: misc_feature
<222> LOCATION: (22)..(26)
<223> OTHER INFORMATION: Xaa can be any naturally occurring amino acid
<220> FEATURE:
<221> NAME/KEY: VARIANT
<222> LOCATION: (27)..(27)
<223> OTHER INFORMATION: May be H, G, S or N
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: VARIANT
<222> LOCATION: (29)..(29)
<223> OTHER INFORMATION: May be Y, W, M, I or F
<220> FEATURE:
<221> NAME/KEY: misc_feature
<222> LOCATION: (30)..(31)
<223> OTHER INFORMATION: Xaa can be any naturally occurring amino acid

<400> SEQUENCE: 9

Cys Gly Gly Xaa Xaa Xaa Xaa Xaa Xaa Gly Xaa Xaa Xaa Cys Xaa
1               5                   10                  15

Xaa Xaa Xaa Xaa Cys Xaa Xaa Xaa Xaa Xaa Xaa Xaa Xaa Xaa Gln
            20                  25                  30

Cys

<210> SEQ ID NO 10
<211> LENGTH: 230
<212> TYPE: PRT
<213> ORGANISM: Podospora anserina

<400> SEQUENCE: 10

Gly Thr Ile Leu Trp Asp Gly Arg Phe Asn Asp Met Thr Ser Ser Ala
1               5                   10                  15

Asp Leu Asn Lys Trp Ser Trp Gly Asn Gln Val Gly Pro Tyr Gln Tyr
            20                  25                  30

Tyr Ile His Gly Ser Ser Pro Val Ser Ala Tyr Val Asn Leu Ser Pro
        35                  40                  45

Asp Tyr Lys Asn Pro Ala Asp Thr Gly Ser Arg Gln Gly Ala Lys Ile
    50                  55                  60

Thr Leu Asp Asn Thr Ala Tyr Trp Asn Gly Gln Asn Met Arg Arg Thr
65                  70                  75                  80

Glu Leu Ile Pro Gln Thr Thr Ala Ala Ile Asn Gln Gly Lys Val Tyr
                85                  90                  95

Tyr His Phe Ser Leu Met Arg Lys Asp Ile Asn Ala Pro Ala Thr Thr
            100                 105                 110

Arg Glu His Gln Ile Ala Phe Phe Glu Ser His Phe Thr Glu Leu Lys
        115                 120                 125

Ser Gly Trp Leu Ser Gly Ala Pro Gly Ile Ser Asp Thr Leu Leu Arg
    130                 135                 140

Trp Cys Ile Asp Phe Ala Ala Gly Thr Val Gly Phe Trp His Ser Thr
145                 150                 155                 160

Gly Ser Asp Pro Leu Thr Arg Lys Val Ala Pro Val Lys Thr Ser Thr
                165                 170                 175

Ser Ser Asn Gly Ala Asp Trp His Val Gly Val Leu Glu Leu Pro Arg
            180                 185                 190
```

Ser Gly Tyr Pro Asp Ser Asn Glu Asp Phe Tyr Trp Ser Gly Val Tyr
            195                 200                 205

Ile Glu Ser Gly Ser Leu Thr Thr Ser Val Ala Gly Pro Gly Gln Pro
        210                 215                 220

Ile Pro Gly Asp Gly Gly
225                 230

<210> SEQ ID NO 11
<211> LENGTH: 252
<212> TYPE: PRT
<213> ORGANISM: Podospora anserina

<400> SEQUENCE: 11

Gly Ala Val Leu Trp Asp Gly Arg Phe Asn Asp Phe Thr Ser Ser Ala
1               5                   10                  15

Asp Leu Asn Lys Trp Ser Trp Ala Asn Gln Val Gly Pro Tyr Pro Phe
            20                  25                  30

Thr Asn Lys Glu Tyr Tyr Ile His Gly Ser Gly Thr Val Asn Arg Tyr
        35                  40                  45

Ile Asn Leu Ser Pro Asp Tyr Lys Asn Pro Asn Asp Thr Val Ser Lys
    50                  55                  60

Gln Gly Ala Arg Phe Thr Leu Asp Ser Thr Ala Tyr Trp Asn Gly Gln
65                  70                  75                  80

Thr Met Arg Arg Ile Glu Leu Ile Pro Gln Thr Lys Ala Ala Ile Asn
                85                  90                  95

Arg Gly Lys Val Phe Tyr His Phe Ser Ile Ser Arg Arg Asp Thr Asn
            100                 105                 110

Ala Pro Ser Val Asn Lys Glu His Gln Ile Cys Phe Phe Glu Ser His
        115                 120                 125

Phe Thr Glu Leu Lys Tyr Gly Trp Ile Ser Gly Glu Gln Gly Ala Ala
    130                 135                 140

Asn Pro Ala Leu Gln Trp Met Thr Asn Gln Arg Thr Gln Trp Lys Leu
145                 150                 155                 160

Ser Glu Trp Lys Ala Asn Val Trp His Asn Phe Ala Tyr Glu Ile Asp
                165                 170                 175

Phe Ser Gly Asn Arg Val Gly Leu Trp Tyr Ser Glu Gly Gly Ala Asp
            180                 185                 190

Leu Lys Gln Val Val Ala Pro Val Gly Val Ser Thr Ser Ser Asn
        195                 200                 205

Gly Gln Asp Trp His Leu Gly Val Leu Glu Leu Pro Arg Ser Gly Tyr
    210                 215                 220

Pro Asn Thr Asn Glu Asp Tyr Tyr Phe Ser Gly Val Phe Ile Glu Asp
225                 230                 235                 240

Gly Ala Ile Thr Thr Lys Ile Gly Gly Pro Gly Glu
                245                 250

<210> SEQ ID NO 12
<211> LENGTH: 1115
<212> TYPE: DNA
<213> ORGANISM: Artificial
<220> FEATURE:
<223> OTHER INFORMATION: synthetically constructed CAP61309
<220> FEATURE:
<221> NAME/KEY: CDS
<222> LOCATION: (9)..(1097)

<400> SEQUENCE: 12 ggtacctc atg aag ttc cac gtc ctc tcc ggc ctc gtc gcc cag gtc ctc    50

```
            Met Lys Phe His Val Leu Ser Gly Leu Val Ala Gln Val Leu
            1               5                   10 tcc gtt agc gcc ggc acc att ctc tgg gat ggc cgc ttc aac gat atg      98
Ser Val Ser Ala Gly Thr Ile Leu Trp Asp Gly Arg Phe Asn Asp Met
15                  20                  25                  30 acc tcc tcc gcc gat ctc aac aag tgg tcc tgg ggc aac cag gtc ggc     146
Thr Ser Ser Ala Asp Leu Asn Lys Trp Ser Trp Gly Asn Gln Val Gly
                35                  40                  45 ccc tac cag tac tat atc cac ggc tcc tcc ccg gtg tcc gcc tac gtc     194
Pro Tyr Gln Tyr Tyr Ile His Gly Ser Ser Pro Val Ser Ala Tyr Val
                50                  55                  60 aac ctg tcc ccc gat tac aag aac ccc gcc gat acc ggc tcc cgc cag     242
Asn Leu Ser Pro Asp Tyr Lys Asn Pro Ala Asp Thr Gly Ser Arg Gln
            65                  70                  75 ggc gcc aag atc acc ctc gat aac acc gcc tac tgg aac ggc cag aac     290
Gly Ala Lys Ile Thr Leu Asp Asn Thr Ala Tyr Trp Asn Gly Gln Asn
        80                  85                  90 atg cgc cgc acc gag ctg atc ccc cag act acc gcc gct atc aac cag     338
Met Arg Arg Thr Glu Leu Ile Pro Gln Thr Thr Ala Ala Ile Asn Gln
95                  100                 105                 110 ggc aag gtc tac tac cac ttc agc ctc atg cgc aag gat atc aac gcc     386
Gly Lys Val Tyr Tyr His Phe Ser Leu Met Arg Lys Asp Ile Asn Ala
                115                 120                 125 cct gcc acc acc cgc gag cac cag atc gct ttc ttc gag tcc cac ttc     434
Pro Ala Thr Thr Arg Glu His Gln Ile Ala Phe Phe Glu Ser His Phe
                130                 135                 140 acc gag ctg aag tcc ggc tgg ctc tcc ggc gct ccc ggc atc tcc gat     482
Thr Glu Leu Lys Ser Gly Trp Leu Ser Gly Ala Pro Gly Ile Ser Asp
            145                 150                 155 acc ctg ctc cgc tgg tgc gtc ggc ggc cag acc cag tgg tcc gtc gag     530
Thr Leu Leu Arg Trp Cys Val Gly Gly Gln Thr Gln Trp Ser Val Glu
        160                 165                 170 tgg gcc gct gat gtc tgg cac aac gtc gcc tac gag atc gat ttc gcc     578
Trp Ala Ala Asp Val Trp His Asn Val Ala Tyr Glu Ile Asp Phe Ala
175                 180                 185                 190 gct ggc acc gtc ggt ttc tgg cac tcc acc ggc tcc gac ccc ctc acc     626
Ala Gly Thr Val Gly Phe Trp His Ser Thr Gly Ser Asp Pro Leu Thr
                195                 200                 205 cgc aag gtc gcc ccc gtc aag acc agc acc agc tcc aac ggt gct gac     674
Arg Lys Val Ala Pro Val Lys Thr Ser Thr Ser Ser Asn Gly Ala Asp
                210                 215                 220 tgg cac gtc ggc gtc ctc gag ctg ccc cgc tcc ggc tac ccc gat tcc     722
Trp His Val Gly Val Leu Glu Leu Pro Arg Ser Gly Tyr Pro Asp Ser
            225                 230                 235 aac gag gat ttc tac tgg tcc ggc gtc tac atc gag tcc ggc tcc ctc     770
Asn Glu Asp Phe Tyr Trp Ser Gly Val Tyr Ile Glu Ser Gly Ser Leu
        240                 245                 250 acc acc tcc gtc gct ggt cct ggc cag ccc atc cct ggt gac ggc ggc     818
Thr Thr Ser Val Ala Gly Pro Gly Gln Pro Ile Pro Gly Asp Gly Gly
255                 260                 265                 270 tcc tcc agc tcc agc tcc tcc tcc gtc cct tcc tcc acc tcc acc         866
Ser Ser Ser Ser Ser Ser Ser Ser Val Pro Ser Ser Thr Ser Thr
                275                 280                 285 cgc gtg tcc agc acc tcc acc cct gcc ccc gtg tcc tcc aca acc ctc     914
Arg Val Ser Ser Thr Ser Thr Pro Ala Pro Val Ser Ser Thr Thr Leu
                290                 295                 300 gtt acc agc acc act cgc gtc agc tcc acc tct acc tcc agc gcc gct     962
Val Thr Ser Thr Thr Arg Val Ser Ser Thr Ser Thr Ser Ser Ala Ala
            305                 310                 315
```

```
ccc gtc cag acc acc ccc tcc ggc tgc acc gct ggc cag tac gcc cag      1010
Pro Val Gln Thr Thr Pro Ser Gly Cys Thr Ala Gly Gln Tyr Ala Gln
    320             325                 330 tgc gac ggc atc ggc ttc tcc ggc tgc aag acc tgc gcc gct ccc tac      1058
Cys Asp Gly Ile Gly Phe Ser Gly Cys Lys Thr Cys Ala Ala Pro Tyr
335             340                 345                 350 acc tgc aag tac ggc aac gat tgg tac tcc cag tgc ctc tgatgaggat       1107
Thr Cys Lys Tyr Gly Asn Asp Trp Tyr Ser Gln Cys Leu
                355                 360 ccgagctc                                                              1115

<210> SEQ ID NO 13
<211> LENGTH: 363
<212> TYPE: PRT
<213> ORGANISM: Artificial
<220> FEATURE:
<223> OTHER INFORMATION: Synthetic Construct

<400> SEQUENCE: 13

Met Lys Phe His Val Leu Ser Gly Leu Val Ala Gln Val Leu Ser Val
1               5                   10                  15

Ser Ala Gly Thr Ile Leu Trp Asp Gly Arg Phe Asn Asp Met Thr Ser
            20                  25                  30

Ser Ala Asp Leu Asn Lys Trp Ser Trp Gly Asn Gln Val Gly Pro Tyr
        35                  40                  45

Gln Tyr Tyr Ile His Gly Ser Ser Pro Val Ser Ala Tyr Val Asn Leu
    50                  55                  60

Ser Pro Asp Tyr Lys Asn Pro Ala Asp Thr Gly Ser Arg Gln Gly Ala
65                  70                  75                  80

Lys Ile Thr Leu Asp Asn Thr Ala Tyr Trp Asn Gly Gln Asn Met Arg
                85                  90                  95

Arg Thr Glu Leu Ile Pro Gln Thr Thr Ala Ala Ile Asn Gln Gly Lys
            100                 105                 110

Val Tyr Tyr His Phe Ser Leu Met Arg Lys Asp Ile Asn Ala Pro Ala
        115                 120                 125

Thr Thr Arg Glu His Gln Ile Ala Phe Phe Glu Ser His Phe Thr Glu
130                 135                 140

Leu Lys Ser Gly Trp Leu Ser Gly Ala Pro Gly Ile Ser Asp Thr Leu
145                 150                 155                 160

Leu Arg Trp Cys Val Gly Gly Gln Thr Gln Trp Ser Val Glu Trp Ala
                165                 170                 175

Ala Asp Val Trp His Asn Val Ala Tyr Glu Ile Asp Phe Ala Ala Gly
            180                 185                 190

Thr Val Gly Phe Trp His Ser Thr Gly Ser Asp Pro Leu Thr Arg Lys
        195                 200                 205

Val Ala Pro Val Lys Thr Ser Thr Ser Ser Asn Gly Ala Asp Trp His
210                 215                 220

Val Gly Val Leu Glu Leu Pro Arg Ser Gly Tyr Pro Asp Ser Asn Glu
225                 230                 235                 240

Asp Phe Tyr Trp Ser Gly Val Tyr Ile Glu Ser Gly Ser Leu Thr Thr
                245                 250                 255

Ser Val Ala Gly Pro Gly Gln Pro Ile Pro Gly Asp Gly Gly Ser Ser
            260                 265                 270

Ser Ser Ser Ser Ser Ser Val Pro Ser Ser Thr Ser Thr Arg Val
        275                 280                 285

Ser Ser Thr Ser Thr Pro Ala Pro Val Ser Ser Thr Thr Leu Val Thr
```

```
                  290                 295                 300
Ser Thr Thr Arg Val Ser Ser Thr Ser Thr Ser Ser Ala Ala Pro Val
305                 310                 315                 320

Gln Thr Thr Pro Ser Gly Cys Thr Ala Gly Gln Tyr Ala Gln Cys Asp
                325                 330                 335

Gly Ile Gly Phe Ser Gly Cys Lys Thr Cys Ala Ala Pro Tyr Thr Cys
                340                 345                 350

Lys Tyr Gly Asn Asp Trp Tyr Ser Gln Cys Leu
            355                 360

<210> SEQ ID NO 14
<211> LENGTH: 1609
<212> TYPE: DNA
<213> ORGANISM: Artificial
<220> FEATURE:
<223> OTHER INFORMATION: synthetically constructed CAP 68330
<220> FEATURE:
<221> NAME/KEY: CDS
<222> LOCATION: (365)..(1591)

<400> SEQUENCE: 14
```

| | | | | | |
|---|---|---|---|---|---|
| ggtaccgtcg | acccatccgg | tgctctgcac | tcgacctgct | gaggtccctc | agtccctggt | 60 |
| aggcagcttt | gccccgtctg | tccgcccggt | gtgtcggcgg | ggttgacaag | gtcgttgcgt | 120 |
| cagtccaaca | tttgttgcca | tattttcctg | ctctccccac | cagctgctct | ttctttttct | 180 |
| cttctttttc | ccatcttcag | tatattcatc | ttcccatcca | agaaccttta | tttcccctaa | 240 |
| gtaagtactt | tgctacatcc | atactccatc | cttcccatcc | cttattcctt | tgaacctttc | 300 |
| agttcgagct | ttcccacttc | atcgcagctt | gactaacagc | taccccgctt | gagcagacat | 360 |

```
cacc atg cac tcc cgc aac gtc ctc gcc gct gcc gtc gct ctc gct ggc        409
     Met His Ser Arg Asn Val Leu Ala Ala Ala Val Ala Leu Ala Gly
      1               5                  10                  15 gcc cct tcc gtc cac gcc gtc ctc cgc ttc agc tgc tcc gag ctg gtc        457
Ala Pro Ser Val His Ala Val Leu Arg Phe Ser Cys Ser Glu Leu Val
                 20                  25                  30 acc gag cgc ctc gac ccc ctc gtg ttc cct ggc gcc atg cag tcc ccc        505
Thr Glu Arg Leu Asp Pro Leu Val Phe Pro Gly Ala Met Gln Ser Pro
         35                  40                  45 cac gtc cac cag atc gtc ggc ggc aac atg ttc aac gtc act atg gac        553
His Val His Gln Ile Val Gly Gly Asn Met Phe Asn Val Thr Met Asp
     50                  55                  60 ccc aac cgc cac aac atc ggc gag gaa gcc acc tgc acc acc tgt acc        601
Pro Asn Arg His Asn Ile Gly Glu Glu Ala Thr Cys Thr Thr Cys Thr
 65                  70                  75 ttc tcc gag gat ttc tcc aac tac tgg acc gcc atc ctc tac ttc cgc        649
Phe Ser Glu Asp Phe Ser Asn Tyr Trp Thr Ala Ile Leu Tyr Phe Arg
 80                  85                  90                  95 gct cgc aac ggc acc ctc atc cgc gtc ccc cag cgc ccc aat atc gat        697
Ala Arg Asn Gly Thr Leu Ile Arg Val Pro Gln Arg Pro Asn Ile Asp
                100                 105                 110 ttc gat ggc gct cgc ggc ggt ggc atg acc gtc tac tac acc gcc acc        745
Phe Asp Gly Ala Arg Gly Gly Gly Met Thr Val Tyr Tyr Thr Ala Thr
            115                 120                 125 tac cag aac cac aag ccc acc gcc ttc cag ccc ggc ttc cgc atg atc        793
Tyr Gln Asn His Lys Pro Thr Ala Phe Gln Pro Gly Phe Arg Met Ile
        130                 135                 140 gtc ggc aac ccc atg tac cgc acc cag gcc gag gct tcc cgc tac cgc        841
Val Gly Asn Pro Met Tyr Arg Thr Gln Ala Glu Ala Ser Arg Tyr Arg
145                 150                 155
```

| | | |
|---|---|---|
| cag atg acc ttc acc tgc ctc gaa acc ctc tcc acc cgc acc ggc gaa<br>Gln Met Thr Phe Thr Cys Leu Glu Thr Leu Ser Thr Arg Thr Gly Glu<br>160                       165                  170               175 | | 889 |
| acc acc gag atg ccc aag cag ccc tgc cgc gag ggc atc atg tcc aac<br>Thr Thr Glu Met Pro Lys Gln Pro Cys Arg Glu Gly Ile Met Ser Asn<br>                   180                  185                  190 | | 937 |
| gtc cgc ttc ccc acc tgc tgg gat ggc aag acc ctc gat ccc ccc gat<br>Val Arg Phe Pro Thr Cys Trp Asp Gly Lys Thr Leu Asp Pro Pro Asp<br>                   195                  200                  205 | | 985 |
| cac tcc tcc cac gtc gcc tac ccg tcc tcc ggc acc ttc gag tcc ggc<br>His Ser Ser His Val Ala Tyr Pro Ser Ser Gly Thr Phe Glu Ser Gly<br>             210                  215                  220 | | 1033 |
| ggt ccc tgc cct gct tcc cac cct gtc cgc atc ccc cag ctg ttc tac<br>Gly Pro Cys Pro Ala Ser His Pro Val Arg Ile Pro Gln Leu Phe Tyr<br>225                       230                  235 | | 1081 |
| gag gtc ctc tgg gat acc cgc cgc ttc aac gat cgc tcc ctc tgg ccc<br>Glu Val Leu Trp Asp Thr Arg Arg Phe Asn Asp Arg Ser Leu Trp Pro<br>240                       245                  250               255 | | 1129 |
| gag gat ggc tcc cag ccc ttc gtc tgg tcc tac ggc gat tac acc ggc<br>Glu Asp Gly Ser Gln Pro Phe Val Trp Ser Tyr Gly Asp Tyr Thr Gly<br>                   260                  265                  270 | | 1177 |
| tac ggc acc cac ggc gat tac gtg ttc ggc tgg aag ggc gat tcc ctc<br>Tyr Gly Thr His Gly Asp Tyr Val Phe Gly Trp Lys Gly Asp Ser Leu<br>             275                  280                  285 | | 1225 |
| cag cgc gct atg gat gcc aac tgc gat ttc tac tgc ccc cag ctc aag<br>Gln Arg Ala Met Asp Ala Asn Cys Asp Phe Tyr Cys Pro Gln Leu Lys<br>290                       295                  300 | | 1273 |
| acc cag tct atc gcc acc ggc aac cag tgc cgc cag aac cag aag gtc<br>Thr Gln Ser Ile Ala Thr Gly Asn Gln Cys Arg Gln Asn Gln Lys Val<br>305                       310                  315 | | 1321 |
| gcc gag aac atc gat ggc ccc ttc gat cgc ctc cct ggt aac gtc gag<br>Ala Glu Asn Ile Asp Gly Pro Phe Asp Arg Leu Pro Gly Asn Val Glu<br>320                       325                  330               335 | | 1369 |
| atc acc ggc cct cag cct ggc gcc tcc aac ccc aac ccc ggc aat ggc<br>Ile Thr Gly Pro Gln Pro Gly Ala Ser Asn Pro Asn Pro Gly Asn Gly<br>                   340                  345                  350 | | 1417 |
| ggt ggc tct act cag act cct gtc cag ccc acc ccc gtc cct aac cct<br>Gly Gly Ser Thr Gln Thr Pro Val Gln Pro Thr Pro Val Pro Asn Pro<br>             355                  360                  365 | | 1465 |
| ggc aac ggt ggc ggc tgc tcc gtc caa aag tgg ggc cag tgc ggc ggt<br>Gly Asn Gly Gly Gly Cys Ser Val Gln Lys Trp Gly Gln Cys Gly Gly<br>370                       375                  380 | | 1513 |
| cag ggc tgg tcc ggt tgc acc gtc tgc gcc tcc ggc tcc acc tgc cgc<br>Gln Gly Trp Ser Gly Cys Thr Val Cys Ala Ser Gly Ser Thr Cys Arg<br>385                       390                  395 | | 1561 |
| gct cag aac cag tgg tac tcc cag tgc ctc tgatgaggat ccgagctc<br>Ala Gln Asn Gln Trp Tyr Ser Gln Cys Leu<br>400                       405 | | 1609 |

<210> SEQ ID NO 15
<211> LENGTH: 409
<212> TYPE: PRT
<213> ORGANISM: Artificial
<220> FEATURE:
<223> OTHER INFORMATION: Synthetic Construct

<400> SEQUENCE: 15

Met His Ser Arg Asn Val Leu Ala Ala Ala Val Ala Leu Ala Gly Ala
1               5                  10                  15

Pro Ser Val His Ala Val Leu Arg Phe Ser Cys Ser Glu Leu Val Thr
                 20                  25                  30

Glu Arg Leu Asp Pro Leu Val Phe Pro Gly Ala Met Gln Ser Pro His
            35                  40                  45

Val His Gln Ile Val Gly Gly Asn Met Phe Asn Val Thr Met Asp Pro
 50                  55                  60

Asn Arg His Asn Ile Gly Glu Glu Ala Thr Cys Thr Thr Cys Thr Phe
 65                  70                  75                  80

Ser Glu Asp Phe Ser Asn Tyr Trp Thr Ala Ile Leu Tyr Phe Arg Ala
                 85                  90                  95

Arg Asn Gly Thr Leu Ile Arg Val Pro Gln Arg Pro Asn Ile Asp Phe
                100                 105                 110

Asp Gly Ala Arg Gly Gly Met Thr Val Tyr Tyr Thr Ala Thr Tyr
            115                 120                 125

Gln Asn His Lys Pro Thr Ala Phe Gln Pro Gly Phe Arg Met Ile Val
            130                 135                 140

Gly Asn Pro Met Tyr Arg Thr Gln Ala Glu Ala Ser Arg Tyr Arg Gln
145                 150                 155                 160

Met Thr Phe Thr Cys Leu Glu Thr Leu Ser Thr Arg Thr Gly Glu Thr
                165                 170                 175

Thr Glu Met Pro Lys Gln Pro Cys Arg Glu Gly Ile Met Ser Asn Val
            180                 185                 190

Arg Phe Pro Thr Cys Trp Asp Gly Lys Thr Leu Asp Pro Pro Asp His
            195                 200                 205

Ser Ser His Val Ala Tyr Pro Ser Ser Gly Thr Phe Glu Ser Gly Gly
210                 215                 220

Pro Cys Pro Ala Ser His Pro Val Arg Ile Pro Gln Leu Phe Tyr Glu
225                 230                 235                 240

Val Leu Trp Asp Thr Arg Arg Phe Asn Asp Arg Ser Leu Trp Pro Glu
                245                 250                 255

Asp Gly Ser Gln Pro Phe Val Trp Ser Tyr Gly Asp Tyr Thr Gly Tyr
            260                 265                 270

Gly Thr His Gly Asp Tyr Val Phe Gly Trp Lys Gly Asp Ser Leu Gln
            275                 280                 285

Arg Ala Met Asp Ala Asn Cys Asp Phe Tyr Cys Pro Gln Leu Lys Thr
290                 295                 300

Gln Ser Ile Ala Thr Gly Asn Gln Cys Arg Gln Asn Gln Lys Val Ala
305                 310                 315                 320

Glu Asn Ile Asp Gly Pro Phe Asp Arg Leu Pro Gly Asn Val Glu Ile
                325                 330                 335

Thr Gly Pro Gln Pro Gly Ala Ser Pro Asn Pro Gly Asn Gly Gly
            340                 345                 350

Gly Ser Thr Gln Thr Pro Val Gln Pro Thr Pro Val Pro Asn Pro Gly
            355                 360                 365

Asn Gly Gly Gly Cys Ser Val Gln Lys Trp Gly Gln Cys Gly Gly Gln
370                 375                 380

Gly Trp Ser Gly Cys Thr Val Cys Ala Ser Gly Ser Thr Cys Arg Ala
385                 390                 395                 400

Gln Asn Gln Trp Tyr Ser Gln Cys Leu
                405

<210> SEQ ID NO 16
<211> LENGTH: 445
<212> TYPE: PRT
<213> ORGANISM: Podospora anserina

<400> SEQUENCE: 16

```
Met Ala Asp Arg Pro Ser Arg Gly Glu Arg Ser Arg Val Val Ser Arg
1               5                   10                  15

Gln Gly Ala Ser Arg Ile Ser His Phe Ile Glu Leu Gly Ile Pro Asn
            20                  25                  30

Leu Thr Ile Lys Met His Ser Arg Asn Val Leu Ala Ala Ala Val Ala
        35                  40                  45

Leu Ala Gly Ala Pro Ser Val His Ala Val Leu Arg Phe Ser Cys Ser
    50                  55                  60

Glu Leu Val Thr Glu Arg Leu Asp Pro Leu Val Phe Pro Gly Ala Met
65                  70                  75                  80

Gln Ser Pro His Val His Gln Ile Val Gly Asn Met Phe Asn Val
            85                  90                  95

Thr Met Asp Pro Asn Arg His Asn Ile Gly Glu Ala Thr Cys Thr
            100                 105                 110

Thr Cys Thr Phe Ser Glu Asp Phe Ser Asn Tyr Trp Thr Ala Ile Leu
        115                 120                 125

Tyr Phe Arg Ala Arg Asn Gly Thr Leu Ile Arg Val Pro Gln Arg Pro
    130                 135                 140

Asn Ile Asp Phe Asp Gly Ala Arg Gly Gly Met Thr Val Tyr Tyr
145                 150                 155                 160

Thr Ala Thr Tyr Gln Asn His Lys Pro Thr Ala Phe Gln Pro Gly Phe
            165                 170                 175

Arg Met Ile Val Gly Asn Pro Met Tyr Arg Thr Gln Ala Glu Ala Ser
            180                 185                 190

Arg Tyr Arg Gln Met Thr Phe Thr Cys Leu Glu Thr Leu Ser Thr Arg
    195                 200                 205

Thr Gly Glu Thr Thr Glu Met Pro Lys Gln Pro Cys Arg Glu Gly Ile
210                 215                 220

Met Ser Asn Val Arg Phe Pro Thr Cys Trp Asp Gly Lys Thr Leu Asp
225                 230                 235                 240

Pro Pro Asp His Ser Ser His Val Ala Tyr Pro Ser Ser Gly Thr Phe
            245                 250                 255

Glu Ser Gly Gly Pro Cys Pro Ala Ser His Pro Val Arg Ile Pro Gln
            260                 265                 270

Leu Phe Tyr Glu Val Leu Trp Asp Thr Arg Arg Phe Asn Asp Arg Ser
        275                 280                 285

Leu Trp Pro Glu Asp Gly Ser Gln Pro Phe Val Trp Ser Tyr Gly Asp
    290                 295                 300

Tyr Thr Gly Tyr Gly Thr His Gly Asp Tyr Val Phe Gly Trp Lys Gly
305                 310                 315                 320

Asp Ser Leu Gln Arg Ala Met Asp Ala Asn Cys Asp Phe Tyr Cys Pro
            325                 330                 335

Gln Leu Lys Thr Gln Ser Ile Ala Thr Gly Asn Gln Cys Arg Gln Asn
            340                 345                 350

Gln Lys Val Ala Glu Asn Ile Asp Gly Pro Phe Asp Arg Leu Pro Gly
        355                 360                 365

Asn Val Glu Ile Thr Gly Pro Gln Pro Gly Ala Ser Asn Pro Asn
    370                 375                 380

Gly Asn Gly Gly Gly Ser Thr Gln Thr Pro Val Gln Pro Thr Pro Val
385                 390                 395                 400

Pro Asn Pro Gly Asn Gly Gly Cys Ser Val Gln Lys Trp Gly Gln
            405                 410                 415
```

```
Cys Gly Gly Gln Gly Trp Ser Gly Cys Thr Val Cys Ala Ser Gly Ser
                420                 425                 430

Thr Cys Arg Ala Gln Asn Gln Trp Tyr Ser Gln Cys Leu
            435                 440                 445

<210> SEQ ID NO 17
<211> LENGTH: 364
<212> TYPE: PRT
<213> ORGANISM: Podospora anserina

<400> SEQUENCE: 17

Met His Ile Arg Phe Leu Ala Val Ala Leu Thr Ala Ser Thr Ala
 1               5                  10                  15

Ser Ala Leu Leu Arg Phe Ser Cys Ser Gln Leu Val Thr Asp His Glu
                20                  25                  30

Ser Val Pro Leu Ser Leu Val Asn Pro Gly Met Ala Pro Ser Pro His
                35                  40                  45

Leu His Gln Ile Val Gly Gly Asn Ala Phe Asn Val Thr Met Asp Pro
        50                  55                  60

Ala Thr Pro Pro Pro Ser Gln Ala Thr Cys Thr Thr Cys Thr Phe Ala
65                  70                  75                  80

Asp Asp Phe Ser Asn Tyr Trp Thr Ala Ile Leu Tyr Phe Arg Ala Arg
                85                  90                  95

Asn Gly Ser Phe Ile Arg Val Pro Gln Lys Pro Asn Met Gly Phe Glu
                100                 105                 110

Ala Ala Asn Gly Gly Met Thr Val Tyr Tyr Thr Pro Phe Phe Thr Gly
                115                 120                 125

Arg Gly Gly Pro Gly Thr Val Thr Ala Phe Arg Pro Gly Phe Arg Met
        130                 135                 140

Leu Ile Gly Lys Gln Glu Tyr Arg Thr Arg Glu Glu Ala Ser Arg Phe
145                 150                 155                 160

Arg Gln Leu Thr Tyr Thr Cys Leu Gln Asn Ile Leu Thr Arg Thr Gly
                165                 170                 175

Glu Thr Leu Asp Met Pro Lys Arg Pro Cys Pro Ala Gly Ile Met Ser
                180                 185                 190

Asn Val Arg Phe Pro Thr Cys Trp Asp Gly Lys Asn Leu Asp Thr Pro
                195                 200                 205

Asp His Met Ala His Val Ala Tyr Pro Ala Ser Gly Thr Phe Glu Asn
        210                 215                 220

Asn Gly Pro Cys Pro Ala Ser His Pro Val Lys Ile Pro Gln Leu Phe
225                 230                 235                 240

Phe Glu Val Ile Trp Asp Thr Ser Lys Phe Asn Ala Lys Asp Leu Trp
                245                 250                 255

Pro Glu Asp Gly Ser Gln Pro Phe Val Trp Ser Gln Gly Asp Glu Thr
                260                 265                 270

Gly Phe Gly Asn His Gly Asp Tyr Val Phe Gly Trp Lys Asp Asn Ala
        275                 280                 285

Leu Gln Ile Ala Met Asp Ser Asn Cys Asp Arg Cys Pro Gln Leu Lys
290                 295                 300

Ser Gln Ser Leu Ala Thr Gly Asn Lys Cys Ile Gly Pro Leu His Val
305                 310                 315                 320

Arg Glu Lys Ile Asp Gly Cys Lys Leu Leu Pro Leu Phe Gln Ser Gln
                325                 330                 335

Asn Asp Val Ala Arg Ala Met Leu Thr Met Ser Val Gly Leu Asp Ala
```

```
              340                 345                 350
Ile Pro Gly Leu Thr Pro Asp Leu Lys Tyr Arg Asn
            355                 360

<210> SEQ ID NO 18
<211> LENGTH: 347
<212> TYPE: PRT
<213> ORGANISM: Podospora anserina

<400> SEQUENCE: 18

Met His Trp Ser Ser Ala Ala Leu Ala Leu Val Ala Pro Ala Ser
1               5                   10                  15

Ala Leu Leu Arg Phe Gly Cys Ser Gln Leu Val Val Glu Arg Thr Asp
            20                  25                  30

Pro Leu Val Asn Pro Gly Val Ala Pro Ser Pro His Leu His Gln Ile
            35                  40                  45

Ile Gly Gly Val Arg His Ser Asp Asn Arg Ala Arg Ile His Thr Asp
50                  55                  60

Thr Tyr Gln Asn Ala Phe Asn Ile Ser Met Glu Ala Ala Ala Gly Asp
65                  70                  75                  80

Ile Ala Lys Lys Ala Thr Cys Thr Thr Cys Gln Phe Ser Glu Asp Phe
                85                  90                  95

Ser Asn Tyr Trp Thr Ala Val Leu Phe Phe Lys Ala Arg Asn Gly Ser
            100                 105                 110

Val His Arg Val Pro Gln Ile Pro Asn Ala Gly Phe Glu Gly Ser Asn
            115                 120                 125

Gly Gly Met Thr Val Tyr Tyr Met Gln Asp Gly Leu Val Asn Tyr Gln
        130                 135                 140

Gln Thr Ser Lys Val Thr Ala Phe Lys Thr Gly Phe Arg Met Leu Ile
145                 150                 155                 160

Gly Glu Ala Met Tyr Arg Asn Arg Ala Gln Ala Ser Lys Phe Arg Gln
                165                 170                 175

Ile Thr Tyr Thr Cys Leu Lys Thr Phe Gly Thr Arg Tyr Pro Glu Thr
            180                 185                 190

Met Asp Phe Pro Lys Glu Pro Cys Asn Phe Gly Ile Met Ser Asn Val
        195                 200                 205

Arg Phe Pro Thr Cys Trp Asp Gly Lys Asn Leu Asp Ser Pro Asp His
210                 215                 220

Met Ala His Met Ser Tyr Pro Glu Ser Gly Thr Phe Glu Gly Gly Gly
225                 230                 235                 240

Pro Cys Pro Ala Ser His Pro Val Arg Val Pro Gln Leu Met Tyr Glu
                245                 250                 255

Val Ile Trp Asp Thr Arg Gln Phe Asn Asn Lys Asp Leu Trp Pro Glu
            260                 265                 270

Asp Gly Ser Gln Pro Phe Leu Thr Gly Phe Gly Ser His Gly Asp Tyr
        275                 280                 285

Met Phe Gly Trp Leu Asp Asp Ser Leu Gln Arg Ala Met Asp Ser Pro
290                 295                 300

Cys Tyr Val Asn Cys Pro Thr Leu Lys Ser Gln Ser Ile Ser Ala Met
305                 310                 315                 320

Asn Gln Cys Ser Val Pro Thr Val Val Asp Glu Pro Ile Asn Gly Cys
                325                 330                 335

Lys Trp Asn Leu Val Ser Cys Ser Cys Gly Ala
            340                 345
```

<210> SEQ ID NO 19
<211> LENGTH: 380
<212> TYPE: PRT
<213> ORGANISM: Podospora anserina

<400> SEQUENCE: 19

Met Arg Ala Ser Phe Ser Leu Leu Leu Pro Ile Leu Gly Leu Leu Ser
1               5                   10                  15

Thr Gly Ala His Ala Ile Val Arg Phe His Cys Ser Ala Leu Thr Val
            20                  25                  30

Gln Arg Leu Asp Pro Leu Val Asn Pro Gly Met Ile Pro Ser Thr His
        35                  40                  45

Val His Gln Ile Val Gly Gly Asp Ala Phe Asn Ala Ser Met Asp Pro
    50                  55                  60

Ser Leu Asp Leu Pro Glu Leu Ser Thr Thr Ser Cys Gln Phe Ala
65                  70                  75                  80

Glu Asp Phe Ser Asn Tyr Trp Thr Ala Val Leu Tyr Phe Lys Ala Lys
                85                  90                  95

Asn Gly Thr Tyr Lys Arg Val Pro Gln Leu Gly Asn Asn Gln Phe Glu
            100                 105                 110

Lys Ala Lys Gly Gly Leu Thr Ile Tyr Tyr Met Gln Asp Ala Ile Tyr
        115                 120                 125

Asp Arg Asn Gln Lys Ser Asn Val Gln Ala Phe Gln Pro Gly Phe Arg
    130                 135                 140

Met Phe Val Gly Asp Leu Asn Ala Arg Thr Ile Glu Glu Ala Ala Arg
145                 150                 155                 160

Phe Arg Gln Leu Thr Tyr Val Cys Met Asp Thr Trp Thr Ser Arg Ala
                165                 170                 175

Pro Glu Thr Met Ala Phe Pro Thr Arg Lys Cys Pro Glu Gly Ile Met
            180                 185                 190

Thr Ser Val Arg Phe Pro Thr Cys Trp Asp Gly Lys Asn Leu Asp Ser
        195                 200                 205

Pro Asp His Met Ala His Met Ser Tyr Pro Glu Tyr Gly Thr Phe Glu
    210                 215                 220

Ser Gly Gly Pro Cys Pro Ala Ser His Pro Val Arg Met Pro Gln Val
225                 230                 235                 240

Phe Tyr Glu Val Val Trp Asp Thr Lys Ile Phe Asn Asn Glu Glu Trp
                245                 250                 255

Pro Glu Asp Gly Ser Ser Pro Phe Val Trp Ser Phe Gly Asp Ala Thr
            260                 265                 270

Gly Phe Gly Thr His Gly Asp Tyr Leu Phe Gly Trp Lys Gly Asp Ala
        275                 280                 285

Leu Gln Arg Ile Leu Asp Ala Pro Cys Trp Phe Asn Thr Asn Cys Ala
    290                 295                 300

Lys Glu Ser Val Ser Val Asp Trp Tyr Trp Gly Trp Cys Leu Ser Pro
305                 310                 315                 320

Phe Cys Gly Asp Glu Arg Asp Ala Asp Asp Val Gly Ile Gln Asn Ser
                325                 330                 335

Pro Leu Gln Thr Ile Glu Gln Met Asn Ala Cys Thr Gln Pro Ser Met
            340                 345                 350

Val Asp Glu Asp Ile Asp Gly Trp Leu Asp Glu Leu Pro Gly Gly Trp
        355                 360                 365

Lys Ala Asp Tyr Gly His Gly His Gly Ser Arg Glu
    370                 375                 380

<210> SEQ ID NO 20
<211> LENGTH: 333
<212> TYPE: PRT
<213> ORGANISM: Podospora anserina

<400> SEQUENCE: 20

Met His Trp Thr Asn Val Leu Thr Ala Ala Ile Val Pro Leu Thr Gly
1               5                   10                  15

Val Arg Ala Ala Met Leu Arg Phe Ser Cys Ser Gln Leu Val Val Asp
            20                  25                  30

Arg Leu Asp Pro Leu Val Asn Pro Gly Gln Val Pro Ser Pro His Leu
        35                  40                  45

His Gln Ile Val Gly Gly Asn Ser Phe Asn Val Thr Met Asp Pro Asn
    50                  55                  60

Val Asn Asp Ile Ser Glu Ser Ser Thr Cys Thr Ser Cys Gln Phe Thr
65                  70                  75                  80

Glu Asp Phe Ser Asn Tyr Trp Thr Ala Val Leu Phe Phe Lys Ala Arg
                85                  90                  95

Asn Gly Thr Tyr Lys Arg Val Asn Thr Ile Gly Asn Gly Leu Gly Tyr
            100                 105                 110

Ser Ala Ser Asn Gly Gly Gln Thr Val Tyr Tyr Ile Ser Asn Gly Pro
        115                 120                 125

Val Thr Ala Phe Lys Pro Gly Phe Arg Met Val Val Gly Asn Pro Ala
    130                 135                 140

Phe Arg Thr Gln Ala Gln Ala Arg Thr Asn Pro Ala Leu Gln Phe Thr
145                 150                 155                 160

Cys Leu Ala Ser Pro Met Thr Arg Ser Gly Tyr Arg Tyr Asp Phe Pro
                165                 170                 175

Thr Asp Thr Cys Ala Gly Gly Ile Met Val Thr Val Arg Phe Pro Thr
            180                 185                 190

Cys Trp Asp Gly Lys Asn Thr Asp Ser Pro Asp His Gln Ser His Val
        195                 200                 205

Ala Tyr Pro Val Asn Arg Asn Cys Pro Ser Thr His Pro Ile Lys Ile
    210                 215                 220

Pro Glu Val Phe Tyr Glu Thr Tyr Trp Asp Thr Arg Pro Phe Asn Asn
225                 230                 235                 240

Lys Ala Leu Trp Pro Ala Asp Gly Ser Gln Pro Phe Val Trp Ser Phe
                245                 250                 255

Gly Asp Lys Thr Gly Tyr Gly Asn His Gly Asp Tyr Ile Phe Gly Trp
            260                 265                 270

Lys Gly Asp Ala Leu Gln Arg Ala Met Asp Ala Asn Cys Asn Ser Asp
        275                 280                 285

Leu Ile Gln Asp Arg Leu Asn Cys Pro Thr Leu Lys Ser Gln Ser Ile
    290                 295                 300

Val Asn Ala Asn Lys Cys Ser Ile Gln Arg Lys Val Lys Glu Asp Leu
305                 310                 315                 320

Asp Gly Trp Leu Glu Glu Leu Pro Gly Gly Gly Met Glu
                325                 330

<210> SEQ ID NO 21
<211> LENGTH: 343
<212> TYPE: PRT
<213> ORGANISM: Podospora anserina

<400> SEQUENCE: 21

Met Lys Ser Leu Phe Leu Ala Leu Pro Gly Leu Ala His Ala Ala Leu
1               5                   10                  15

Arg Phe Gly Cys Ser Thr Leu Thr Ile Glu Arg Leu Asp Pro Val Val
            20                  25                  30

Glu Pro Gly Asn Asn Pro Ser Ala His Val His Gln Val Val Gly Gly
            35                  40                  45

Asn Ala Phe Asn Ala Thr Val Asp Thr Ser Val Asp Val Gly Asn Arg
50                  55                  60

Ala Thr Cys Thr Thr Cys Ile Phe Ser Glu Asp Lys Ser Asn Tyr Trp
65                  70                  75                  80

Thr Ala Thr Leu Tyr Phe Arg Ala Arg Asn Gly Ser Tyr His Lys Val
                85                  90                  95

Pro Gln Tyr Pro Asn Ala Val Phe His Asp Gly Gln Val Gly Gly Met
                100                 105                 110

Thr Ile Tyr Tyr Thr Gln Gln Asp Phe Trp Asp Asn Gly Asn Gln Lys
                115                 120                 125

Ile Thr Ser Phe Pro Pro Gly Phe Arg Met Thr Val Gly Ser Pro Thr
130                 135                 140

Thr Glu Thr Arg Glu Gln Ala Gln Gln Tyr Lys Gly Leu Arg Tyr Thr
145                 150                 155                 160

Cys Leu Gln Asp Ile Leu Thr Arg Gly Ser Glu Thr Tyr Asp Phe Pro
                165                 170                 175

Lys Gln Pro Cys Pro Ala Gly Ile Met Ala Ile His His Phe Pro Ala
                180                 185                 190

Cys Trp Asp Gly Lys Asn Leu Asp Ser Pro Asp His Gln Ser His Met
                195                 200                 205

Phe Leu Thr Gly His Gly Gly Phe Arg Val Ala Asp Pro Cys Pro Ala
            210                 215                 220

Ser His Pro Val Arg Met Pro Gln Val Ala Tyr Glu Thr Met Trp Asp
225                 230                 235                 240

Thr Ser Val Phe Asn Asp Lys Asp Leu Trp Pro Glu Asp Gly Ser Gln
                245                 250                 255

Pro Phe Ile Trp Ser Thr Gly Asp Thr Lys Gly Tyr Ser Thr His Ala
                260                 265                 270

Asp Tyr Leu Phe Gly Trp Glu Gly Asp Ser Leu Gln Arg Ala Met Asp
            275                 280                 285

Ser Asn Cys Phe Phe Gln Arg Cys Ser Leu Gly Lys Tyr Pro Glu Gly
            290                 295                 300

Val Leu Lys Val Gln Thr Pro Glu Glu Gln Asn Ala Cys Lys Ile Glu
305                 310                 315                 320

Thr Thr Val Lys Glu Pro Val Asp Gly Cys Lys Phe Ala Pro Leu Gln
                325                 330                 335

Ser Leu Phe Glu Ala Lys Ser
            340

<210> SEQ ID NO 22
<211> LENGTH: 339
<212> TYPE: PRT
<213> ORGANISM: Podospora anserina

<400> SEQUENCE: 22

Met Lys Ser Ser Leu Leu Ala Thr Ala Ala Leu Trp Val Arg His
1               5                   10                  15

Val Ser Gly Gln Ala Ala Met Met Arg Phe Gln Cys Ser Gln Leu Val

```
            20                  25                  30
Ile Glu Arg Leu Asp Pro Leu Val Asn Pro Gly Ala Leu Gln Ser Pro
            35                  40                  45
His Leu His Gln Ile Val Gly Gly Asn Ser Phe Asn Ala Ser Met Pro
    50                  55                  60
Pro Gly Glu Tyr Asp Pro Ser Thr Gln Ser Thr Cys Thr Thr Cys Ser
65                  70                  75                  80
Phe Ser Glu Asp Phe Ser Asn Tyr Trp Thr Ala Asn Val Tyr Phe Lys
                85                  90                  95
Ala Lys Asn Gly Ser Phe Lys Arg Val Pro Gln Met Val Asn Leu Gly
                100                 105                 110
Leu Arg Gly Lys Gly Val Thr Val Tyr Tyr Ile Pro Pro Tyr Asp
            115                 120                 125
Gly Lys Thr Lys Val Thr Ala Phe Lys Pro Gly Phe Arg Met Leu Val
            130                 135                 140
Gly Asp Pro Ser Leu Arg Asn Gln Arg Gly Met Gln Lys Gln Ile Cys
145                 150                 155                 160
His Arg Cys Glu His Asn Ile Glu Gln Asn Pro Phe Gly Gly Ala Pro
                165                 170                 175
Cys Thr Gly Glu Asp Thr Ala Ser Phe Pro Asn Lys Ile Cys Pro Gly
                180                 185                 190
Gly Ile Arg Thr Thr Ile Thr Phe Pro Thr Cys Trp Asp Gly Lys Asn
                195                 200                 205
Val Asp Ser Pro Asp His Lys Ser His Val Ser Tyr Pro Gln Thr Gly
            210                 215                 220
Ser Phe Glu Ser Thr Gly Pro Cys Pro Ala Ser His Pro Val Arg Leu
225                 230                 235                 240
Pro Gln Leu Met Tyr Glu Val Met Trp Asp Thr Arg Pro Phe Asn Asp
                245                 250                 255
Lys Ser Ile Trp Pro Glu Lys Gly Gln Pro Leu Val Tyr Ser Met Gly
                260                 265                 270
Asp Gly Thr Gly Tyr Gly Gln His Gly Asp Tyr Val Phe Gly Trp Lys
            275                 280                 285
Gly Asp Ser Leu Gln Arg Ala Leu Asp Ala Arg Cys Ser Gly Asp Arg
            290                 295                 300
Cys Ser Gln Leu Lys Thr Gln Ser Ala Glu Gln Ala Val Ala Cys Leu
305                 310                 315                 320
Lys Gln Gln Thr Ile Ala Glu Glu Thr Glu Gly Cys Lys Phe Asn Leu
                325                 330                 335
Ala Arg Gly

<210> SEQ ID NO 23
<211> LENGTH: 343
<212> TYPE: PRT
<213> ORGANISM: Podospora anserina

<400> SEQUENCE: 23

Met Lys Ser Thr Leu Leu Ala Ala Ala Leu Leu Gln Gly Ala Ala Gln
1               5                   10                  15
Ala Gln Gln Met Ile Arg Phe Gly Cys Ser Gln Leu Val Val Ser Arg
                20                  25                  30
Leu Asp Pro Leu Val Asn Pro Gly Leu Glu Gln Ser Pro His Val His
            35                  40                  45
Gln Ile Val Gly Gly Asn Ser Phe Asn Ala His Met Pro Phe Glu Gln
```

```
                50                  55                  60
Gly Phe Asp Leu Val Lys Asn Ser Thr Cys Thr Ser Cys Thr Phe Ser
 65                  70                  75                  80

Glu Asp Phe Ser Asn Tyr Trp Thr Ala Val Leu Tyr Phe Lys Ala Arg
                 85                  90                  95

Asn Gly Thr Tyr Lys Arg Val Arg Gln Phe Pro Asn Val Gly Leu Arg
            100                 105                 110

Thr Asp Gly Gly Val Thr Val Tyr Tyr Ile Pro Pro Tyr Asp Gly Lys
            115                 120                 125

Thr Thr Val Thr Ala Phe Lys Pro Gly Phe Arg Met Leu Val Gly Asp
            130                 135                 140

Ala Gly Leu Arg Gln Asn Arg Gly Met Gln Lys Gln Leu Cys His Arg
145                 150                 155                 160

Cys Leu Gly Ala Gly Tyr Asp Arg Gly Ala Pro Cys Thr Gly Ser
                165                 170                 175

Asp Ser Thr Thr Leu Pro Asn Lys Phe Cys Asp Gly Gly Ile Arg Thr
                180                 185                 190

Thr Ile Thr Phe Pro Thr Cys Trp Asp Gly Lys Asn Leu Asp Ala Pro
                195                 200                 205

Asp His Lys Ser His Val Ala Tyr Pro Gln Thr Gly Ser Phe Glu Ser
            210                 215                 220

Thr Gly Pro Cys Pro Ser Ser His Pro Val Arg Leu Pro Gln Leu Met
225                 230                 235                 240

Tyr Glu Val Met Trp Asp Thr Gln Ala Phe Asn Asp Lys Ser Leu Trp
                245                 250                 255

Pro Glu Asp Gly Ser Gln Pro Phe Val Trp Ser Thr Gly Asp Gly Leu
                260                 265                 270

Gly Tyr Ser Gln His Gly Asp Tyr Val Phe Gly Trp Lys Gly Asp Ser
                275                 280                 285

Leu Gln Arg Ala Leu Asp Ala Arg Cys Ser Asn Ala Val Cys Lys Glu
            290                 295                 300

Leu Lys Thr Gln Ser Ser Glu Glu Ala Met Arg Cys Thr Gln Pro Gln
305                 310                 315                 320

Asn Val Pro Glu Asn Val Asp Gly Cys Lys Phe Ala Ser Leu Gly Asp
                325                 330                 335

Ala Gly Glu Asp Tyr Ala Cys
            340

<210> SEQ ID NO 24
<211> LENGTH: 356
<212> TYPE: PRT
<213> ORGANISM: Podospora anserina

<400> SEQUENCE: 24

Met Lys Trp Asn Ser Leu Ala Ala Leu Gly Phe Ala Ala Pro Ala Gln
 1                5                  10                  15

Ala Tyr Leu Arg Phe Gly Cys Ala Thr Leu Thr Val Gln Arg Leu Asp
                 20                  25                  30

Pro Ile Val Glu Pro Gly Lys Val Pro Ser Ser His Val His Gln Ile
             35                  40                  45

Ile Gly Gly Asn Ala Phe Asn Ala Thr Met Asp Pro Lys Val Asp Ile
         50                  55                  60

Ala Glu Lys Ala Thr Cys Thr Thr Cys Ser Phe Arg Trp Val Ser Leu
 65                  70                  75                  80
```

```
Pro Leu Ile Glu Cys Arg His Leu His Thr Arg Leu Thr Gln Phe Thr
                85                  90                  95

Ser Glu Asp Phe Thr Asn Tyr Trp Thr Ala Val Met Tyr Phe Lys Ala
            100                 105                 110

Arg Asn Gly Ser Tyr Lys Arg Val Gly Gln Tyr Pro Asn Ala Leu Leu
            115                 120                 125

Gly Ser Leu Thr Gly Gly Met Thr Val Tyr Tyr Leu Gln Gln Asp Phe
            130                 135                 140

Asn Ser Asn Gly Lys Gln Lys Ile Thr Ala Phe Lys Pro Gly Phe Arg
145                 150                 155                 160

Met Thr Val Gly Ser Pro Thr Ala Thr Asn Gly Asn Pro Gly Leu
                165                 170                 175

Arg Tyr Thr Cys Leu Lys Asp Val Met Thr Arg Phe Pro Glu Thr Ala
            180                 185                 190

Asp Phe Pro Lys Glu Pro Cys Pro Ala Gly Ile Met Ala Ile His His
            195                 200                 205

Phe Pro Ala Cys Trp Asp Gly Lys Asn Leu Asp Ser Pro Asn His Gln
            210                 215                 220

Asp His Met Tyr Asn Thr Gly Lys Gly Ala Phe Thr Asn Ala Gly Pro
225                 230                 235                 240

Cys Pro Ser Ser His Pro Val Arg Met Pro Gln Val Ala Leu Glu Thr
                245                 250                 255

Met Trp Asp Thr Thr Pro Phe Asn Asn Lys Asp Leu Trp Pro Thr Asp
            260                 265                 270

Gly Ser Gln Pro Phe Val Trp Ser Tyr Gly Asp Ser Lys Gly Tyr Gly
            275                 280                 285

Thr His Ala Asp Tyr Leu Phe Gly Trp Lys Gly Asp Ser Leu Gln Arg
            290                 295                 300

Ala Met Asp Ser Thr Pro Leu Leu Ser Asn Gly Ile Lys Ser Gln Ser
305                 310                 315                 320

Val Ala Gln Ala Asn Asn Cys Lys Leu Gln Thr Thr Thr Val Lys Glu
                325                 330                 335

Asn Ile Asp Gly Cys Lys Phe Ser Pro Leu Asp Cys Leu Leu Cys Arg
            340                 345                 350

Glu Ser Ser Asp
            355

<210> SEQ ID NO 25
<211> LENGTH: 358
<212> TYPE: PRT
<213> ORGANISM: Podospora anserina

<400> SEQUENCE: 25

Met Lys Trp Leu Ala Leu Ser Ala Leu Ile Ala Pro Ser Gln Ala Ala
1               5                   10                  15

Leu Arg Phe Gly Cys Ser Thr Leu Thr Ile Gln Arg Leu Asp Pro Leu
            20                  25                  30

Val Glu Pro Gly Ala Leu Pro Ser Ala His Leu His Gln Ile Val Gly
            35                  40                  45

Gly Asp Ala Phe Asn Ala Ser Met Ser Gly Asp Ile Gly Glu Gln Gly
            50                  55                  60

Thr Cys Thr Thr Cys Thr Phe Ser Glu Asp Phe Ser Asn Tyr Trp Thr
65                  70                  75                  80

Ala Val Met Phe Phe Lys His Pro Asn Gly Thr Tyr Lys Arg Val Pro
                85                  90                  95
```

```
Ile Met Gln Asn Thr Ala Leu Pro Asn Gly Ile Asn Gly Gly Met Thr
            100                 105                 110

Val Tyr Tyr Thr Gln Gln Asp Phe Asn Ser Asn Gly Asn Val Lys Ile
            115                 120                 125

Thr Ser Phe Pro Pro Gly Phe Arg Met Val Val Gly Asn Pro Thr Thr
            130                 135                 140

Thr Ser Leu Ser Gly Ser Arg Ala Asn Val Gly Leu Lys Phe Val Cys
145                 150                 155                 160

Leu Glu Asn Lys Gly Thr Arg Phe Pro Glu Leu Ser Asp Phe Pro Thr
                165                 170                 175

Lys Pro Cys Arg Gly Gly Ile Met Thr Val His His Phe Pro Ala Cys
            180                 185                 190

Trp Asp Gly Lys Asn Val Asp Ser Pro Asp His Gln Ser His Met Tyr
            195                 200                 205

Asn Thr Gly Lys Glu Ala Phe Gln Asn Ala Gly Pro Cys Pro Ala Ser
            210                 215                 220

His Pro Val Arg Met Pro Gln Val Ala Tyr Glu Thr Leu Trp Asp Thr
225                 230                 235                 240

Thr Gln Phe Asn Ser Met Trp Pro Ser Gly Gly Ala Asn Pro Phe Thr
                245                 250                 255

Leu Ser Tyr Thr Asp Ser Lys Gly Tyr Gly Thr His Ala Asp Tyr Leu
            260                 265                 270

Phe Gly Trp Lys Gly Asp Ser Leu Gln Arg Ala Met Asp His Ser Cys
            275                 280                 285

Met Phe Asn Ala Cys Glu Asn Gly Arg Pro Leu Lys Ser Gln Asn Val
            290                 295                 300

Ala Ala Met Asn Arg Cys Thr Ile Lys Lys Ile Val Asn Glu Asp Thr
305                 310                 315                 320

Gly Asp Asn Cys Glu Phe Cys Cys His Asp Phe Met Phe Gly Glu Asp
                325                 330                 335

Glu Lys Leu Thr Gly Val Ser Ser Thr Thr Gly Ile Lys Ala Met Pro
            340                 345                 350

Gly Gln Thr Ala Ala Ser
            355

<210> SEQ ID NO 26
<211> LENGTH: 384
<212> TYPE: PRT
<213> ORGANISM: Podospora anserina

<400> SEQUENCE: 26

Met Val Phe Thr Phe Ile Phe Ala Gly Leu Leu Leu Gln Val Thr
1               5                   10                  15

Val Thr Ser Gln Asn Val Ile Val Gly Lys Leu Leu Arg Phe Ala Cys
                20                  25                  30

Ser Gln Leu Val Ile Glu Arg Thr Asp Pro Leu Val Asn Pro Gly Leu
            35                  40                  45

Ser Pro Ser Pro His Thr His Gln Ile Val Gly Gly Asn Ser Phe Asn
        50                  55                  60

Val Thr Met Asn Pro Ser Glu Met Glu Pro Arg Ala Ser Thr Cys
65                  70                  75                  80

Thr Thr Cys Thr Tyr Ser Glu Asp Phe Ser Asn Tyr Trp Thr Ala Ser
                85                  90                  95

Leu Tyr Phe Arg Ser Pro Glu Asn Gly Ser Phe Lys Leu Val Pro Gln
```

```
            100                 105                 110
Arg Pro Asn Phe Val Gly Met Asp Gly Val Arg His Pro Val Gly Gly
        115                 120                 125

Gly Ile Thr Val Tyr Tyr Met Thr Ser Val Phe Gly Ser Thr Ser Gly
    130                 135                 140

Asn Gly Lys Val Thr Ala Phe Pro Pro Gly Phe Arg Met Leu Ala Gly
145                 150                 155                 160

Ser Pro Asp Ile Thr Ser Lys Asp Arg Thr Phe Pro Gly Ile Cys His
                165                 170                 175

Arg Cys Asn Gly Asn Thr Thr Gly Phe Thr Pro Cys Asp Ser Ala Asp
            180                 185                 190

Ser Ser Glu Leu Pro Thr Lys Val Cys Pro Gly Gly Ile Arg Gly Ser
        195                 200                 205

Val Ile Phe Pro Ser Cys Trp Asp Gly Lys Asn Leu Asp Ser Pro Asp
    210                 215                 220

His Ser Ser His Val Ala Tyr Ser Pro Val Gly Gly Lys Leu Ala
225                 230                 235                 240

Gly Gln Ala Cys Pro Glu Thr His Pro Val Arg Ile Pro Gln Leu Met
                245                 250                 255

Tyr Glu Met Leu Trp Asp Thr Ser Gln Phe Asn Ala Pro Ala Tyr Phe
            260                 265                 270

Asp Glu Thr Ala Lys Arg Gln Pro Phe Val Tyr Ser Phe Gly Asp Gly
        275                 280                 285

Ile Gly Tyr Gly Gln His Gly Asp Tyr Ile Phe Gly Trp Lys Gly Asp
    290                 295                 300

Ala Leu Gln Arg Gly Met Asp Ala Val Leu Gly Asp Asp Cys Val Asn
305                 310                 315                 320

Asp Arg Cys His Ala Leu Glu Phe Gln Ser Pro Ala Glu Gly Val Ala
                325                 330                 335

Cys Ala Lys Pro Thr Gln Val Glu Gly Glu Ile Val Gly Arg Gly Gly
            340                 345                 350

Glu Cys Lys Phe Met Arg Val Met Arg Ile Leu Gln Val Val Leu Ile
        355                 360                 365

Pro Pro Gly Leu Gln Thr Leu Pro Gly Asn Pro His Leu Arg Gln Ala
    370                 375                 380
```

<210> SEQ ID NO 27
<211> LENGTH: 359
<212> TYPE: PRT
<213> ORGANISM: Podospora anserina

<400> SEQUENCE: 27

```
Met Tyr Trp Lys Ala Leu Ala Leu Ala Ala Val Asn Gly Gln Gly
1               5                  10                  15

Leu Asn Gly Leu Asn His Leu Arg Phe Gly Cys Ser Gln Leu Thr Val
            20                  25                  30

Glu Arg Leu Asp Pro Leu Val Asn Pro Gly Glu Phe Pro Thr Pro His
        35                  40                  45

Met His Gln Ile Ile Gly Gly Asn Ala Phe Asn Ala Ser Met Pro Tyr
    50                  55                  60

Asn Thr Asp Ile Ala Asn Leu Ala Thr Cys Thr Thr Cys Gly Pro Ala
65                  70                  75                  80

Asp Asp Phe Ser Asn Tyr Trp Thr Ala Asn Val Tyr Phe Arg Ala Arg
                85                  90                  95
```

```
Asn Gly Ser Tyr Lys Arg Val Pro Gln Ala Pro Asn Arg Phe Leu Phe
            100                 105                 110

Asn Asp Arg Phe Thr Thr Gln Ile Thr Gly Gly Ala Val Val Tyr Tyr
        115                 120                 125

Pro Ser Leu Trp Ala Glu Phe Asp Ile Ala Pro Arg Ala Lys Thr Val
    130                 135                 140

Thr Ala Phe Lys Pro Gly Phe Arg Met Phe Val Gly Asp Val Asn Arg
145                 150                 155                 160

Arg Glu Pro Lys Tyr Lys Met Gln Ser Cys Phe Arg Cys Tyr Ser Gly
                165                 170                 175

Pro Asn Phe Gly Gly Asp Asp Met Ala Pro Cys Ala Asp Ser Arg Leu
            180                 185                 190

Asp Phe Glu Gly Phe Pro Thr Gly Pro Cys Leu Gly Gly Ile Arg Ser
        195                 200                 205

Asn Val Leu Tyr Pro Thr Cys Trp Asp Gly Lys Asn Leu Asp Thr Pro
    210                 215                 220

Asn His Lys Asp His Val Ala Tyr Pro Thr Ser Gly Pro Ser Asn Phe
225                 230                 235                 240

Leu Ser Thr Gly Asn Cys Pro Ala Ser His Pro Val Lys Ile Pro Gln
                245                 250                 255

Leu Met Leu Glu Ile Val Trp Asp Thr Thr Lys Phe Asn Asn Lys Ala
            260                 265                 270

Glu Trp Pro Ala Asp Gly Ser Gln Pro Phe Val Leu Ser Thr Gly Asp
        275                 280                 285

Lys Thr Gly Tyr Gly Gln His Gly Asp Tyr Val Phe Gly Trp Lys Gly
    290                 295                 300

Asp Ala Leu Gln Arg Ala Met Asp Ala Asn Gly Cys Phe Ser Ala Thr
305                 310                 315                 320

Cys Gly Asn Gln Lys Ser Gln Asp Ile Ala Thr Ala Asn Lys Cys Gln
                325                 330                 335

Ile Lys Lys Thr Val Arg Glu Asp Val Glu Gly Trp Phe Asn Ser Leu
            340                 345                 350

Pro Gly Ser Pro Met Ala Ala
        355

<210> SEQ ID NO 28
<211> LENGTH: 362
<212> TYPE: PRT
<213> ORGANISM: Podospora anserina

<400> SEQUENCE: 28

Met Leu Leu Arg Ala Thr Ala Leu Ala Leu Gly Ala Thr Leu Thr Gly
1               5                   10                  15

His Leu Ala Ser Ala Gln Pro Pro Gly Ile Val Ile Pro Pro Met Met
                20                  25                  30

Arg Phe Ala Cys Ser Gln Leu Val Val Asp Arg Ile Asp Pro Leu Val
            35                  40                  45

Asn Pro Gly Ser Val Pro Ser Pro His Leu His Gln Ile Val Gly Gly
        50                  55                  60

Asn Ser Phe Arg Pro Asp Met Thr His Pro Asn His Asp Leu Val Ser
65                  70                  75                  80

Asn Ser Thr Cys Thr Ser Cys Thr Phe Thr Glu Asp Leu Ser Asn Tyr
                85                  90                  95

Trp Thr Ala Val Leu Phe Phe Arg Ala Arg Asn Gly Thr Tyr Lys Arg
            100                 105                 110
```

Val Pro Gln His Gln Glu Gly Leu Arg Gly Asn Gly Gly Ile Thr
            115                 120                 125

Val Tyr Tyr Ile Pro Ser Thr Thr Ile Thr Thr Pro Gly Thr Val Lys
130                 135                 140

Ala Phe Lys Pro Gly Phe Arg Met Leu Val Gly Asp Ala Ala Lys Lys
145                 150                 155                 160

Glu Gly Pro Asp Ala Gly Pro Ala Pro Val Lys Val Cys His Arg Cys
                165                 170                 175

Met Pro Glu Ser Gly Asp Asn Arg Asn Leu Asn Cys Ala Ser Pro Asp
            180                 185                 190

Thr Glu Lys Leu Pro Ser Lys Pro Cys Val Gly Ile Arg Ser Val
            195                 200                 205

Ile Thr Phe Pro Thr Cys Trp Asp Gly Val Asn Leu Asp Ser Pro Asp
210                 215                 220

His Met Ser His Val Ala Tyr Ala Lys Gly Ala Gly Ala Tyr Asp Val
225                 230                 235                 240

Gly Pro Thr Gly Asn Cys Pro Asp Thr His Pro Val Val Ile Pro Gln
                245                 250                 255

Val Met Tyr Glu Val Arg Trp Arg Thr Asp Leu Phe Ser Asp Pro Asp
            260                 265                 270

Leu Trp Pro Glu Asp Gly Ser Gln Pro Phe Val Trp Ser Thr Gly Asp
            275                 280                 285

Glu Lys Gly Phe Ser Gln His Gly Asp Tyr Val Phe Gly Trp Lys Asp
290                 295                 300

Asp Ala Leu Gln Arg Ala Met Asp Ala Arg Cys Thr Met Asp Val Cys
305                 310                 315                 320

Asp Val Leu Glu Thr Gln Thr Pro Glu Glu Ala Val Lys Cys Thr Val
                325                 330                 335

Pro Pro Arg Val Asp Glu Asp Tyr Glu Gly Cys Lys Phe Ser Pro Asp
                340                 345                 350

Pro Arg Leu Arg Phe Gly Asp Lys Leu Cys
            355                 360

<210> SEQ ID NO 29
<211> LENGTH: 330
<212> TYPE: PRT
<213> ORGANISM: Podospora anserina

<400> SEQUENCE: 29

Met Leu Arg Phe Gly Cys Ser Gln Val Val Ile Glu Arg Leu Asp Pro
1               5                   10                  15

Leu Val Asn Pro Gly Gln Asn Pro Ser Ser His Met His Gln Ile Val
            20                  25                  30

Gly Gly Asn Ala Phe Ser Ala Ser Met Pro Leu Glu Asp Ile Ser Ala
        35                  40                  45

Leu Ser Thr Cys Thr Thr Cys His Phe Gln Glu Asp His Ser Asn Tyr
    50                  55                  60

Trp Thr Ala Asn Leu Tyr Phe Arg Ala Arg Asn Gly Thr Tyr Lys Arg
65                  70                  75                  80

Val Pro Gln Met Ala Asn Glu Phe Asn Thr Gly Asp Asn Gly Ile
                85                  90                  95

Thr Val Tyr Tyr Thr Ser Pro Ala Pro Asn Ala Thr Thr Ala Phe Lys
                100                 105                 110

Pro Gly Phe Arg Met Leu Ala Gly Asp Val Asn Leu Arg Lys Ser Glu

```
              115                 120                 125
Gly Leu Gly Arg Asn Met Gln Gln Cys Tyr Arg Cys Tyr Thr Lys Glu
130                 135                 140

Asn Phe Gly Gly Ser Met Tyr Ser Pro Cys Met Asp Pro Val Tyr Asp
145                 150                 155                 160

Thr Asp His Leu Pro Lys Ile Pro Cys Pro Gly Gly Ile Arg Ser Asn
                165                 170                 175

Ile Ile Phe Pro Leu Cys Trp Asp Gly Val Asn Leu Asp Ser Pro Asn
                180                 185                 190

His Lys Asp His Val Ala His Pro Ile Thr Gly Pro Thr Ser Phe Ser
                195                 200                 205

Val Val Gly Gly Glu Cys Pro Lys Ser His Pro Val Lys Ile Pro Gln
210                 215                 220

Val Met Tyr Glu Val Met Trp Asp Thr Arg Pro Phe Asn Asn Pro Glu
225                 230                 235                 240

Asp Trp Pro Glu Asp Gly Ser Gln Pro Leu Val Leu Ser Asn Gly Asp
                245                 250                 255

Thr Thr Gly Tyr Gly Gln His Gly Asp Tyr Val Phe Gly Trp Glu Lys
                260                 265                 270

Asp Ser Leu Gln Val Ala Met Asp Thr Gly Cys Tyr Leu Arg Asn Cys
                275                 280                 285

Ser Ser Leu Thr Glu Leu Pro Pro Lys Val Lys Asn Gln Cys Gln Val
290                 295                 300

Pro Val Ser Ala Thr Val Asp Gly Asp Leu Asp Glu Cys Lys Leu Pro
305                 310                 315                 320

Pro His Leu Phe Phe Phe Phe Phe Val Phe
                325                 330

<210> SEQ ID NO 30
<211> LENGTH: 366
<212> TYPE: PRT
<213> ORGANISM: Podospora anserina

<400> SEQUENCE: 30

Met Leu Leu Leu Leu Ser Leu Leu Ser Thr Leu Gly Leu Ala Ala Pro
1               5                   10                  15

Gln Leu Gly Thr Ser Pro Trp Gly Pro Asn Val Ser Ser Thr Met Leu
                20                  25                  30

Arg Phe Gly Cys His Gln Leu Val Ile Asp Arg Ile Asp Pro Leu Val
                35                  40                  45

Asn Pro Gly Ser Leu Pro Ser Pro His Leu His Gln Ile Val Gly Gly
50                  55                  60

Asn Ala Phe Asp Ile Ser Met Pro His Asn Thr Asp Ile Ser Ser Leu
65                  70                  75                  80

Ala Asn Cys Thr Thr Cys Ser Tyr Ser Glu Asp Leu Ser Asn Tyr Trp
                85                  90                  95

Thr Ala Asn Leu Tyr Phe Arg Ala Arg Asn Gly Ser Tyr Lys Arg Val
                100                 105                 110

Pro Gln Ile Pro Asn Arg Leu Leu Phe Gly Asp Asp Phe Thr Thr Lys
                115                 120                 125

Thr Asp Gly Gly Phe Val Val Tyr Val Ser Gly Ile Gly Asp
130                 135                 140

Val Thr Ala Phe Arg Pro Gly Phe Arg Met Leu Val Gly Asp Ala Gly
145                 150                 155                 160
```

```
Arg Arg Glu Pro Gln Gly Leu Arg Asn Gln Thr Cys Phe Arg Cys Tyr
            165                 170                 175

Thr Gly Pro Asp Phe Gly Asp Asp Lys Ala Pro Cys Val Asp Asp
        180                 185                 190

Ala Val Asp Phe Glu Gly Leu Pro Asn Lys Met Cys Trp Gly Ile Arg
            195                 200                 205

Ser Asn Val Leu Tyr Pro Thr Cys Trp Asp Gly Lys Asn Leu Asp Ser
210                 215                 220

Pro Asp His Lys Ser His Val Ala Tyr Pro Val Glu Thr Gly Pro His
225                 230                 235                 240

Thr Phe Thr Gly Leu Gly Thr Gly Gln Cys Pro Glu Ser His Pro
                245                 250                 255

Val Arg Ile Pro Gln Leu Met Leu Glu Ile Val Trp Asp Thr Ser Leu
            260                 265                 270

Phe Asn Asp Pro Asp Glu Trp Pro Glu Asp Gly Ser Gln Pro Phe Val
        275                 280                 285

Leu Ser Thr Gly Asp Thr Thr Tyr Gly Gln His Gly Asp Tyr Val
290                 295                 300

Phe Gly Trp Lys Gly Asp Ser Leu Gln Arg Ala Met Asp Gly Val Cys
305                 310                 315                 320

Phe Gly Ala Asn Cys His Val Leu Glu Ser Gln Ser Leu Glu Glu Ala
                325                 330                 335

Lys Arg Cys Ser Val Ser Ser Arg Val Gly Glu Val Asp Gly Trp
                340                 345                 350

Leu Asp Thr Leu Pro Gly Asn Pro Asp Ile Arg Glu Lys Lys
            355                 360                 365

<210> SEQ ID NO 31
<211> LENGTH: 323
<212> TYPE: PRT
<213> ORGANISM: Podospora anserina

<400> SEQUENCE: 31

Gln Ser Leu Val Asn Pro Gly Val Leu Gly Thr Pro His Ile His Gln
1               5                   10                  15

Ile Val Gly Gly Asn Ser Phe Asn Thr Thr Met Asp Pro Leu Thr His
                20                  25                  30

Asp Pro Ala Thr Leu Ser Thr Cys Thr Thr Cys Thr Phe Thr Asp Asp
            35                  40                  45

Phe Ser Asn Tyr Trp Thr Ala Ile Met Tyr Phe Arg Ala Arg Asn Asn
    50                  55                  60

Thr Tyr His Arg Val Pro Gln Leu Gly Ser Leu Phe His Glu Ser Ala
65                  70                  75                  80

Arg Glu Gly Gly Met Thr Ile Tyr Tyr Phe Pro Gln Phe Val Asn Pro
                85                  90                  95

Lys Pro Gly Thr Ile Lys Ala Phe Ala Pro Gly Phe Arg Met Arg Val
            100                 105                 110

Gly His Pro Asp Arg Val His Pro Val Asn Glu Ser Gly His Pro Arg
        115                 120                 125

Pro Glu His Gln Pro Thr Ala Leu Tyr Asp Gly Ile Tyr Thr Cys
    130                 135                 140

Leu Glu Thr Glu Gly Thr Arg Phe Thr Asn Leu Thr Ser Ser Phe Pro
145                 150                 155                 160

Pro His Pro Cys Pro Tyr Gly Ile Leu Thr Thr Leu Pro Phe Pro Pro
                165                 170                 175
```

```
Cys Trp Asp Gly Lys Asn Leu Asp Ser Pro Asp His Gln Ser His Val
            180                 185                 190

Ser Phe Ala Glu Gly Gly Thr Val Gly Tyr Thr Gln Gly Gly Lys Cys
            195                 200                 205

Pro Ala Ser His Pro Val Met Ile Pro Gln Ile Met Leu Glu Thr Arg
            210                 215                 220

Trp Asp Thr Thr Leu Phe Asn Asp Pro Asp Leu Trp Pro Glu Glu Gln
225                 230                 235                 240

Gly Lys Gln Pro Phe Leu Trp Ser Phe Gly Asp Gly Val Gly Tyr Gly
            245                 250                 255

His His Gly Asp Tyr Val Phe Gly Trp Arg Gly Asn Ser Leu Gln Arg
            260                 265                 270

Thr Phe Asp Arg Val Asp Cys Ser Gly Asp Gln Ile Cys Gly Leu Pro
            275                 280                 285

Val Gln Thr Ile Glu Arg Ala Asn Gly Cys Phe Gly Glu Arg Arg Val
            290                 295                 300

Val Glu Gly Val Asp Gly Trp Leu Gly Glu Met Pro Gly Gly Val Val
305                 310                 315                 320

Val Arg Asp

<210> SEQ ID NO 32
<211> LENGTH: 345
<212> TYPE: PRT
<213> ORGANISM: Podospora anserina

<400> SEQUENCE: 32

Met Leu Trp Thr Ser Leu Phe Leu Ala Ala Leu Ala Glu Ala Ala Pro
1               5                   10                  15

Lys Ala Ser Pro Asn Pro Gln Phe Gly Gly Pro Gly Gly Leu Thr Met
            20                  25                  30

Leu Arg Phe Gly Cys Thr Gln Leu Val Ile Asp Arg Ile Asp Pro Leu
            35                  40                  45

Val Asn Pro Gly Gln Ile Pro Ser Pro His Ile His Gln Ile Ile Gly
50                  55                  60

Gly Asn Ala Phe Asn Ala Thr Met Pro Thr Asp Asp Ile Ala Gln His
65                  70                  75                  80

Ser Thr Cys Thr Thr Cys Ser Phe Ala Asp Asp Phe Ser Asn Tyr Trp
            85                  90                  95

Thr Ala Asn Leu Tyr Phe Lys Ala Arg Asn Gly Ser Tyr Lys Arg Val
            100                 105                 110

Pro Gln Phe Ser Ala Pro Leu Gln Phe Asn Asp Arg Phe Ser Thr Gln
            115                 120                 125

Ile Asn Gly Gly Ile Leu Ile Tyr Tyr Val Ser Ala Gln Pro Gly Arg
            130                 135                 140

Ile Thr Ala Phe Lys Pro Gly Phe Arg Met Leu Val Gly Asp Pro Asn
145                 150                 155                 160

Val Arg Ser Arg Pro Asp Gln Lys Leu Arg Arg Gln Asn Cys Phe Arg
            165                 170                 175

Cys Tyr Ser Gly Pro Asn His Gln Gly Asp Val Gly Ala Pro Cys Met
            180                 185                 190

Asp Asn Asn Tyr Asp Thr Glu Ala Phe Pro Thr Lys Pro Cys Pro Gly
            195                 200                 205

Gly Ile Arg Ser Asn Ile His Phe Pro Thr Cys Trp Asp Ala Tyr Pro
            210                 215                 220
```

```
Thr Ser Gly Pro Ala Asp Phe Leu Ser Leu Gly Gly Asn Cys Pro Ala
225                 230                 235                 240

Ser His Pro Val Arg Ile Pro Gln Leu Met Tyr Glu Val Phe Trp Asp
                245                 250                 255

Thr Ser Lys Phe Ala Asn Arg Ala Asp Trp Pro Ala Asp Gly Ser Gln
            260                 265                 270

Pro Phe Val Leu Ser Thr Gly Asp Pro Thr Gly Leu Gly Gln His Ala
        275                 280                 285

Asp Tyr Val Phe Gly Trp Lys Asp Asp Ser Leu Gln Arg Ala Met Asp
    290                 295                 300

Thr Ser Gly Cys Phe Gly Ala Ser Cys Ala Asn Leu Arg Thr Gln Ser
305                 310                 315                 320

Leu Asp Asn Ala Arg Arg Cys Ala Val Lys Pro Asn Ala Lys Glu Asp
                325                 330                 335

Tyr Asp Ser Cys Glu Phe Gly Pro Gly
            340                 345

<210> SEQ ID NO 33
<211> LENGTH: 364
<212> TYPE: PRT
<213> ORGANISM: Podospora anserina

<400> SEQUENCE: 33

Met Ala Trp Ser Ile Leu Ala Leu Ala Ala Leu Phe Val Gly Ala Glu
1               5                   10                  15

Ala Ala Thr Leu Asp Leu Arg Gln Ser Ala Arg Gly Ser Asp Phe Leu
                20                  25                  30

Arg Phe Ser Cys Ser Gln Leu Val Val Glu Arg Ala Asp Pro Ile Val
            35                  40                  45

Asn Pro Gly Gln Leu Phe Ser Pro His Met His Gln Ile Val Gly Gly
        50                  55                  60

Asn Ser Phe Asn Val Thr Met Asp Pro Ala Thr Ile Asp Pro Pro Lys
65                  70                  75                  80

Gln Ser Lys Cys Thr Ser Cys Arg Met Val Glu Asp Phe Ser Asn Tyr
                85                  90                  95

Trp Thr Ala Ser Ile Tyr Phe Gln Ser Pro Glu Asn Gly Thr Phe Lys
            100                 105                 110

Arg Ile Pro Gln Met Ala Asn Gly Gln Leu Asn Gly Thr Ile Met Asp
        115                 120                 125

Gln Thr Gly Gly Ile Thr Val Tyr Tyr Met Arg Pro Phe Ser Gly Ser
    130                 135                 140

Asn Lys Lys Thr Thr Val Phe Ser Pro Gly Phe Arg Met Ile Ala Gly
145                 150                 155                 160

Asn Pro Val Asn Arg Asn Lys Gly Thr Gly Pro Leu Val Asn Cys His
                165                 170                 175

Arg Cys Leu Ala Lys Asn Asp Arg Ile Ser Gly Gly Asn Gly Ala Pro
            180                 185                 190

Cys Asp Arg Ser Asp Thr Ala Glu Phe Pro Asn Lys Pro Cys Pro Gly
        195                 200                 205

Gly Ile Arg Val Thr Thr Ile Phe Pro Ser Cys Trp Asp Gly Lys Asn
    210                 215                 220

Val Asp Ser Pro Asp His Gln Ser His Val Ala Tyr Ala Pro Gly Asn
225                 230                 235                 240

Gln Ala Leu Ala Gly Asp Arg Cys Pro Ala Ser His Pro Val Arg Ile
```

```
                    245                 250                 255
Pro Gln Val Met Tyr Glu Val Met Tyr Asp Thr Ser Gly Pro Phe Ala
                260                 265                 270

Asn Pro Asp Tyr Tyr Lys Asn Gly Lys Gln Pro Leu Val Tyr Ser Phe
            275                 280                 285

Gly Asp Lys Thr Gly Tyr Gly Ala His Gly Asp Tyr Leu Phe Gly Trp
        290                 295                 300

Glu Asp Gly Ala Leu Gln Arg Ala Met Asp Gly Leu Gly Thr Asn Cys
305                 310                 315                 320

Phe Ser Glu Gln Cys Pro Ala Leu Lys Leu Gln Thr Pro Gln Ala Ala
                325                 330                 335

Asn Glu Cys Thr Lys Gln Gln Gln Ser Arg Glu Asp Val Gly Thr Ser
            340                 345                 350

Thr Cys Glu Phe Val Glu Ser Phe Asn Trp Trp Asn
        355                 360

<210> SEQ ID NO 34
<211> LENGTH: 237
<212> TYPE: PRT
<213> ORGANISM: Podospora anserina

<400> SEQUENCE: 34

Lys Leu Ser Thr Cys Thr Ser Cys Gln Phe Thr Glu Asp Phe Ser Asn
1               5                   10                  15

Tyr Trp Thr Ala Val Met Phe Phe Arg Ala Arg Asn Gly Thr Phe Lys
            20                  25                  30

Arg Val Pro Gln Ile Ala Gln Asn Gly Met Glu Gly Thr Asn Gly Gly
        35                  40                  45

Met Val Val Tyr Tyr Met Ser Asp Ala Leu Phe Asp Thr Ala Gln Lys
    50                  55                  60

Ser Lys Val Thr Ala Phe Lys Pro Gly Phe Arg Met Leu Ser Gln Ala
65                  70                  75                  80

Ser Arg Ala Pro Glu Tyr Ile Ser Phe Pro Pro Thr Pro Cys Arg Gly
                85                  90                  95

Gly Ile Met Ala Asn His Arg Phe Pro Thr Cys Trp Asp Gly Val Asn
            100                 105                 110

Leu Asp Ser Pro Asn His Arg Asp His Val Ala Tyr Pro Glu Thr Gly
        115                 120                 125

Thr Phe Glu Ser Gly Gly Arg Cys Pro Ala Ser His Pro Val Arg Leu
    130                 135                 140

Pro Gln Ile Leu Leu Glu Thr Val Trp Asp Thr Arg Ala Phe Asn Asn
145                 150                 155                 160

Lys Glu Asp Trp Pro Ala Asp Gly Ser Gln Pro Phe Phe Trp Ser Ser
                165                 170                 175

Gly Asp Gly Ser Gly Phe Ala Asn His Ala Asp Tyr Val Phe Gly Trp
            180                 185                 190

Glu Gly Asp Ser Leu Gln Arg Ala Met Asp Ala His Thr Tyr Val Ser
        195                 200                 205

Ala Pro Met Leu Lys Thr Gln Thr Ile Ala Gln Asn Lys Cys Thr
    210                 215                 220

Val Arg Asp Phe Val Arg Glu Asp Phe Ser Gly Cys Lys
225                 230                 235

<210> SEQ ID NO 35
<211> LENGTH: 436
```

```
<212> TYPE: PRT
<213> ORGANISM: Podospora anserina

<400> SEQUENCE: 35
```

| | | | | | | | | | | | | | | | |
|---|---|---|---|---|---|---|---|---|---|---|---|---|---|---|---|
| Met | Asp | Ile | Asn | Trp | Ser | Phe | His | Pro | Ser | Pro | Leu | Leu | Ala | Ala | Pro |
| 1 | | | | 5 | | | | | 10 | | | | | 15 | |
| Leu | Val | Cys | Phe | Pro | Leu | Pro | Phe | Phe | Thr | Ser | Ser | Pro | Gln | Gln | Lys |
| | | | 20 | | | | | 25 | | | | | 30 | | |
| Thr | Pro | His | Pro | Val | Thr | Ile | Met | Asn | Leu | Leu | Leu | Ser | Leu | Ser | Leu |
| | | 35 | | | | | 40 | | | | | 45 | | | |
| Leu | Gly | Val | Ala | Ala | Leu | Ser | Asn | Pro | Leu | Pro | Gln | Pro | Gly | Pro | Asn |
| | 50 | | | | | 55 | | | | | 60 | | | | |
| Pro | Asn | Asp | Pro | Asn | Asp | Pro | Phe | Pro | Leu | Pro | Pro | Asp | Leu | Thr |
| 65 | | | | | 70 | | | | | 75 | | | | | 80 |
| Phe | Asp | Asp | Ile | Ala | Glu | Phe | Pro | Thr | Phe | Asn | Gly | Thr | Gly | Ala | Thr |
| | | | | 85 | | | | | 90 | | | | | 95 | |
| Met | Leu | Arg | Phe | Gly | Cys | His | Gln | Leu | Val | Ile | Asp | Arg | Ile | Asp | Pro |
| | | | 100 | | | | | 105 | | | | | 110 | | |
| Leu | Val | Asn | Pro | Arg | Ala | Val | Pro | Ser | Pro | His | Gln | His | Gln | Ile | Val |
| | | | | 115 | | | | | 120 | | | | | 125 | |
| Gly | Gly | Asp | Ala | Phe | Asp | Ala | Tyr | Met | Pro | Leu | Lys | Asp | Ile | Ala | Lys |
| | 130 | | | | | 135 | | | | | 140 | | | | |
| Arg | Ser | Ser | Cys | Thr | Gly | Cys | Ser | Tyr | Ser | Asp | Asp | Phe | Ser | Asn | Tyr |
| 145 | | | | | 150 | | | | | 155 | | | | | 160 |
| Trp | Thr | Ser | Asn | Leu | Tyr | Phe | Arg | Ala | Arg | Asn | Gly | Ser | Tyr | Lys | Arg |
| | | | | 165 | | | | | 170 | | | | | 175 | |
| Val | Lys | Gln | Ile | Pro | Asn | Asn | Leu | Gln | Phe | Asn | Asp | Thr | Phe | Ala | Thr |
| | | | 180 | | | | | 185 | | | | | 190 | | |
| Gln | Thr | Glu | Gly | Gly | Leu | Thr | Ala | Tyr | Tyr | Val | Ser | Pro | Gly | Gln | Gly |
| | | | 195 | | | | | 200 | | | | | 205 | | |
| Glu | Gln | Gly | Val | Lys | Ala | Phe | Lys | Pro | Gly | Phe | Arg | Met | Phe | Phe | Gly |
| | 210 | | | | | 215 | | | | | 220 | | | | |
| Asp | Ala | Ala | Leu | Arg | Ala | Arg | Pro | Thr | Thr | Gly | Phe | Asn | Leu | Ser | Arg |
| 225 | | | | | 230 | | | | | 235 | | | | | 240 |
| Gln | Thr | Cys | Phe | Arg | Cys | Tyr | Thr | Gly | Pro | Gly | Phe | Glu | Gly | Asp | Asn |
| | | | | 245 | | | | | 250 | | | | | 255 | |
| Leu | Pro | Pro | Cys | Gln | Asp | Pro | Ala | Val | Asp | Ser | Trp | Gly | Leu | Pro | Gln |
| | | | 260 | | | | | 265 | | | | | 270 | | |
| Arg | Lys | Cys | Phe | Gly | Ile | Arg | Ser | Asn | Ile | Leu | Phe | Pro | Thr | Cys | Trp |
| | | | | 275 | | | | | 280 | | | | | 285 | |
| Asp | Gly | Val | Thr | Leu | Asp | Thr | Pro | Asp | His | Lys | Ser | His | Val | Ala | Tyr |
| | 290 | | | | | 295 | | | | | 300 | | | | |
| Pro | Leu | Glu | Gly | Pro | Gln | Pro | Phe | Ser | Ala | Phe | Arg | Thr | Ala | Glu | Ala |
| 305 | | | | | 310 | | | | | 315 | | | | | 320 |
| Cys | Pro | Pro | Ser | His | Pro | Val | Lys | Ile | Pro | Gln | Val | Met | Leu | Glu | Ile |
| | | | | 325 | | | | | 330 | | | | | 335 | |
| Val | Trp | Asp | Thr | Thr | Pro | Phe | Asn | Asp | Pro | Glu | Leu | Trp | Pro | Ala | Asp |
| | | | 340 | | | | | 345 | | | | | 350 | | |
| Gly | Ser | Gln | Pro | Phe | Val | Leu | Thr | Gly | Asp | Arg | Ser | Gly | Tyr | Ser |
| | 355 | | | | | 360 | | | | | 365 | | | | |
| Gln | His | Ala | Asp | Tyr | Val | Phe | Gly | Trp | Lys | Gly | Gln | Glu | Leu | Gln | Lys |
| | | 370 | | | | | 375 | | | | | 380 | | | |
| Ala | Met | Asn | Ala | Gly | Cys | Ala | Ala | Asn | Cys | Pro | Gly | Ile | Lys | Val |
| 385 | | | | | 390 | | | | | 395 | | | | | 400 |

```
Gln Ser Leu Lys Lys Ala Asn Lys Cys Lys Val Lys Pro Leu Val Lys
                405                 410                 415

Glu Lys Ser Glu Gly Cys Lys Phe Cys Phe Leu Asp Thr Val Cys Asp
            420                 425                 430

Val Thr Trp Ser
        435

<210> SEQ ID NO 36
<211> LENGTH: 343
<212> TYPE: PRT
<213> ORGANISM: Podospora anserina

<400> SEQUENCE: 36

Met Lys Ser Leu Ala Ala Thr Leu Val Gly Leu Ile Ala Pro Val Gln
1               5                   10                  15

Ala Gly Leu Arg Phe Pro Cys Ser Thr Leu Thr Ile Gln Arg Leu Asp
            20                  25                  30

Pro Val Glu Pro Gly Asn Ile Pro Ser Ala His Val His His Ile
            35                  40                  45

Val Gly Gly Asn Ala Phe Asn Ala Thr Met Glu Gly Asp Val Gly Glu
        50                  55                  60

Arg Ala Thr Cys Thr Thr Cys Gln Met Ser Glu Asp Phe Ser Asn Tyr
65                  70                  75                  80

Trp Thr Ala His Leu Tyr Phe Lys His Pro Thr Asn Gly Ser Tyr His
                85                  90                  95

Arg Val Pro Val Leu Pro Val Gln Pro Leu Leu Gly Ser Gln Gly
            100                 105                 110

Ala Gln Gly Gly Leu Thr Val Tyr Tyr Thr Gln Phe Asp Leu Thr Arg
        115                 120                 125

Asp Asn Leu Gly Lys Gln Lys Ile Thr Ser Phe Pro Pro Gly Phe Arg
    130                 135                 140

Met Thr Val Gly Thr Pro Thr Glu Pro Gly Lys Pro Arg Val Gly Leu
145                 150                 155                 160

Arg Tyr Gln Cys Leu Gln Gly Gln Asn Arg Gly Arg Glu Leu Asp Asp
                165                 170                 175

Phe Pro Thr Gly Pro Cys Ser Gly Gly Ile Phe Thr Thr His His Phe
            180                 185                 190

Pro Ala Cys Trp Asp Gly Lys Asn Leu Asp Ser Pro Asp His Gln Ser
        195                 200                 205

His Met Tyr Asn Thr Val Thr Arg Asp Gly Phe Leu Asn Ala Gly Pro
    210                 215                 220

Cys Pro Ser Ser His Pro Ile Arg Met Pro Gln Val Ala Phe Glu Thr
225                 230                 235                 240

Val Trp Asp Thr Thr Lys Phe Asn Ser Met Trp Pro Ser Gly Gly Lys
                245                 250                 255

Asn Pro Phe Val Trp Ser Phe Glu Gly Thr Gly Gly Thr His Ala
            260                 265                 270

Asp Tyr Met Phe Gly Trp Lys Gly Asp Ser Leu Gln Arg Ala Met Asp
        275                 280                 285

Lys Ser Glu Cys Phe Tyr Asp Gly Cys Gly Ser Ile Gln Lys Gln Gln
    290                 295                 300

Met Ala Val Ala Asn Arg Cys Ala Ile Lys Glu Thr Val Val Glu Gln
305                 310                 315                 320

Thr Asp Gly Cys Lys Phe Ser Leu Glu Ser Met Arg Glu Arg Lys Val
```

Leu Thr Leu Trp Gln Gly Trp
        340

<210> SEQ ID NO 37
<211> LENGTH: 352
<212> TYPE: PRT
<213> ORGANISM: Podospora anserina

<400> SEQUENCE: 37

Met His Ser Trp Ser Thr Leu Thr Ala Ala Phe Ala Leu Leu Ala Asn
1               5                   10                  15

Gly Val Ala Ala Gln Asn Met Leu Arg Phe Ala Cys Ser Gln Leu Val
            20                  25                  30

Val Asp Arg Val Asp Pro Leu Val Asn Pro Gly Val Arg Tyr Thr Pro
        35                  40                  45

His Leu His Gln Ile Val Gly Gly Asn Ser Phe Asn Leu Thr Met Glu
    50                  55                  60

Pro Val Glu Tyr Asp Leu Val Lys Arg Ser Thr Cys Thr Ser Cys Ser
65                  70                  75                  80

Phe Pro Gln Asp Leu Ser Asn Tyr Trp Thr Ala Val Met Phe Phe Lys
                85                  90                  95

His Lys Asn Gly Ser Tyr His Arg Val Pro Gln Val Gly Asn Gly Gly
            100                 105                 110

Pro Gln Gly Gln Leu Ile Asn Lys Gly Leu Asp Ile Tyr Tyr Ile
        115                 120                 125

Pro Ser Gly Lys Thr Thr Ala Phe Arg Pro Gly Phe Arg Met Leu Ala
    130                 135                 140

Gly Asn Ala Ala Asn Thr Glu Asp Ser Lys Val Ser Lys Ala Asn Ile
145                 150                 155                 160

Cys His Arg Cys Trp Thr Ser Thr Asn Glu Gly Asn Phe Ile Gly Gly
                165                 170                 175

Ala Pro Cys Thr Gly Ser Asp Thr Val Gly Ile Pro Gln Glu Pro Arg
            180                 185                 190

Cys Lys Met Ile Arg Gln Thr Ile Ile Phe Pro His Cys Trp Asp Gly
        195                 200                 205

Lys Asn Leu Asp Thr Pro Asp His Lys Ser His Val Ala Tyr Gly Gln
    210                 215                 220

Gly Ser Gly Ala Thr Gly Gly Ala Cys Pro Ser Ser His Pro Val
225                 230                 235                 240

Lys Leu Pro Gln Leu Met Tyr Glu Leu Met Trp Asn Val Thr Asn Phe
                245                 250                 255

Ser Asp Lys Asn Met Trp Pro Thr Ser Gly Pro Ala Phe Val Tyr Ser
            260                 265                 270

Met Asn Leu Gly Gly Ser Ala Ala His Gly Asp Tyr Val Phe Gly Trp
        275                 280                 285

Glu Gly Asp Thr Leu Gln Arg Ala Met Asp Lys Gly Cys Asn Leu Asn
    290                 295                 300

Arg Ala Cys Pro Ala Ala Gly Leu Thr Tyr Gln Pro Glu Val Tyr
305                 310                 315                 320

Asn Ala Cys Asn Ile Lys Gln Gln Ala Pro Glu Pro Val Asp Gly Cys
                325                 330                 335

Lys Phe Ser Ser Pro Pro Pro Ser Gln Thr Ser Glu Arg Asp Glu Cys
            340                 345                 350

<210> SEQ ID NO 38
<211> LENGTH: 316
<212> TYPE: PRT
<213> ORGANISM: Podospora anserina

<400> SEQUENCE: 38

Met Lys Val Leu Tyr Gly Leu Phe Ser Leu Pro Ala Val Tyr Gly Gln
1               5                   10                  15

Gly Phe Ser Thr Thr Met Leu Arg Phe Gly Cys Ser Glu Val Val Leu
            20                  25                  30

Asp Arg Ile Asp Pro Leu Val Glu Pro Gly Gly Ile Pro Ser Ala His
        35                  40                  45

Val His Gln Val Val Gly Gly Leu Ala Thr Cys Thr Thr Cys Ser Phe
    50                  55                  60

Asp Gln Asp Leu Ser Asn Tyr Trp Thr Ala Asn Val Tyr Phe Lys Ala
65                  70                  75                  80

Arg Asn Gly Thr Tyr Lys Arg Val Pro Gln Met Val Asn Asp Val Gly
                85                  90                  95

Ala Pro Phe Thr Ser Ser Cys Arg Leu Leu Ser Phe Pro Thr Pro Asn
            100                 105                 110

Ile Asp Gln Gln Pro Gly Phe Arg Met Phe Thr Gly Asp Ala Ala Arg
        115                 120                 125

Arg Thr Ser Thr Gly Leu Gly Arg Lys Met Gln Ser Cys Tyr Arg Cys
    130                 135                 140

Tyr Thr Gly Pro Asn Phe Gln Gly Asn Thr Met Ser Pro Cys Met Asp
145                 150                 155                 160

Pro Lys Leu Asp Thr Glu Ser Phe Pro Thr Thr Pro Cys Pro Gly Gly
                165                 170                 175

Ile Arg Ser Ser Val Ile Phe Pro Ile Ala Asp Pro Pro Ser Cys
            180                 185                 190

Trp Asp Gly Lys Asn Leu Asp Thr Pro Asn His Met Asp His Ile Ala
        195                 200                 205

His Pro Thr Ser Gly Pro Ala Thr Phe Ala Val Val Asp Ala Ala Cys
    210                 215                 220

Pro Ala Ser His Pro Val Lys Ile Pro Gln Val His Tyr Glu Ala Ser
225                 230                 235                 240

Gly Cys Cys Arg Gly Phe Asp Val Trp Leu Thr Leu Thr Leu Thr Gly
                245                 250                 255

Tyr Gly Gln His Gly Asp Tyr Val Phe Gly Trp Lys Asp Asp Thr Leu
            260                 265                 270

Gln His Ala Met Asp Asn Arg Cys Phe Ala Ala Thr Cys Arg Gly Leu
        275                 280                 285

Thr Thr Gln Thr Phe Asp Lys Ala Asn Gln Cys Gln Val Lys Arg Val
    290                 295                 300

Val Lys Glu Asp Ile Asp Gly Cys Lys Ser Ala Ser
305                 310                 315

<210> SEQ ID NO 39
<211> LENGTH: 510
<212> TYPE: PRT
<213> ORGANISM: Podospora anserina

<400> SEQUENCE: 39

Met Lys Val Thr Asn Ser Leu Ala Ala Val Leu Ala Ser Ala Gly Leu
1               5                   10                  15

-continued

```
Ser Glu Ala Phe Trp Arg Met Glu Cys Arg Gly Arg Ala Gly Leu Ala
         20                  25                  30
Arg Leu Asp Pro Ile Val Ala Pro Gly Arg Val Ser Gln His Ala His
         35                  40                  45
Ala Ile Phe Gly Ser Ser Ala Asn Gly Val Ser Thr Gly Phe Ser Met
50                   55                  60
Asn Ser Gly His Ala Glu Leu Ala Ala Gly Ser Cys Thr Ser Cys Ala
65                   70                  75                  80
Ala Val Glu Asp Lys Ser Ala Tyr Trp Ser Pro Gln Met Tyr Phe Lys
                 85                  90                  95
His Glu Asp Gly Thr Phe Glu Glu Val Thr Gln Ala Gly Gly Met Leu
                 100                 105                 110
Ala Tyr Tyr Leu Leu Asn Lys Asp Ala Gly Asn Pro Asp Lys Gly Val
             115                 120                 125
Lys Ala Phe Pro Asn Gly Phe Arg Met Val Ala Gly Asp Ser Asn Arg
         130                 135                 140
Arg Asn Tyr Ser Ile Gly Ser Arg Asn Phe Lys Asp Ala Asp Pro Glu
145                 150                 155                 160
Lys Ser Leu Trp Ala Met Leu Gly Glu Thr Ser Gln Glu Asp Leu Ala
                 165                 170                 175
Gln Arg Ala Val Gly Phe Asn Cys Leu Asp Tyr Asn Lys Thr Pro Glu
             180                 185                 190
Gly Ala Leu Val Arg His Tyr Leu Pro Glu Lys Gly Tyr Leu Asp Gly
         195                 200                 205
Asn Cys Pro Asp Gly Ile Arg Leu Glu Leu Met Phe Pro Ser Cys Trp
210                 215                 220
Asn Gly Lys Asp Leu Asp Ser Ala Asn His Lys Ser His Val Ala Tyr
225                 230                 235                 240
Pro Asp Leu Ile Thr Asp Gly Trp Cys Pro Lys Gly Phe Asp Thr Lys
                 245                 250                 255
Leu Pro Ser Leu Met Phe Glu Ile Ile Tyr Glu Thr Asn Lys Phe Lys
             260                 265                 270
Gly Ile Pro Gly Glu Phe Ser Leu Thr Ile Val Gly Phe Gly Phe His
         275                 280                 285
Gly Asp Phe Ala Ser Gly Trp Asp Glu Glu Phe Leu Gln Asp Ala Val
290                 295                 300
Glu Thr Cys Thr Asp Pro Ser Gly Leu Leu Ser Ala Cys Pro Leu Phe
305                 310                 315                 320
Asn Leu Gln Ser Glu Asp Glu Arg Gln Cys Gln Ile Glu Leu Pro
             325                 330                 335
Glu Asp Leu Val Asn Glu Lys Val Thr Gly Lys Arg Gly Lys Ser Leu
         340                 345                 350
Pro Gly Asp Val Pro Ile Arg Tyr Gly Pro Ala Pro Ala Asn Val Gln
         355                 360                 365
Ala Pro Gly Ala Asp Gln Thr Ser His Ile Pro Val Pro Thr Val Thr
370                 375                 380
Tyr Gln Pro Ala Glu Ser Ser Ala Tyr Gln Pro Gly Gly Ile Phe Asn
385                 390                 395                 400
Gly Asp Ala Pro Ser Ser Asn Ser Ser Ser Ser Glu Glu Val Lys
                 405                 410                 415
Val Thr Ala Leu Ala Gln Pro Glu Pro Glu Pro Glu Pro Thr Pro Ala
             420                 425                 430
Pro Thr Pro Thr Pro Ser Glu Ala Pro Leu Pro Ser Gly Tyr Glu Leu
```

```
            435                 440                 445
Val Arg Thr Glu Tyr Val Thr Asn Gly Lys Val Val Ser Lys Ile Val
450                 455                 460

Val Ile Glu Thr Val Glu Tyr Val Met Leu Ala Ala Ala Thr Glu Ile
465                 470                 475                 480

Glu Thr Val Thr Val Thr Ala Thr Leu Asp Ala Gln Lys Ala Arg Arg
                    485                 490                 495

Gly Leu Asn His Leu His Arg His Arg His Ala Gly Ser His
                500                 505                 510

<210> SEQ ID NO 40
<211> LENGTH: 624
<212> TYPE: PRT
<213> ORGANISM: Podospora anserina

<400> SEQUENCE: 40

Met His Phe Thr Thr Ile Leu Ala Thr Met Ala Val Thr Val Ala Ala
1               5                   10                  15

Ala Lys Asp Arg Arg Thr Phe Ala Thr Leu Gln His Lys Gly Arg Gly
                20                  25                  30

Pro Leu Thr Thr Cys Arg Ala Asp Pro Ile Val Ser Pro Gly Gly Pro
            35                  40                  45

Ser Ala His Val His Ala Val Met Gly Ala Ser Asn Phe Gly Phe Asn
50                  55                  60

Val Thr Gly Glu Ser Leu Arg Gln Ser Lys Cys Thr Thr Ala Lys Pro
65                  70                  75                  80

Lys Ala Asp Met Ser Ser Tyr Trp Val Pro Ser Leu Tyr Phe Lys Asp
                85                  90                  95

Pro Glu Thr Gly Leu Leu Glu Pro Val Glu Phe Phe Tyr Met Val Asn
            100                 105                 110

Tyr Tyr Phe Phe Asp Ala Thr Asp Asp Ile Lys Ala Phe Pro Leu
        115                 120                 125

Gly Leu Gln Ile Val Ser Gly Asn Pro Thr Leu Arg Ser Lys Pro Ser
130                 135                 140

His Val Ser Asp Gly Ala Leu Gln Leu Asp Pro Ser Lys Pro Ile Gln
145                 150                 155                 160

Ala Ala Gln Ile Thr Cys Pro Arg Pro Asn Tyr Asn Pro Pro Ser Trp
                165                 170                 175

Pro Asp Asn Ser Asp Gly Ser Arg Ala Gly Leu Gly Asp Pro Ile Asn
            180                 185                 190

Lys Gly Ala Gly Tyr Gly Phe Pro Phe Gln Asn Cys Asp Ala Tyr Ala
        195                 200                 205

Ser Pro Met Arg Val Asp Val His Phe Pro Ser Cys Tyr Asn Pro Ala
210                 215                 220

Ala Gly Leu Thr Asn Tyr Lys Asn Asn Met Ala Phe Pro Thr Pro Val
225                 230                 235                 240

Gly Gly Lys Leu Asn Cys Pro Lys Gly Trp Ile His Val Pro His Met
                245                 250                 255

Phe Phe Glu Thr Tyr Trp Asn Thr Pro Lys Phe Leu Pro Arg Tyr Gln
            260                 265                 270

His Leu Leu Gly Lys Glu Ser Pro Phe Val Phe Ser Asn Gly Asp Ala
        275                 280                 285

Thr Gly Phe Ser Ala His Gly Asp Phe Ile Ser Gly Trp Asp Glu Glu
    290                 295                 300
```

-continued

```
Glu Leu Gln His Ile Ile Asp Thr Cys Asp Ala Gly His Ala Gly Leu
305                 310                 315                 320

His Asn Cys Pro Gly Leu Lys His Gly Val Asn Pro Asp Ser Glu Ser
                325                 330                 335

Cys Asn Ile Glu Cys Pro Ile Gln Glu Lys Ile Ala Gly Thr Leu Asp
            340                 345                 350

Lys Leu Pro Gly Asn Asn Pro Ile Ala Gly Trp Lys Tyr Gly Gly Gly
        355                 360                 365

Asn Val Ser Pro Ala Pro Ala Pro Val Pro Glu Pro Glu Pro Val
370                 375                 380

Val Glu Lys Pro Glu Leu Glu Thr Pro Lys Ser Ser Ala Pro Ala
385                 390                 395                 400

Ile Lys Val Glu Pro Ser Thr Ser Ala Ala Pro Ala Pro Ala Pro Ser
                405                 410                 415

Ser Ser Ser Val Ala Ala Pro Pro Pro Ser Thr Thr Leu Val Thr
            420                 425                 430

Val Pro Ala Pro Ala Pro Thr Lys Val Glu Glu Pro Val Val Glu
        435                 440                 445

Lys Pro Glu Pro Thr Ser Glu Ala Val Leu Pro Pro Ala Ala Ser Pro
450                 455                 460

Lys Val Arg Ile Val Tyr Asp Thr Val Thr Val Trp Gln Thr Arg Thr
465                 470                 475                 480

Val Tyr Glu Ala Pro Ala Gly Pro Thr Gln Ser Ala Lys Ser Gly Ala
                485                 490                 495

Glu Ile Ser Gly Phe Lys Ala Ala Gly Cys Tyr Lys Asp Gln Ser Asp
            500                 505                 510

Arg Val Ile Ser Gly Lys Ile Leu Pro Asn Ile Gly Gln Val Ser Asn
        515                 520                 525

Thr Ala Cys Val Glu Tyr Cys Ser Ser Lys Gly Phe Ser Val Ala Gly
530                 535                 540

Thr Glu Tyr Gly Gly Glu Cys Tyr Cys Gly Asn Ser Leu Asn Thr Val
545                 550                 555                 560

Glu Lys Leu Asp Asp Ser Lys Cys Asn Met Thr Cys Lys Gly Asp Ala
                565                 570                 575

Ser Gln Lys Cys Gly Gly Asp Trp Ala Leu Thr Val Phe Thr Lys Gly
            580                 585                 590

Gly Ala Ala Pro Ala Lys Ala Glu Lys Arg His Val Arg Asn His Asn
        595                 600                 605

His Leu Ala His Ala Arg Ile Pro Ser Arg His Leu His Arg Arg
610                 615                 620

<210> SEQ ID NO 41
<211> LENGTH: 269
<212> TYPE: PRT
<213> ORGANISM: Podospora anserina

<400> SEQUENCE: 41

Lys Arg Phe Met Val Lys Asn Ile Asp Pro Ile Val Tyr Pro Gly Gln
1               5                   10                  15

Tyr Arg Ser His Met His Ser Phe Phe Gly Ser Asp Ala Val Thr Lys
                20                  25                  30

Asp Leu Pro Thr Thr Ala Asp Leu Gln Lys Gly Cys Ala Ser Gly Glu
            35                  40                  45

Asn Pro Asn Asp Leu Ser Val Tyr Cys Glu Thr Lys Ile Ile Asn Ile
        50                  55                  60
```

```
Glu Gly Ile Pro Thr Leu Tyr Tyr Val Arg Gly Pro Thr Asp Phe Val
65                  70                  75                  80

Glu Val Asn Pro Gly Met Phe Ser Thr Tyr Tyr Glu Asn Ile Asp Lys
                85                  90                  95

Ala Glu Ile Pro Tyr Pro Gln Asp Phe Phe Ala Ile Ala Gly Asn Ala
            100                 105                 110

Thr Ala Arg Ser Gln Ser Asp Val Asn Glu Gly Thr Thr Gly Leu Thr
        115                 120                 125

Trp Trp Cys Glu Asn Gly Pro Glu Asp Arg Gln Asn Arg Asn Arg Ala
    130                 135                 140

Leu Met Pro Arg Val Thr Cys Ser Gly Asn Ile Gln Val Ile Leu Arg
145                 150                 155                 160

Phe Pro Asp Cys Val Gln Thr Ser Asn Ile Lys Asn Tyr Ala Tyr Thr
                165                 170                 175

Ala Ala Asn Gly Gly Arg Cys Pro Ser Gly Met Lys Arg Ile Pro Gln
            180                 185                 190

Leu Arg Phe Ser Val Arg Tyr Asn Val Arg Ser Leu Phe Pro Lys Gly
        195                 200                 205

Trp Ser Gly Thr Pro Pro Leu Lys Leu Ala Cys Gly Glu Val Gly Glu
    210                 215                 220

Gly Arg Asn Gln Trp Met Arg Val Asp Gly Ala Arg Gly Glu Gly Lys
225                 230                 235                 240

Ala Gly Thr Thr Cys Gly Pro Lys Asp Arg Glu Pro Ala Lys Gly Thr
                245                 250                 255

Ser Asp Tyr Leu Thr Ser Val Asp Met Met Lys Met His
            260                 265

<210> SEQ ID NO 42
<211> LENGTH: 492
<212> TYPE: PRT
<213> ORGANISM: Aspergillus oryzae

<400> SEQUENCE: 42

Met Arg Gln Thr Met Arg Leu Asp Val Gly Leu Val Thr Cys Leu Ala
1               5                   10                  15

Ala Phe Ser Gly Leu Ala Glu Ala Phe Trp Arg Leu Pro Cys Arg Gly
                20                  25                  30

Arg Ala Gly Leu Ala Arg Leu Asp Pro Leu Met Asp Pro Gly Lys Asp
            35                  40                  45

Ser Tyr His Val His Ala Ile His Gly Pro Ser Phe Ser Met Thr
        50                  55                  60

Ala Asp Met Asp Ser Leu Arg Asp Ser Ser Cys Thr Ser Cys Ala Val
65                  70                  75                  80

Thr Gln Asp Lys Ser Ala Tyr Trp His Pro Ala Leu Tyr Phe Met His
                85                  90                  95

Glu Asn Gly Asp Thr Glu Val Val Asp Gln Val Gly Gly Met Leu Ala
            100                 105                 110

Tyr Tyr Leu Leu Tyr Gly Asp Asn Val Thr Ala Phe Pro Glu Asn Phe
        115                 120                 125

Arg Met Ile Ala Gly Asp Thr Phe Lys Arg Asp Phe Lys Trp Pro Ile
    130                 135                 140

Pro Asp Pro Pro Thr Ser Glu Trp Ser Gly Glu Gln Glu Ser Gln Ala
145                 150                 155                 160

Ala Leu Arg Gln Lys Ala Ile Gly Phe Asn Cys Leu Asn Tyr Asn Lys
```

```
            165                 170                 175
Ala Ala Glu Pro Ser Leu Gly Arg His Phe Leu Pro Asn Lys Thr Tyr
            180                 185                 190

Leu Asp Glu His Cys Thr Asp Gly Val Arg Phe Glu Ile Met Phe Pro
            195                 200                 205

Ser Cys Trp Asn Gly Lys Asp Val Asp Ser Asp His Lys Ser His
    210                 215                 220

Val Ala Tyr Pro Ser Thr Val Met Asp Gly Thr Cys Pro Glu Gly Tyr
225                 230                 235                 240

Asp Thr Arg Val Val Ser Leu Phe Phe Glu Thr Ile Trp Asp Thr Tyr
                245                 250                 255

Ala Phe Lys Asp Lys Lys Gly Thr Phe Val Ile Ser Asn Gly Asp Pro
                260                 265                 270

Thr Gly Phe Gly Tyr His Ala Asp Phe Ile His Gly Trp Glu Ser Gly
                275                 280                 285

Val Leu Glu Gln Ala Val Lys Arg Cys Thr Asn Pro Ser Gly Arg Val
            290                 295                 300

Glu Asp Cys Asp Val Phe Asp Ile Gln Thr Glu Ala Glu Gln Arg Lys
305                 310                 315                 320

Cys Lys Phe Glu Val Pro Thr Leu Leu Lys Asn Glu Asp Val Tyr Ser
                325                 330                 335

His Lys Gly Gly Leu Pro Asn Asp Leu Val Val Glu Tyr Gly Pro Ala
                340                 345                 350

Tyr Ala Ser Pro Ile Ser Tyr Thr Thr Ala Thr Ala Thr Gln Ala Pro
                355                 360                 365

Gly Ala Ser Val Ser Ala Ser Val Ser Val Ser Ile Gly Leu Ser Ile
                370                 375                 380

Asp Leu Pro Gly Ile Val Ala Val Glu Thr Ser Thr Ser Ser Thr Thr
385                 390                 395                 400

Thr Pro Thr Trp Thr Pro Thr Pro Thr Thr Ser Tyr Ile Glu Gly Asp
                405                 410                 415

Val Thr Gln Ala Ile Val Tyr Val Glu Arg Glu Val Thr Val Leu Val
                420                 425                 430

Asp Gly Gln Gly Asn Pro Leu Ala Thr Gln Thr Gly Gly Leu Glu Thr
                435                 440                 445

Val Ser Thr Val Met Ser Thr Thr Ser Ile Ile Ser Thr Val Val
            450                 455                 460

Thr Thr Pro Thr Ala Ser Pro Ala Lys Arg Asp Leu His Glu His Lys
465                 470                 475                 480

His Ala His Gly His His Arg His Gly His His His
                485                 490

<210> SEQ ID NO 43
<211> LENGTH: 335
<212> TYPE: PRT
<213> ORGANISM: Aspergillus oryzae

<400> SEQUENCE: 43

Met Arg Ser Ile Val Leu Ser Ala Leu Ala Ala Gly Phe Ala Gln Ala
1               5                   10                  15

Tyr Thr Val Thr Asn Val Gly Leu Phe Met Phe Lys Asn Ile Asp Pro
                20                  25                  30

Leu Val Val Pro Gly Lys Tyr Thr Ser His Met His Ser Phe Phe Gly
                35                  40                  45
```

```
Ser Asp Ala Ile Thr Ala Asn Thr Lys Thr Ser Glu Glu Leu Gln Lys
    50                  55                  60

Gly Cys Ser Thr Ala Lys Asn Pro Asn Asp Tyr Ser Thr Tyr Trp Val
 65                  70                  75                  80

Pro Thr Leu Tyr His Val Asp Gly Ser Asn Tyr Thr Ala Val Pro Ile
                 85                  90                  95

Phe Arg Phe Ser Ala Tyr Tyr Val Asp Val Asn Ser Ala Glu Ile Ala
                100                 105                 110

Ile Pro Gln Asn Met Lys Leu Leu Ala Gly Asn Ala Thr Ala Thr Ser
                115                 120                 125

Gln Asp Gly Val Asp Gly Asn Ala Gly Ile Gln Trp Phe Cys Asp Ser
130                 135                 140

Gln Ala Gly Glu Glu Lys Asp Asp Ala Ala Phe Pro Thr Glu Thr Cys
145                 150                 155                 160

Lys Tyr His Leu Gln Thr Leu Leu Phe Pro Asp Cys Ala Asn Pro
                165                 170                 175

Asp Thr Leu Glu Tyr Ala Tyr Ser Ala Asn Pro Asp Trp Val Asp Gly
                180                 185                 190

Tyr Gly Lys Asn Arg Cys Pro Ile Gly Met Lys Arg Ile Pro Arg Leu
                195                 200                 205

Arg Phe Ser Ile Arg Tyr Asp Leu Arg Asn Ile Leu Pro Asp Gly Trp
                210                 215                 220

Ser Gly Ser Pro Pro Leu Glu Leu Ala Cys Gly Ser Ser Tyr Cys Ser
225                 230                 235                 240

His Gly Asp Phe Ile Asn Gly Trp Leu Pro Glu Ala Ala Asp Asn Met
                245                 250                 255

Val Lys Asp Ala Ser Ser Asn Asp Arg Glu Tyr Phe Gln Val Ser Gly
                260                 265                 270

Pro Asn Gly Ala Gly Asp Glu Gly Ser Leu Cys Asp Ala Glu Asp Ala
                275                 280                 285

Gln Asp Ser Asp Pro Thr His Gly Thr Ser Asp Tyr Trp Glu Ser Val
                290                 295                 300

Met Met Val Asn Pro Gly Ile Ser Thr Leu Leu Phe Phe Trp Ser Thr
305                 310                 315                 320

Tyr Ser Ser Glu Asp Gly Glu Ser Leu Ala Ile Ala Pro Ser Glu
                325                 330                 335

<210> SEQ ID NO 44
<211> LENGTH: 134
<212> TYPE: PRT
<213> ORGANISM: Aspergillus oryzae

<400> SEQUENCE: 44

Met Ala Tyr Pro Ala Val Gly Asp Tyr Asn Gln Gly Val Cys Pro Glu
 1               5                  10                  15

Thr His Pro Val Ala Val Tyr Ser Ile Phe Val Glu Phe Phe Asn
                 20                  25                  30

Thr Lys Pro Phe Pro Asp Tyr Glu Asn Trp Val Tyr Ala Met Gly Asp
                 35                  40                  45

Pro Thr Gly Tyr Gly Leu His Gly Asp Phe Leu Asn Gly Trp Val Asp
             50                  55                  60

Gln Asn Ala Leu Gln Asn Ala Met Ala Thr Cys Thr Gly Val Glu Gly
 65                  70                  75                  80

Leu Asn Asp Pro Asp Cys Ser Ile Thr Asn Asn Gln Ala Arg Ala Leu
                 85                  90                  95
```

```
Thr Pro Ile Ala His Ser Leu Asp Val Pro Pro Leu Glu Gln Leu
            100                 105                 110

Gly Gln His Gly Pro Leu Ser Lys Leu Pro Gly Asn Asn Pro Ile Thr
        115                 120                 125

Gly Ser Arg Glu Leu Gln
    130

<210> SEQ ID NO 45
<211> LENGTH: 395
<212> TYPE: PRT
<213> ORGANISM: Aspergillus niger

<400> SEQUENCE: 45

Met His Asn Gly Tyr Ile Ala Ala Leu Leu Leu Ser Ser Ser Ser
1               5                  10                  15

Asn Ala Leu Ala Glu Gln Arg Thr Thr Asp Glu Phe Thr Phe Ser Cys
            20                  25                  30

Asp Pro Leu Thr Thr Gln Leu Ser Asp Pro Ile Val Ala Pro Gly Lys
        35                  40                  45

Pro Ser Thr His Thr His Val Val Thr Gly Gly Thr Ala Phe Gln Arg
    50                  55                  60

Thr Met Asn Glu Ser Thr Ala Gln Asn Ala Lys Gly Thr Thr Cys Glu
65                  70                  75                  80

Val Asp Ile Asp Arg Ser Asn Tyr Trp Pro Gln Leu Tyr His Arg
                85                  90                  95

Leu Arg Asn Gly Ser Phe Glu Leu Val Glu Tyr Gln Ser Ser Val Gly
            100                 105                 110

Ile Ala Leu Asp Phe Ala Gly Ser Pro Glu Asn Leu Val Glu Asp Arg
        115                 120                 125

Asp Glu Leu Ala Asn Gly Leu Asp Arg Val Phe Ile Thr Leu Ile Glu
    130                 135                 140

Arg Val Ile Ile Arg Leu Val Leu Arg Ile Val Met Arg Ser Trp Phe
145                 150                 155                 160

His Trp Arg Arg Arg Lys Val Cys Ala Cys Leu Leu Gly Ile Arg Val
                165                 170                 175

Phe Gly Ser Phe Ala Cys Phe Ile Phe Arg Trp Val Arg Val Leu Ile
            180                 185                 190

Ser Asp Gly Asn Arg Thr Tyr Asn Tyr Ser Asn Trp Ser Gln Arg Ala
        195                 200                 205

Val Ser His Met Cys Ile Gly Lys Asp Gly Ser Ser Asn Glu Thr Lys
    210                 215                 220

Gly Leu Pro Gln Gln Pro Cys Glu Ile Leu Arg Ser Gln Val Phe Met
225                 230                 235                 240

Pro Ser Cys Trp Asp Gly Glu Asn Leu Asp Ser Ser Asp His Lys Ser
                245                 250                 255

His Met Ala Tyr Pro Asp Thr Gly Asp Tyr Asn Lys Gly Val Cys Pro
            260                 265                 270

Lys Ser His Pro Val Ala Ile Tyr Ser Ile Phe Leu Glu Phe Phe Phe
        275                 280                 285

Asn Thr Ala Pro His Pro Asp Tyr Lys Asn Trp Ile Tyr Ala Thr Gly
    290                 295                 300

Asp Lys Thr Gly Tyr Gly Leu His Gly Asp Phe Met Tyr Gly Trp Thr
305                 310                 315                 320

Asp Gln Val Ala Leu Gln Gln Ala Ile Asp Thr Cys Thr Gly Pro Gln
```

```
                325                 330                 335
Gly Leu Thr Asp Pro Asp Cys Ser Ile Thr Arg Asn Gln Thr Arg Asp
            340                 345                 350

Leu Ala Pro Met Pro Gln Pro Leu Asp Val Pro Ala Pro Asp Asp Asn
        355                 360                 365

Ile Gly Gln His Gly Pro Val Asp Arg Leu Pro Gly His His Asn Trp
    370                 375                 380

Val Thr Glu His Asp Asn Ser Thr Trp His Gly
385                 390                 395

<210> SEQ ID NO 46
<211> LENGTH: 498
<212> TYPE: PRT
<213> ORGANISM: Aspergillus niger

<400> SEQUENCE: 46

Met Ala Pro Gly Lys Pro Ser Asp His Val His Val His Gly Ser
1               5                  10                  15

Gly Gly Phe Ser Met Ser Ser Gly Glu Thr Ala Leu Lys Asn Ala Asp
            20                  25                  30

Cys Thr Ser Cys Gly Val Thr Gln Asp Lys Ser Ala Tyr Trp Ala Pro
        35                  40                  45

Ala Leu Tyr Phe Met His Glu Asn Gly Asp Ala Glu Leu Val Asn Glu
    50                  55                  60

Val Gly Gly Met Leu Ala Tyr Tyr Phe Leu Asn Gly Gln Asn Val Thr
65              70                  75                  80

Ala Phe Pro Glu Asn Phe Arg Met Ile Ala Gly Asp Pro Phe Leu Arg
                85                  90                  95

Asn Phe Pro Trp Pro Val Pro Asp Pro Pro Lys Ser Glu Trp Ser Gly
            100                 105                 110

Asn Gln Ser Ser Gln Asp Ala Leu Arg Gln Lys Ala Leu Gly Phe Asn
        115                 120                 125

Cys Leu Asn Tyr Asn Lys Ser Pro Glu Pro Ser Leu Gly Arg His Phe
    130                 135                 140

Leu Pro Asn Lys Thr Phe Leu Asp Glu His Cys Thr Asp Gly Val Arg
145                 150                 155                 160

Phe Glu Leu Met Phe Pro Ser Cys Trp Asn Gly Lys Asp Val Asp Ser
                165                 170                 175

Glu Asp His Arg Ser His Met Ala Tyr Pro Ser Leu Val Met Asp Gly
            180                 185                 190

Val Cys Pro Glu Gly Phe Glu Thr Arg Leu Val Ser Leu Phe Tyr Glu
        195                 200                 205

Thr Ile Trp Asp Thr Tyr Ala Phe Lys Asn Lys Gln Gly Thr Phe Val
    210                 215                 220

Leu Ala Asn Gly Asp Pro Thr Gly Tyr Gly Tyr His Gly Asp Phe Ile
225                 230                 235                 240

Tyr Gly Trp Gln Tyr Gly Phe Leu Gln Gln Ala Val Asp Glu Cys Thr
                245                 250                 255

Asn Leu Ser Gly Arg Val Glu Asp Cys Pro Ile Phe Asp Leu Gln Thr
            260                 265                 270

Asp Thr Glu Gln Ala Gln Cys Asn Phe Thr Met Pro Glu Glu Leu Lys
        275                 280                 285

Ser Glu Asn Val Tyr Leu His Lys Gly Gly Leu Pro Asn Asn Ile Ala
    290                 295                 300
```

-continued

```
Ile Gln Tyr Gly Pro Ala Tyr Ala Ser Pro Val Arg Tyr Thr Asn Ala
305                 310                 315                 320

Gly His His Thr Ser Ala Ile Leu Pro Glu Pro Ser Ile Ala Ile Gly
            325                 330                 335

Ala Ser Leu Asn Gly Ala Thr Val Asp Leu Gly Asn Ile His Ile Gly
            340                 345                 350

Val Thr Leu Gly Ala Gly Ala Pro Ser Thr Thr Thr Thr Ser Ser
            355                 360                 365

Thr Leu Ser Thr Ser Thr Leu Pro Ser Ser Thr Gln Thr Ser Thr Leu
            370                 375                 380

Thr Thr Ser Ala Ala Ser Ala Tyr Phe Phe Gln Thr Ser Thr Ser Thr
385                 390                 395                 400

Thr Pro Thr Ser Thr Trp Thr Pro Thr Pro Thr Thr Ser Tyr Val Glu
            405                 410                 415

Gly Val Val Thr Gln Lys Ile Val Tyr Val Glu Gln Glu Ile Leu Ile
            420                 425                 430

Leu Thr Asp Glu Asn Gly Ala Pro Val Thr Thr Glu Thr Gly Gly Ile
            435                 440                 445

Glu Thr Val Ser Thr Ser Thr Ser Thr Val Asn Lys Ile Val Ser Thr
450                 455                 460

Val Val Thr Thr Pro Thr Glu Ala Pro Ala Lys Arg Asp Gly His Ser
465                 470                 475                 480

His Gly His Phe Gln His Val His Arg Arg His Arg His Gly His Ala
            485                 490                 495

His Arg

<210> SEQ ID NO 47
<211> LENGTH: 332
<212> TYPE: PRT
<213> ORGANISM: Trichoderma reesei

<400> SEQUENCE: 47

Met Thr Leu Lys His Ser Ala Leu Val Ala Leu Ala Ala Ala Ile Gly
1               5                   10                  15

Ala Gln Ala Gln Val Phe Thr Val Asn Cys Ala Pro Leu Thr Gln Phe
            20                  25                  30

Arg Gly Asp Pro Ile Val Ser Pro Gly Val Leu Ser Ser His Val His
            35                  40                  45

Ala Val Val Gly Gly Thr Ala Phe Ser Phe Ser Thr Thr Pro Glu Gln
50                  55                  60

Ala Arg Ala Ala Thr Ala Thr Cys Asp Lys Ile Leu Asp Asn Ser
65                  70                  75                  80

Asn Tyr Trp Gln Pro Gln Leu Tyr His Gln Arg His Asp Gly Gln Phe
            85                  90                  95

Glu Leu Val Thr Phe Gln Gly Ser Ala Thr Tyr Tyr Ile Ala Arg Ala
            100                 105                 110

Cys Asp Tyr Ala Pro Gly Arg Gln Asn Cys Asn Gly Ala Pro Leu Pro
            115                 120                 125

Ile Ala Pro Pro Ala Gly Leu Lys Met Leu Val Gly Asp Leu Asn Arg
130                 135                 140

Arg Thr Phe Asn Ala Ser Ser Phe Glu Asp Arg Ala Ile Gln His Val
145                 150                 155                 160

Cys Leu Asp Thr Gln Pro Val Pro Asp Thr Asn Gly Phe Pro Thr Arg
            165                 170                 175
```

-continued

```
Gln Cys Gln Arg Ile Arg Ser Glu Thr Phe Phe Gln Ser Cys Trp Asp
                180                 185                 190

Gly Lys Asn Leu Asp Ser Ala Asn His Lys Asp His Val Ala Phe Pro
            195                 200                 205

Ala Ile Gly Asp Tyr Asn Thr Gly Val Cys Pro Gln Ser His Pro Lys
        210                 215                 220

Ala Ile Leu Ser Val Phe Tyr Glu Phe Tyr Asp Thr Gly Ser Val
225                 230                 235                 240

Lys Asp Phe Asn Arg Phe Val Tyr Ala Asp Gly Asp Ala Thr Gly Tyr
                245                 250                 255

Ser Leu His Ala Asp Tyr Phe Gln Gly Trp Lys Asp Gln Asn Ala Leu
            260                 265                 270

Glu Leu Ala Ile Thr Thr Cys Thr Gly Pro Asn Gly Val Asn Asp Lys
        275                 280                 285

Gly Cys Ser Leu Asn Val Gly Pro Asn Gly Pro Val Ser Gly Pro
    290                 295                 300

Gln Lys Leu Gln Thr Pro Ala Pro Thr Glu Asn Ile Gly Leu Asn Gly
305                 310                 315                 320

Pro Ile Pro Ala Leu Pro Gly Asn Asn Pro Ile His
                325                 330

<210> SEQ ID NO 48
<211> LENGTH: 499
<212> TYPE: PRT
<213> ORGANISM: Trichoderma reesei

<400> SEQUENCE: 48

Met Arg Lys Ser Val Ile Ala Val Thr Ala Gly Leu Ala Ala Val Ala
1               5                   10                  15

Asp Ala Phe Trp Arg Met Glu Cys Gln Gly Arg Val Gly Leu Ala Arg
                20                  25                  30

Met Asp Pro Val Val Tyr Pro Gly Glu Asp Ser Pro His Met His Ala
            35                  40                  45

Ile His Gly Ser Ser Gly Phe Ser Glu Thr Ser Gly Thr Pro Glu Leu
        50                  55                  60

Leu Ala Gly Asn Cys Thr Ser Cys Arg Val Thr Gln Asp Lys Ser Ala
65              70                  75                  80

Tyr Trp His Pro Ala Leu Tyr Phe Gln Asp Ala Asn Thr Lys Glu Tyr
                85                  90                  95

Glu Leu Val Pro Gln Val Gly Gly Met Leu Ala Tyr Tyr Leu Leu Tyr
            100                 105                 110

Gly Asp Asn Ile Lys Ala Phe Pro Thr Asn Phe Arg Met Val Ala Gly
        115                 120                 125

Asp Thr Asn Arg Arg Thr Tyr Thr Ala Gly Asp Pro Thr Gln Pro Asp
    130                 135                 140

Pro Ala Lys Ser Leu Trp Ala Ser Leu Gly Gln Thr Thr Gln Glu Ile
145                 150                 155                 160

Leu Ala Gln Arg Ala Ile Gly Phe Asn Cys Leu Asn Tyr Asp Lys Ala
                165                 170                 175

Pro Glu Gly Thr Leu Tyr Arg His Phe Leu Pro Asp Lys Gly Phe Leu
            180                 185                 190

Asp Ala Asn Cys Lys Asp Gly Ile Arg Phe Glu Ile Met Phe Pro Ser
        195                 200                 205

Cys Trp Lys Gly Gly Asp Ala Leu Asp Ser Pro Asn His Gln Asp His
    210                 215                 220
```

```
Val Ala Tyr Pro Asp Leu Val Met Thr Gly Thr Cys Pro Asp Gly Tyr
225                 230                 235                 240

Pro Glu Arg Leu Pro Ser Met Leu Phe Glu Ile Ile Trp Asn Thr Asn
            245                 250                 255

Ala Tyr Ala Gly Arg Ala Gly Gln Phe Val Leu Ser Asn Gln Asp Thr
        260                 265                 270

Thr Gly Tyr Gly Leu His Gly Asp Phe Ile Met Gly Trp Glu Gln Asp
    275                 280                 285

Phe Leu Gln Gln Ala Val Asn Thr Cys Thr Asn Pro Ser Gly Leu Ile
290                 295                 300

Gln Asp Cys Pro Leu Phe Asn Val Val Asp Glu Ser Val Ala Thr Gln
305                 310                 315                 320

Cys His Leu Glu Asp Met Pro Ala His Leu Arg Lys Glu Asp Gly Asn
            325                 330                 335

Gly Pro Phe Ala Lys Leu Pro Gly Gly Ser Ala Gly Ser Ser Pro
        340                 345                 350

Ser Ser Gly Gly His Gly His Gly Lys Pro Ser Asn Thr Ala Thr Gln
    355                 360                 365

Gly Ala Ala Pro Thr Leu Pro Tyr Gln Pro Gly Val Thr Ala Pro
370                 375                 380

Ser Lys Ala Ser Pro Leu Pro Gly Gln Val Phe Lys Glu Asp Gly Ala
385                 390                 395                 400

Asn Gly Ser Ser Gly Tyr Asn Ala Asp Ala Ile Glu Pro Ala Val Thr
            405                 410                 415

Pro Ala Pro Gly Val Lys Ala Ala Asp Val Gly Ala Glu Phe Val Ser
        420                 425                 430

Thr Gln Tyr Ile Thr Val Gly Asn Val Val Ser Glu Ile Leu Trp Lys
    435                 440                 445

Gln Ala Val Val Thr Val Thr Ala Glu Pro Glu Pro Ser Thr Thr Val
450                 455                 460

Thr Val Thr Ala Thr Gly Pro Arg Pro Pro Gly Leu Met Pro Met Ala
465                 470                 475                 480

Ala Ala Ser Ser Val Ala Ala Tyr Pro Val Glu Leu Pro Thr Gly Asn
            485                 490                 495

Val Pro Ala

<210> SEQ ID NO 49
<211> LENGTH: 544
<212> TYPE: PRT
<213> ORGANISM: Trichoderma reesei

<400> SEQUENCE: 49

Met Ala Gly Val Ala Ala Ala Lys Asp Ser Arg Thr Phe Ala Val Leu
1               5                   10                  15

Arg Phe Thr Asn Lys Gly Leu Val Thr Thr Arg Ala Asp Pro Ile Val
            20                  25                  30

Asn Pro Gly Val Pro Ser Thr His Val His Asn Val Leu Gly Gly Ser
        35                  40                  45

Asn Phe Gly Phe Ser Ser Thr Gly Glu Asp Leu Ile Lys Ser Asn Cys
    50                  55                  60

Ser Thr Ala Leu Val Lys Gly Asp Tyr Ser Asn Tyr Trp Pro Thr
65                  70                  75                  80

Leu Tyr Phe His Asp Pro Lys Thr Gly Asn Phe Glu Tyr Val Asp Val
                85                  90                  95
```

```
Tyr Tyr Thr Asn Val Tyr Tyr Phe Phe Glu Ala Thr Asn Asp Gln Ile
            100                 105                 110

Lys Ala Phe Pro Thr Gly Leu Gln Met Leu Ala Gly Asn Ser Met Gln
            115                 120                 125

Arg Thr Pro Pro Ala Thr Gly Ser Asp Gln Leu Asp Pro Ser Lys Gly
130                 135                 140

Pro Ile Asn Gln Val Gln Phe Thr Cys Pro Arg Ser Ser Tyr Asn Pro
145                 150                 155                 160

Pro Ser Tyr Pro Val Gly Ser Asp Gly Thr Lys Ala Gly Met Val Asp
                165                 170                 175

Pro Asn Asn Gln Gly Ala Gly Val Gly Phe Pro Asp Val Thr Cys Asp
                180                 185                 190

Gly Met Tyr Ser Pro Leu Arg Leu Asp Ile His Phe Pro Ser Cys Tyr
                195                 200                 205

Asn Pro Ala Ala Gly Leu Thr Asn Tyr Lys Glu Asn Met Ala Tyr Pro
            210                 215                 220

Thr Asp Ala Gly Asn Gly Lys Gln Asp Cys Pro Pro Gly Trp Ile His
225                 230                 235                 240

Thr Pro His Ile Phe Phe Glu Val Tyr Tyr Asp Thr Gln Pro Tyr Lys
                245                 250                 255

Gly Arg Trp Thr Glu Asn Gln Gly Thr Gln Pro Phe Val Phe Ser Thr
                260                 265                 270

Gly Asp Val Thr Gly Tyr Ser Gly His Ala Asp Phe Met Ala Gly Trp
                275                 280                 285

Asp Glu Asp Leu Leu Gln His Ile Ile Asp Thr Cys Asp Ala Gly Asp
            290                 295                 300

Ala Gly Met Asp Gln Cys Pro Gly Leu Phe Tyr Gly Leu Asn Ser Gly
305                 310                 315                 320

Asp Cys Thr Ile Glu Pro Leu Val Asp Glu Gln Val Thr Gly Thr Leu
                325                 330                 335

Thr Lys Leu Pro Gly Asn Asn Pro Leu Ser Gly Phe Ser Phe Gly Ala
                340                 345                 350

Ala Pro Gln Met Gly Thr Gly Ser Gly Ser Ser Gly Thr Asn Asn Asn
                355                 360                 365

Ala Ala Ala Ser Ser Thr Pro Gln Pro Ser Leu Leu Pro Pro Ser Pro
            370                 375                 380

Pro Pro Ser Ala Ala Asn Val His Thr Val Thr Glu Thr Val Thr Val
385                 390                 395                 400

Thr Ala Gly Ser Pro Ala Val Thr Ala Ala Ala Ser Pro Ser Gly
                405                 410                 415

Thr Lys Asn Asn Ala Ala Ala Ser Thr Val Gly Gly Tyr Thr Tyr Ala
            420                 425                 430

Gly Cys Tyr Gln Asp Asn Ile Gly Arg Val Leu Ser Gly Asp Val Leu
            435                 440                 445

Pro Asn Leu Gly Pro Met Thr Asn Glu Lys Cys Val Ala Asn Cys Val
            450                 455                 460

Ser Lys Gly Phe Ser Leu Ala Ala Thr Glu Tyr Gly Gly Gln Cys Tyr
465                 470                 475                 480

Cys Gly Asn Glu Leu Val Gly Ser Ala Lys Leu Ala Asp Ser Gln Cys
                485                 490                 495

Ser Val Ala Cys Glu Gly Asn Ser Lys Glu Ile Cys Gly Gly Ser Trp
                500                 505                 510
```

```
Ala Ile Ser Val Tyr Ser Lys Thr Gly Ala Val Ala Met Lys Ala Gly
            515                 520                 525

Lys Ala Arg Arg Ser Glu His Ala His Arg His Arg Ser Gln Arg Asn
530                 535                 540
```

<210> SEQ ID NO 50
<211> LENGTH: 341
<212> TYPE: PRT
<213> ORGANISM: Podospora anserina

<400> SEQUENCE: 50

```
Met Lys Phe His Val Leu Ser Gly Leu Val Ala Gln Val Leu Ser Val
1               5                   10                  15

Ser Ala Gly Thr Ile Leu Trp Asp Gly Arg Phe Asn Asp Met Thr Ser
            20                  25                  30

Ser Ala Asp Leu Asn Lys Trp Ser Trp Gly Asn Gln Val Gly Pro Tyr
        35                  40                  45

Gln Tyr Tyr Ile His Gly Ser Ser Pro Val Ser Ala Tyr Val Asn Leu
    50                  55                  60

Ser Pro Asp Tyr Lys Asn Pro Ala Asp Thr Gly Ser Arg Gln Gly Ala
65                  70                  75                  80

Lys Ile Thr Leu Asp Asn Thr Ala Tyr Trp Asn Gly Gln Asn Met Arg
                85                  90                  95

Arg Thr Glu Leu Ile Pro Gln Thr Thr Ala Ala Ile Asn Gln Gly Lys
            100                 105                 110

Val Tyr Tyr His Phe Ser Leu Met Arg Lys Asp Ile Asn Ala Pro Ala
        115                 120                 125

Thr Thr Arg Glu His Gln Ile Ala Phe Phe Glu Ser His Phe Thr Glu
130                 135                 140

Leu Lys Ser Gly Trp Leu Ser Gly Ala Pro Gly Ile Ser Asp Thr Leu
145                 150                 155                 160

Leu Arg Trp Cys Ile Asp Phe Ala Ala Gly Thr Val Gly Phe Trp His
                165                 170                 175

Ser Thr Gly Ser Asp Pro Leu Thr Arg Lys Val Ala Pro Val Lys Thr
            180                 185                 190

Ser Thr Ser Ser Asn Gly Ala Asp Trp His Val Gly Val Leu Glu Leu
        195                 200                 205

Pro Arg Ser Gly Tyr Pro Asp Ser Asn Glu Asp Phe Tyr Trp Ser Gly
    210                 215                 220

Val Tyr Ile Glu Ser Gly Ser Leu Thr Thr Ser Val Ala Gly Pro Gly
225                 230                 235                 240

Gln Pro Ile Pro Gly Asp Gly Gly Ser Ser Ser Ser Ser Ser Ser Ser
                245                 250                 255

Ser Val Pro Ser Ser Thr Ser Thr Arg Val Ser Ser Thr Ser Thr Pro
            260                 265                 270

Ala Pro Val Ser Ser Thr Thr Leu Val Thr Ser Thr Arg Val Ser
        275                 280                 285

Ser Thr Ser Thr Ser Ser Ala Ala Pro Val Gln Thr Thr Pro Ser Gly
290                 295                 300

Cys Thr Ala Gly Gln Tyr Ala Gln Cys Asp Gly Ile Gly Phe Ser Gly
305                 310                 315                 320

Cys Lys Thr Cys Ala Ala Pro Tyr Thr Cys Lys Tyr Gly Asn Asp Trp
                325                 330                 335

Tyr Ser Gln Cys Leu
            340
```

<210> SEQ ID NO 51
<211> LENGTH: 274
<212> TYPE: PRT
<213> ORGANISM: Podospora anserina

<400> SEQUENCE: 51

Met Lys Thr Ser Thr Leu Leu Ala Ala Leu Cys Gly Val Ala Ala
1               5                   10                  15

Val Glu Gly Ala Val Leu Trp Asp Gly Arg Phe Asn Asp Phe Thr Ser
            20                  25                  30

Ser Ala Asp Leu Asn Lys Trp Ser Trp Ala Asn Gln Val Gly Pro Tyr
        35                  40                  45

Pro Phe Thr Asn Lys Glu Tyr Tyr Ile His Gly Ser Gly Thr Val Asn
    50                  55                  60

Arg Tyr Ile Asn Leu Ser Pro Asp Tyr Lys Asn Pro Asn Asp Thr Val
65                  70                  75                  80

Ser Lys Gln Gly Ala Arg Phe Thr Leu Asp Ser Thr Ala Tyr Trp Asn
                85                  90                  95

Gly Gln Thr Met Arg Arg Ile Glu Leu Ile Pro Gln Thr Lys Ala Ala
            100                 105                 110

Ile Asn Arg Gly Lys Val Phe Tyr His Phe Ser Ile Ser Arg Arg Asp
        115                 120                 125

Thr Asn Ala Pro Ser Val Asn Lys Glu His Gln Ile Cys Phe Phe Glu
    130                 135                 140

Ser His Phe Thr Glu Leu Lys Tyr Gly Trp Ile Ser Gly Glu Gln Gly
145                 150                 155                 160

Ala Ala Asn Pro Ala Leu Gln Trp Met Thr Asn Gln Arg Thr Gln Trp
                165                 170                 175

Lys Leu Ser Glu Trp Lys Ala Asn Val Trp His Asn Phe Ala Tyr Glu
            180                 185                 190

Ile Asp Phe Ser Gly Asn Arg Val Gly Leu Trp Tyr Ser Glu Gly Gly
        195                 200                 205

Ala Asp Leu Lys Gln Val Val Ala Pro Val Gly Gly Val Ser Thr Ser
    210                 215                 220

Ser Asn Gly Gln Asp Trp His Leu Gly Val Leu Glu Leu Pro Arg Ser
225                 230                 235                 240

Gly Tyr Pro Asn Thr Asn Glu Asp Tyr Tyr Phe Ser Gly Val Phe Ile
                245                 250                 255

Glu Asp Gly Ala Ile Thr Thr Lys Ile Gly Gly Pro Gly Glu Phe Phe
            260                 265                 270

Trp Val

<210> SEQ ID NO 52
<211> LENGTH: 379
<212> TYPE: PRT
<213> ORGANISM: Aspergillus flavus

<400> SEQUENCE: 52

Met Gln Ser Leu Ile Thr Leu Leu Ala Leu Pro Ala Ala Thr Leu Ala
1               5                   10                  15

Gly Ser Val Leu Trp Ser Gly Ile Ser Asp Ser Ser Leu Thr Val Asp
            20                  25                  30

Asp Ile Asp Lys Trp Ser Trp Ser Asn Gln Val Gly Ala Trp Gln Trp
        35                  40                  45

```
Tyr Ile His Gly Ser Gly Lys Thr Ser Glu Tyr Leu Gly Ile Ser Pro
         50                  55                  60

Glu Phe Lys Asn Pro Ala Ala Asp Ala Gln Gly Leu Arg Ile Thr
 65                  70                  75                  80

Ile Asp Gly Thr Ser Phe Trp Asn Gly Gln Thr Met Glu Arg Ser Glu
                     85                  90                  95

Leu Ile Pro Gln Thr Lys Ala Asp Leu Gly Ser Gly His Leu Tyr Tyr
                100                 105                 110

His Phe Ser Leu Ser Thr Lys Glu Thr Asn Ala Pro Asn Pro Ser Phe
            115                 120                 125

Glu His Gln Ile Ala Phe Phe Glu Ser His Phe Thr Glu Leu Lys Tyr
    130                 135                 140

Gly Ala Ser Gly Ser Ser Asp Asn Thr Leu Ser Trp Asn Ala Asp Gly
145                 150                 155                 160

Lys Ser His Trp Ser Val Gln Leu Glu Ala Gly Thr Trp Tyr Asn Phe
                165                 170                 175

Ala Tyr Asp Ile Asp Phe Asp Ser Lys Lys Val Gly Leu Trp Ala Ser
                180                 185                 190

Asn Gly Ser Glu Pro Leu Thr Gln Val Val Glu Pro Val Ser Ala Ser
            195                 200                 205

Thr Ser Thr Asn Ser Ala Asp Trp His Val Gly Gln Leu Arg Leu Pro
    210                 215                 220

Gly Ser Glu Ser Asp Asp Ala Ala Glu Asp Trp Phe Trp Ser Gly Val
225                 230                 235                 240

Tyr Ile Glu Glu Gly Pro Ile Thr Thr Glu Ile Gly Ser Glu Ser Ser
                245                 250                 255

Ser Gly Ser Ser Ser Pro Ala Gly Pro Ser Ser Thr Thr Ile Ala Thr
            260                 265                 270

Thr Ala Pro Ala Ser Ser Thr Ala His Ser Ala Thr Ser Thr Gly Gly
    275                 280                 285

Ile Thr Ala Thr Val Ser Ser Val Gly Leu Thr Thr Thr Ala Thr Pro
290                 295                 300

Ser Pro Val Ser Thr Ala Val Ser Ser Ser Val Thr Pro Ser Ser Leu
305                 310                 315                 320

Asn Ala Ala Pro Thr Lys Ser Thr Glu Val Ala Thr Pro Thr Ser Ser
                325                 330                 335

Ser Val Ala Thr Phe Ala Ser Pro Thr Ser Ala Ala Glu Phe Leu Thr
            340                 345                 350

Asp Ile Arg Ala Leu Leu Lys Thr Leu Leu Ser Arg Ser Glu Ala Gly
    355                 360                 365

Ser Val His Ala Arg Asp Phe Ile Arg Arg Gly
    370                 375

<210> SEQ ID NO 53
<211> LENGTH: 99
<212> TYPE: PRT
<213> ORGANISM: Aspergillus flavus

<400> SEQUENCE: 53

Met Lys Ser Phe Leu Phe Leu Ile Pro Leu Val Gln Ala Gly Glu Val
 1               5                  10                  15

Val Trp Asp Gly Phe Phe Asn Ser Ser Phe Thr Val Asp Gln Leu Asp
                20                  25                  30

Lys Trp Ser Trp Ser Asn Pro Val Gly Pro Tyr Gln Tyr Ile His
            35                  40                  45
```

```
Gly Ser Glu Ala Thr Ala Asn Tyr Leu Glu Val Ser Ala Asp Phe Lys
 50                  55                  60

Asn Pro Ala Asp Glu Ser Asp Glu Lys Gly Ile Arg Ile Ser Ile Val
 65                  70                  75                  80

Gln Arg Ser Ser Gln Asp Glu His Leu Trp Pro Arg Lys Val Thr Asn
                 85                  90                  95

Ile Ser Phe

<210> SEQ ID NO 54
<211> LENGTH: 370
<212> TYPE: PRT
<213> ORGANISM: Aspergillus fumigatus

<400> SEQUENCE: 54

Met Arg Ser Phe Ile Ser Leu Leu Ala Phe Pro Ala Ser Leu Ala
  1               5                  10                  15

Gly Ser Val Leu Trp Ser Gly Ile Phe Asp Ser Ser Ala Thr Val Glu
                 20                  25                  30

Asp Phe Asp Lys Trp Ser Trp Ser Asn Gln Val Gly Ser Trp Gln Trp
                 35                  40                  45

Tyr Ile His Gly Ser Gly Lys Thr Ser Glu Tyr Leu Gly Leu Ser Pro
 50                  55                  60

Asp Phe Lys Asn Pro Ala Asp Thr Ser Asp Ala Gln Gly Val Arg Ile
 65                  70                  75                  80

Thr Ile Asp Gly Thr Ser Phe Trp Asn Gly Gln Asn Met Glu Arg Ser
                 85                  90                  95

Glu Leu Ile Pro Gln Thr Thr Ala Asn Leu Gly Ser Gly His Leu Tyr
                100                 105                 110

Tyr His Phe Ser Leu Ser Thr Lys Thr Asn Ala Pro Asp Ala Ser
                115                 120                 125

Phe Glu His Gln Ile Ala Phe Phe Glu Ser His Phe Thr Glu Leu Lys
130                 135                 140

Tyr Gly Ala Ser Gly Ser Ser Asp Asn Thr Leu Arg Trp Tyr Ala Asn
145                 150                 155                 160

Gly Gln Thr His Trp Ser Ile Gln Leu Glu Pro Gly Asn Trp Tyr Asn
                165                 170                 175

Phe Ala Tyr Asp Ile Asp Phe Ala Ser Gln Lys Val Gly Leu Trp Ala
                180                 185                 190

Ser Asn Gly Ser Asp Pro Leu Thr Glu Val Val Ser Pro Val Ser Ala
                195                 200                 205

Ser Thr Ser Thr Asn Ser Ala Asp Trp His Val Gly Gln Leu Arg Leu
210                 215                 220

Pro Asn Gly Gly Ala Ser Asn Asp Ala Pro Glu Asp Trp Phe Trp Ser
225                 230                 235                 240

Gly Ile Tyr Val Glu Gln Ala Pro Ile Thr Lys Glu Ile Gly Ser Pro
                245                 250                 255

Ala Ser Ser Ser Ser Ser Ser Ser Gly Ser Ser Ser Thr Pro
                260                 265                 270

Ser Thr Val Ser Ala Ser Asn Pro Pro Ala Ser Ser Ser Ser
                275                 280                 285

Pro Gln Ala Thr Pro Gln Pro Ser Ser Thr Ser Thr Glu Pro Thr
                290                 295                 300

Ala Thr Pro Ala Ser Gln Ala Val Thr Thr Pro Ala Ala Ser Ala Pro
305                 310                 315                 320
```

Ala Thr Asn Val Ala Thr Pro Ala Glu Ser Ser Pro Gln Leu Pro Ala
            325                 330                 335

Pro Thr Thr Ala Ala Gln Leu Leu Ala Asp Leu Arg Ala Ala Leu Ser
        340                 345                 350

Ala Leu Leu Ser Arg Ser Asn Ser Val His Ala Arg Asp Phe Ala Arg
    355                 360                 365

Arg Gly
    370

<210> SEQ ID NO 55
<211> LENGTH: 269
<212> TYPE: PRT
<213> ORGANISM: Aspergillus fumigatus

<400> SEQUENCE: 55

Met Lys Ser Trp Leu Val Phe Leu Pro Leu Val Arg Cys Asp Val Ile
1               5                   10                  15

Trp Asn Gly Phe Phe Asp Ala Asn Phe Thr Val Asp His Phe Asp Gln
            20                  25                  30

Cys Thr Pro Pro Leu Ser Leu Val Ser Ile Asp Ile His Arg Ser Trp
        35                  40                  45

Ser Asn Gln Ile Pro Pro Tyr Gln Trp Tyr Ile His Gly Ser Gln Pro
    50                  55                  60

Thr Ser His Tyr Leu Ser Leu Ser Pro Ala Phe Lys Asn Pro Ala Ser
65                  70                  75                  80

Lys Val Asp Ala Gln Gly Ile Arg Ile Thr Ile Asp Ser Ser Ser Ser
                85                  90                  95

Trp Asn Gly Gln Thr Met Met Arg Ser Glu Ile Ile Pro Gln Lys Ala
            100                 105                 110

Ala Gly Val Asn Leu Gly Gln Gly His Leu Tyr Tyr His Phe Ser Val
        115                 120                 125

Ser Thr Leu Ala Thr Asn Ala Pro Asp Pro Ser Leu Glu His Gln Ile
    130                 135                 140

Ala Phe Phe Glu Asn His Phe Thr Glu Leu Lys Tyr Gly Arg Leu Ser
145                 150                 155                 160

Gly Thr Ala Asp Asp Asn Thr Leu Arg Trp Met Val Gly Gly Gln Thr
                165                 170                 175

Lys Trp Glu Thr Gln Leu Val Pro Gly Thr Trp Tyr Asn Phe Ala Tyr
            180                 185                 190

Asp Ile Asp Phe Asp Ala Lys Thr Val Gly Leu Trp Ala Ser Thr Gly
        195                 200                 205

Ala Glu Ala Leu Lys Lys Val Val Glu Asn Leu Gly Ala Asn Thr Phe
    210                 215                 220

Thr Asp Ser Gln Asp Trp His Val Gly Glu Leu Arg Leu Asp Asn Gly
225                 230                 235                 240

Ala Thr Ala Ala Ala Glu Asp Trp Phe Trp Ser Gly Tyr Val Ile Glu
                245                 250                 255

Ser Gly Glu Val Thr Thr Asp Val Ala Gly Pro Ser Ala
            260                 265

<210> SEQ ID NO 56
<211> LENGTH: 370
<212> TYPE: PRT
<213> ORGANISM: Aspergillus fumigatus

<400> SEQUENCE: 56

```
Met Arg Ser Phe Ile Ser Leu Leu Ala Phe Pro Ala Ser Ser Leu Ala
1               5                   10                  15

Gly Ser Val Leu Trp Ser Gly Ile Phe Asp Ser Ser Ala Thr Val Glu
            20                  25                  30

Asp Phe Asp Lys Trp Ser Trp Ser Asn Gln Val Gly Ser Trp Gln Trp
        35                  40                  45

Tyr Ile His Gly Ser Gly Lys Thr Ser Glu Tyr Leu Gly Leu Ser Pro
    50                  55                  60

Asp Phe Lys Asn Pro Ala Asp Thr Ser Asp Ala Gln Gly Val Arg Ile
65                  70                  75                  80

Thr Ile Asp Gly Thr Ser Phe Trp Asn Gly Gln Asn Met Glu Arg Ser
                85                  90                  95

Glu Leu Ile Pro Gln Thr Thr Ala Asn Leu Gly Ser Gly His Leu Tyr
            100                 105                 110

Tyr His Phe Ser Leu Ser Thr Lys Thr Thr Asn Ala Pro Asp Ala Ser
        115                 120                 125

Phe Glu His Gln Ile Ala Phe Phe Glu Ser His Phe Thr Glu Leu Lys
    130                 135                 140

Tyr Gly Ala Ser Gly Ser Ser Asp Asn Thr Leu Arg Trp Tyr Ala Asn
145                 150                 155                 160

Gly Gln Thr His Trp Ser Ile Gln Leu Glu Pro Gly Asn Trp Tyr Asn
                165                 170                 175

Phe Ala Tyr Asp Ile Asp Phe Ala Ser Gln Lys Val Gly Leu Trp Ala
            180                 185                 190

Ser Asn Gly Ser Asp Pro Leu Thr Glu Val Val Ser Pro Val Ser Ala
        195                 200                 205

Ser Thr Ser Thr Asn Ser Ala Asp Trp His Val Gly Gln Leu Arg Leu
    210                 215                 220

Pro Asn Gly Gly Ala Ser Asn Asp Ala Pro Glu Asp Trp Phe Trp Ser
225                 230                 235                 240

Gly Ile Tyr Val Glu Gln Ala Pro Ile Thr Lys Glu Ile Gly Ser Pro
                245                 250                 255

Ala Ser Ser Ser Ser Ser Ser Ser Gly Ser Ser Ser Ser Thr Pro
            260                 265                 270

Ser Thr Val Ser Ser Ala Ser Asn Pro Pro Ala Ser Thr Ser Ser Ser
    275                 280                 285

Pro Gln Ala Thr Pro Gln Pro Ser Ser Thr Ser Thr Glu Pro Thr
290                 295                 300

Ala Thr Pro Ala Ser Gln Ala Val Thr Thr Pro Ala Ala Ser Ala Pro
305                 310                 315                 320

Ala Thr Asn Val Ala Thr Pro Ala Glu Ser Ser Pro Gln Leu Pro Thr
                325                 330                 335

Pro Thr Thr Ala Ala Gln Leu Leu Ala Asp Leu Arg Ala Ala Leu Ser
            340                 345                 350

Ala Leu Leu Ser Arg Ser Asn Ser Val His Ala Arg Asp Phe Ala Arg
        355                 360                 365

Arg Gly
    370

<210> SEQ ID NO 57
<211> LENGTH: 258
<212> TYPE: PRT
<213> ORGANISM: Aspergillus clavatus
```

<400> SEQUENCE: 57

```
Met Asp Lys Met Lys Ser Leu Leu Phe Phe Leu Pro Leu Val Arg Cys
1               5                   10                  15

Glu Val Leu Trp Asn Gly Phe Phe Asp Glu Asn Phe Thr Val Ala His
            20                  25                  30

Phe Asp Lys Trp Ser Trp Ser Asn Gln Ile Pro Pro Tyr Gln Trp Tyr
        35                  40                  45

Ile His Gly Ser Gln Pro Thr Ser His Tyr Leu Gly Leu Ser Ala Asp
    50                  55                  60

Phe Lys Asn Pro Ala Ala Thr Ser Asp Ala Gln Gly Ile Arg Ile Thr
65                  70                  75                  80

Ile Asp Asp Thr Ser Ser Trp Asn Gly Gln Thr Met Met Arg Ser Glu
                85                  90                  95

Ile Ile Pro Gln Thr Thr Ala Asn Leu Gly Lys Gly His Leu Phe Tyr
            100                 105                 110

His Phe Ser Leu Ser Thr Arg Glu Thr Asn Ala Pro Ser Pro Gly Phe
        115                 120                 125

Glu His Gln Ile Ala Phe Phe Glu Ser His Phe Thr Glu Leu Lys Tyr
    130                 135                 140

Gly Arg Leu Ser Gly Ala Thr Glu Asp Asp Asn Thr Leu Arg Trp Met
145                 150                 155                 160

Val Gly Gly Gln Thr His Trp Ser Thr Pro Leu Ala Ala Gly Thr Trp
                165                 170                 175

Tyr Asn Phe Ala Tyr Asp Ile Asp Phe Asp Ala Gly Thr Val Gly Leu
            180                 185                 190

Trp Val Ser Glu Gly Ala Ala Pro Leu Ala Arg Ala Val Glu Asn Val
        195                 200                 205

Pro Ala Ala Thr Ser Thr Asn Ser Gln Asp Trp His Val Gly Glu Leu
    210                 215                 220

Arg Leu Asp Asn Gly Gly Ala Ser Gly Pro Ala Glu Asp Trp Phe Trp
225                 230                 235                 240

Ser Gly Val Tyr Val Glu Ser Gly Glu Val Thr Thr Gly Val Ala Gly
                245                 250                 255

Pro Val
```

<210> SEQ ID NO 58
<211> LENGTH: 379
<212> TYPE: PRT
<213> ORGANISM: Aspergillus oryzae

<400> SEQUENCE: 58

```
Met Gln Ser Leu Ile Thr Leu Leu Ala Leu Pro Ala Ser Thr Leu Ala
1               5                   10                  15

Gly Ser Val Leu Trp Ser Gly Ile Ser Asp Ser Ser Leu Thr Val Asp
            20                  25                  30

Asp Ile Asp Lys Trp Ser Trp Ser Asn Gln Val Gly Ala Trp Gln Trp
        35                  40                  45

Tyr Ile His Gly Ser Gly Lys Thr Ser Glu Tyr Leu Gly Ile Ser Pro
    50                  55                  60

Glu Phe Lys Asn Pro Ala Ala Asp Ala Gln Gly Leu Arg Ile Thr
65                  70                  75                  80

Ile Asp Gly Thr Ser Phe Trp Asn Gly Gln Thr Met Glu Arg Ser Glu
                85                  90                  95

Leu Ile Pro Gln Thr Lys Ala Asp Leu Gly Ser Gly His Leu Tyr Tyr
```

```
                100                 105                 110
His Phe Ser Leu Ser Thr Lys Glu Thr Asn Ala Pro Asn Pro Ser Phe
            115                 120                 125

Glu His Gln Ile Ala Phe Phe Glu Ser His Phe Thr Glu Leu Lys Tyr
        130                 135                 140

Gly Ala Ser Gly Ser Ser Asp Asn Thr Leu Ser Trp Asn Ala Asp Gly
145                 150                 155                 160

Lys Ser His Trp Ser Val Gln Leu Glu Ala Gly Thr Trp Tyr Asn Phe
                165                 170                 175

Ala Tyr Asp Ile Asp Phe Asp Ser Lys Lys Val Gly Leu Trp Ala Ser
            180                 185                 190

Asn Gly Ser Glu Pro Leu Thr Gln Val Val Glu Pro Val Ser Ala Ser
        195                 200                 205

Thr Ser Thr Asn Ser Ala Asp Trp His Val Gly Gln Leu Arg Leu Pro
    210                 215                 220

Gly Ser Glu Ser Asp Asp Ala Ala Glu Asp Trp Phe Trp Ser Gly Val
225                 230                 235                 240

Tyr Ile Glu Glu Gly Pro Ile Thr Thr Glu Ile Gly Ser Glu Ser Ser
                245                 250                 255

Ser Gly Ser Ser Ser Ser Ala Gly Pro Ser Ser Thr Thr Ile Ala Thr
            260                 265                 270

Thr Ala Pro Ala Ser Ser Thr Ala His Ser Ala Thr Ser Thr Gly Gly
        275                 280                 285

Ile Thr Ala Thr Val Ser Ser Val Gly Leu Thr Thr Thr Ala Thr Pro
    290                 295                 300

Ser Pro Val Ser Thr Ala Val Ser Ser Val Thr Pro Ser Ser Leu
305                 310                 315                 320

Asn Ala Ala Pro Thr Lys Ser Thr Glu Val Ala Thr Pro Thr Ser Ser
                325                 330                 335

Ser Val Ala Thr Phe Ala Ser Pro Thr Ser Ala Ala Glu Phe Leu Thr
            340                 345                 350

Asp Ile Arg Ala Leu Leu Lys Thr Leu Leu Ser Arg Ser Glu Ala Gly
        355                 360                 365

Ser Val His Ala Arg Asp Phe Ile Arg Arg Gly
    370                 375

<210> SEQ ID NO 59
<211> LENGTH: 249
<212> TYPE: PRT
<213> ORGANISM: Aspergillus terreus

<400> SEQUENCE: 59

Met Lys Ser Val Leu Phe Leu Ala Pro Leu Ala Gln Ala Gly Thr Val
1               5                   10                  15

Val Trp Asn Gly Phe Phe Asn Glu Ser Tyr Thr Leu Asp Thr Leu Asp
            20                  25                  30

Gln Trp Ser Trp Ser Asn Gln Ile Glu Pro Tyr Gln Trp Tyr Ile His
        35                  40                  45

Gly Ser Gly Ala Thr Thr Asp Tyr Leu Ala Leu Ser Pro Glu Tyr Lys
    50                  55                  60

Asn Pro Ala Asp Lys Ala Asp Ala Lys Gly Ile Arg Ile Ser Ile Asp
65                  70                  75                  80

Ser Thr Ser Ser Trp Asn Gly Gln Thr Met Met Arg Ser Glu Leu Ile
                85                  90                  95
```

-continued

Pro Gln Thr Lys Ala Asp Leu Gly Ser Gly Thr Leu Tyr Tyr His Phe
                100                 105                 110

Ser Leu Gln Thr Arg Glu Glu Asn Ala Pro Asp Ala Ser Leu Glu His
            115                 120                 125

Gln Ile Ala Phe Phe Glu Ser His Phe Thr Glu Leu Lys Phe Gly Gly
        130                 135                 140

Ser Gln Ser Thr Leu Asn Trp Met Ala Asn Ser Gln Ser His Trp Ser
145                 150                 155                 160

Ala Pro Leu Gln Ala Gly Thr Trp Tyr Asn Phe Ala Tyr Glu Ile Asp
                165                 170                 175

Phe Asp Ala Gln Thr Val Gly Leu Trp Ala Ser Asn Gly Ser Ala Pro
            180                 185                 190

Leu Thr Arg Ala Val Glu Pro Val Ser Ala Ser Thr Gln Thr Asn Ser
        195                 200                 205

Gln Asp Trp His Ile Gly Glu Leu Arg Leu Asp Asn Gly Gln Ser Gly
210                 215                 220

Pro Lys Glu Asp Trp Tyr Trp Ser Gly Ile Tyr Val Glu Lys Gly Glu
225                 230                 235                 240

Ile Thr Thr Asp Val Gly Gly Pro Ala
                245

<210> SEQ ID NO 60
<211> LENGTH: 256
<212> TYPE: PRT
<213> ORGANISM: Aspergillus nidulans

<400> SEQUENCE: 60

Met Lys Ser Thr Ser Ile Leu Pro Leu Leu Ser Thr Leu Thr Pro Leu
1               5                   10                  15

Ala Ser Ala Ala Thr Val Trp Ser Gly Leu Phe Asn Glu Ser Tyr Thr
                20                  25                  30

Val Ala Asp Phe Asp Lys Trp Ser Trp Ser Ser Gln Ile Pro Pro Tyr
            35                  40                  45

Gln Trp Tyr Ile His Gly Ser Glu Glu Thr Ala His Tyr Leu Ser Leu
        50                  55                  60

Ser Ser Glu Tyr Lys Asn Pro Asn Ser Thr Leu Asp Glu Ala Gln Gly
65                  70                  75                  80

Leu Lys Thr Thr Leu Asp Asn Thr Ala Ser Trp Asn Gly Gln Thr Met
                85                  90                  95

Met Arg Thr Glu Leu Ile Pro Gln Val Glu Ser Gly Val Asp Ile Gly
                100                 105                 110

Ser Gly Lys Lys Tyr Tyr His Phe Ser Leu Ser Val Asp Glu Asp Gly
            115                 120                 125

Leu Pro Asn Val Glu Leu Glu His Gln Ile Ala Phe Phe Glu Ser His
        130                 135                 140

Phe Thr Glu Leu Lys Tyr Gly Gly Ser Ser Asp Thr Ala Ser Ser Leu
145                 150                 155                 160

Thr Phe Tyr Ala Asn Ser Ala Ala Gln Trp Ser Thr Ala Leu Glu Ala
                165                 170                 175

Gly Val Trp Tyr Asn Phe Ala Tyr Gly Ile Asp Phe Asp Gly Gly Ser
            180                 185                 190

Val Glu Leu Tyr Thr Ser Thr Gly Ala Asp Asp Leu Glu Leu Ala Val
        195                 200                 205

Gln Ala Val Ser Ala Ser Ala Ser Ser Asn Ser Gln Asp Trp His Val
210                 215                 220

```
Gly Val Leu Arg Leu Asp Asn Gly Val Asp Gly Glu Glu Ser Trp
225                 230                 235                 240

Tyr Trp Ser Gly Val Tyr Val Glu Asp Gly Glu Val Thr Leu Ala Val
                245                 250                 255
```

<210> SEQ ID NO 61
<211> LENGTH: 410
<212> TYPE: PRT
<213> ORGANISM: Aspergillus niger

<400> SEQUENCE: 61

```
Met Lys Gly Ala Ala Phe Leu Val Phe Pro Ala Ser Thr Leu Ala Gly
1               5                   10                  15

Ser Val Leu Trp Ser Gly Ile Phe Asn Ser Ser Tyr Thr Val Ala Asp
                20                  25                  30

Phe Asp Glu Trp Ser Trp Ser Asn Gln Ile Ala Pro Trp Gln Trp Tyr
            35                  40                  45

Ile His Gly Asp Gly Lys Thr Ser Glu Tyr Leu Ala Leu Ser Ser Asp
    50                  55                  60

Tyr Lys Asn Pro Ala Ala Ser Asp Ala Gln Gly Leu Gln Thr Arg Leu
65                  70                  75                  80

Val Leu Pro Pro Pro His Ala His Asn Thr Phe Ser His Ser Thr Asn
                85                  90                  95

Thr Met Asn Glu Gln Asp Ser Thr Ser Phe Trp Glu Gly Gln Ser Met
            100                 105                 110

Gln Arg Thr Glu Leu Ile Pro Gln Met Ser Pro Ser Ser Ser Ala Ser
        115                 120                 125

Asp Leu Gly Ser Gly His Leu Tyr Tyr His Phe Ser Leu Ser Ala Ser
130                 135                 140

Ser Thr Asn Pro Pro Ser Ser Ser Glu His Gln Ile Ala Phe Phe
145                 150                 155                 160

Glu Ser His Phe Thr Glu Leu Gln Tyr Gln Asp Asn Thr Leu Lys Trp
                165                 170                 175

Asn Ala Gly Gly Asp Thr His Tyr Ser Val Glu Leu Glu Thr Gly Lys
            180                 185                 190

Trp Tyr Asn Phe Ala Tyr Asp Ile Asp Phe Asp Asn Gln Lys Val Gly
        195                 200                 205

Leu Trp Ala Ser Asn Gly Ser Asp Ala Leu Thr Glu Val Val Ser Pro
    210                 215                 220

Val Ser Ala Ser Ala Ser Ser Asn Gly Glu Asp Phe His Val Gly Val
225                 230                 235                 240

Leu Ser Leu Thr Gly Asp Gly Thr Glu Asp Trp Phe Trp Ser Gly Val
                245                 250                 255

Tyr Ile Glu Lys Gly Asp Leu Thr Lys Ser Ile Gly Asp Gly Ser Ser
            260                 265                 270

Ser Glu Ser Ser Ser Gly Ser Ala Thr Thr Ala Gln Ala Val
        275                 280                 285

Glu Ser Thr Ser Ser Ala Ala Ala Ala Thr Ser Ala Ala Thr Thr
    290                 295                 300

Ser Val Glu Ala Thr Ala Ala Ala Thr Pro Thr Gln Asn Val
305                 310                 315                 320

Ala Val Ala Ser Ser Thr Thr Ser Ala Ser Thr Thr Ser Ala Ala
                325                 330                 335

Thr Thr Ser Ser Glu Ser Thr Ala Ala Ala Thr Pro Ser Ala Ser Asn
```

```
                    340                 345                 350
Pro Val Ile Ala Thr Pro Ser Ala Ala Pro Ser Ala Ala Pro Ser Ala
                355                 360                 365

Ala Ala Ala Ser Gly Ser Ala Ala Leu Pro Val Pro Thr Thr Ala Ser
            370                 375                 380

Gln Ile Leu Thr Asp Val Arg Ala Leu Leu Thr Ala Leu Leu Ala Arg
385                 390                 395                 400

Gln Gly Val His Ala Arg Asp Phe Ala Val
                405                 410

<210> SEQ ID NO 62
<211> LENGTH: 347
<212> TYPE: PRT
<213> ORGANISM: Magnaporthe grisea

<400> SEQUENCE: 62

Met Arg Leu Ser Ile Cys Thr Ala Ala Leu Ser Leu Thr Gly Gly Val
1               5                   10                  15

Val Ala Gly Thr Val Ile Trp Asp Gly Arg Phe Asn Asp Met Thr Ser
            20                  25                  30

Ala Ala Asp Leu Asn Lys Trp Ser Trp Gly Asn Gln Val Gly Ser Tyr
        35                  40                  45

Gln Tyr Tyr Ile His Gly Ser Ser Pro Val Thr Ser Tyr Val Asn Leu
    50                  55                  60

Ser Pro Ser His Lys Asn Pro Ala Asp Thr Thr Ser Lys Gln Gly Ala
65                  70                  75                  80

Lys Leu Thr Leu Asp Ser Thr Ala Tyr Trp Asn Gly Gln Asn Met Arg
                85                  90                  95

Arg Ile Glu Leu Ile Pro Gln Thr Thr Ala Ala Ile Asn Gln Gly Lys
            100                 105                 110

Val Phe Tyr His Phe Ser Ile Lys Arg Ser Asp Val Asn Ala Pro Ala
        115                 120                 125

Thr Thr Arg Glu His Gln Ile Ala Phe Phe Glu Ser His Phe Thr Glu
    130                 135                 140

Leu Lys Ser Gly Trp Leu Ser Gly Ala Pro Gly Thr Ser Asp Pro Ala
145                 150                 155                 160

Leu Arg Trp Met Val Asn Gln Gln Thr Lys Trp Ser Val Asp Trp Ala
                165                 170                 175

Ala Asp Val Trp His Asn Val Ala Tyr Glu Ile Asp Phe Ala Ala Asn
            180                 185                 190

Thr Val Gly Phe Trp His Ser Thr Gly Ala Ser Pro Leu Gln Arg Ile
        195                 200                 205

Val Ala Pro Val Ser Val Ser Thr Ser Ser Asn Gly Ala Asp Trp His
    210                 215                 220

Val Gly Val Leu Glu Leu Pro Arg Ser Gly Tyr Pro Asp Ala Val Glu
225                 230                 235                 240

Asp Phe Tyr Phe Ser Gly Val Tyr Ile Glu Thr Gly Thr Ile Thr Thr
                245                 250                 255

Ala Ile Gly Asp Gly Ser Gly Ser Ala Pro Asp Pro Gly Val Pro Gly
            260                 265                 270

Thr Thr Ser Arg Pro Pro Thr Thr Pro Gly Thr Thr Pro Thr Thr Thr
        275                 280                 285

Arg Pro Pro Thr Thr Pro Val Thr Thr Lys Pro Pro Ala Thr
    290                 295                 300
```

```
Thr Thr Gln Pro Pro Ala Gln Pro Gly Gln Thr Arg Tyr Gly Gln Cys
305                 310                 315                 320

Gly Gly Asn Asn Trp Ser Gly Pro Ser Ser Cys Ile Glu Gly Thr Cys
            325                 330                 335

Thr Val Leu Asn Glu Trp Tyr His Gln Cys Ser
        340                 345
```

<210> SEQ ID NO 63
<211> LENGTH: 159
<212> TYPE: PRT
<213> ORGANISM: Magnaporthe grisea

<400> SEQUENCE: 63

```
Met Ala Gly Pro Tyr Gln Tyr Ile His Gly Ser Gly Ser Val Asp
1               5                   10                  15

Lys Tyr Ile Ser Leu Ser Pro Gly Tyr Lys Asn Pro Asn Glu Thr Ala
            20                  25                  30

Ser Ala Arg Gly Ala Arg Phe Ala Leu Asp Gly Ala Val Phe Trp Ile
        35                  40                  45

Gly Gln Asn Met Arg Arg Thr Glu Leu Ile Ser Gln Thr Thr Ala Gly
    50                  55                  60

Ile Val Ser Gly Lys His Phe Thr Glu Met Thr Tyr Gly Trp Ile Ser
65                  70                  75                  80

Gly Glu Gln Gly Thr Ser Asn Lys Asn Leu Gln Trp Met Val Gly Gln
                85                  90                  95

Arg Ser Leu Trp Lys Thr Glu Trp Lys Pro Asp Val Trp His Asn Val
            100                 105                 110

Ala Tyr Glu Ile Ser Ala Asn Leu Pro Pro Thr Glu Pro Thr Asp
        115                 120                 125

Thr Trp Ala Ser Ser Phe His Asp Ser Asn Thr Asn Glu Asp Phe
    130                 135                 140

Tyr Phe Ser Gly Val Ile Ser Ser Pro Ala Pro Ser Pro Pro Leu
145                 150                 155
```

<210> SEQ ID NO 64
<211> LENGTH: 234
<212> TYPE: PRT
<213> ORGANISM: Phaeosphaeria nodorum

<400> SEQUENCE: 64

```
Met Gly Ser Ser Ala Asp Leu Asp Lys Trp Ser Trp Ala Asn Gln Val
1               5                   10                  15

Gly Asn Tyr Gln Tyr Tyr Ile His Gly Ser Gly Ala Thr Ser Lys Tyr
            20                  25                  30

Val Asn Leu Ser Pro Ser Tyr Lys Asn Pro Gly Asp Thr Gly Ser Lys
        35                  40                  45

Gln Gly Ala Lys Ile Thr Ile Asp Ser Thr Ala Lys Trp Asn Ser Asp
    50                  55                  60

Met Trp Arg Thr Glu Leu Ile Pro Gln Thr Lys Ala Ala Ile Asn Gln
65                  70                  75                  80

Gly Thr Val Phe Tyr His Phe Ser Ile Lys Arg Ser Thr Thr Asn Val
                85                  90                  95

Pro Ser Ala Thr Asn Glu His Gln Ile Cys Phe Phe Glu Ser His Phe
            100                 105                 110

Thr Glu Leu Lys Tyr Gly Trp Val Asn Gly Glu Ser Gly Thr Ser Asn
        115                 120                 125
```

```
Thr Asn Leu Gln Trp Met Val Gly Gly Gln Ser Lys Trp Lys Val Glu
        130                 135                 140

Leu Lys Ala Asp Glu Trp His Asn Val Ala Tyr Glu Ile Asn Phe Gly
145                 150                 155                 160

Ser Asn Gln Val Thr Phe Trp His Ser Thr Gly Asn Ser Ser Leu Val
                165                 170                 175

Lys Thr Ala Gly Pro Phe Ser Thr Ser Ser Asn Gly Ala Asp
                180                 185                 190

Trp His Leu Gly Val Leu Arg Leu Pro Arg Gln Gly Asn Asp Gly Thr
                195                 200                 205

Gly Ala Glu Asp Trp Phe Phe Ser Gly Thr Tyr Ile Glu Ser Gly Thr
210                 215                 220

Leu Thr Thr Ser Val Ala Ser Pro Ala Ala
225                 230

<210> SEQ ID NO 65
<211> LENGTH: 361
<212> TYPE: PRT
<213> ORGANISM: Phaeosphaeria nodorum

<400> SEQUENCE: 65

Met Phe Gly Lys Val Ser Ile Leu Ser Ala Leu Val Ser Ala Ala Ser
1               5                   10                  15

Ala Gly Thr Ile Val Trp Asp Gly Arg Phe Asn Asp Met Thr Ser Ser
                20                  25                  30

Ala Asp Ile Ala Lys Trp Ser Phe Ala Thr Pro Val Gly Ser Tyr Gln
            35                  40                  45

Tyr Tyr Ile His Gly Ala Gly Ser Ile Asp Lys Tyr Val Asn Leu Asp
    50                  55                  60

Ser Lys Phe Lys Asn Pro Ala Asp Glu Gly Ser Lys Gln Gly Ala Lys
65                  70                  75                  80

Ile Thr Ile Asp Glu Thr Ser Lys Trp Asn Gly Gln Thr Met Leu Arg
                85                  90                  95

Thr Glu Leu Ile Pro Gln Thr Ser Ala Thr Ile Asn Lys Gly Lys Leu
                100                 105                 110

Phe Tyr His Phe Ser Ile Lys Thr Gly Ala Asp Asn Ala Pro Leu Ala
            115                 120                 125

Ala Asn Glu His Gln Ile Ala Phe Phe Glu Ser His Phe Thr Glu Leu
        130                 135                 140

Lys Tyr Gly Gly Asp Ala Lys Asn Lys Leu Gln Trp Cys Val Ser Gly
145                 150                 155                 160

Gln Pro Lys Trp Asp Val Glu Leu Lys Ala Asp Glu Trp His Asn Val
                165                 170                 175

Ala Tyr Glu Ile Asp Phe Asp Gly Gly Ala Val Thr Phe Trp Tyr Ser
                180                 185                 190

Thr Gly Ser Asp Ala Leu Ala Lys Thr Ala Gly Pro Phe Thr Thr Thr
                195                 200                 205

Thr Ser Ser Asp Gly Lys Asp Phe His Val Gly Val Leu Arg Leu Pro
        210                 215                 220

Gly Ser Asn Asp Ala Pro Gly Ala Glu Asp Trp Phe Phe Ser Gly Val
225                 230                 235                 240

Tyr Ile Glu Ser Gly Glu Ile Asn Thr Ser Val Asn Ser Ala Gly Gly
                245                 250                 255

Ala Ala Gly Ala Ala Pro Ala Pro Ala Ser Pro Ala Lys Pro Ser Ser
                260                 265                 270
```

Ser Ala Ala Ser Ser Thr Leu Val Thr Val Val Lys Pro Ser Ala Ala
            275                 280                 285

Ala Ser Ser Val Val Ala Gln Ala Thr Pro Val Val Thr Pro Thr
    290                 295                 300

Pro Ser Pro Ala Ala Pro Val Val Thr Pro Ser Ala Ser Pro Ala Ala
305                 310                 315                 320

Pro Ala Glu Thr Pro Ala Ala Pro Gln Pro Gly Ser Gly Ser Gly Ser
                325                 330                 335

Asp Ala Lys Leu Pro Lys Glu Phe Thr Ile Lys Gln Phe Val Ala Trp
                340                 345                 350

Leu Arg Ala Lys Gln Ala Gln Gly Asn
            355                 360

<210> SEQ ID NO 66
<211> LENGTH: 405
<212> TYPE: PRT
<213> ORGANISM: Neurospora crassa

<400> SEQUENCE: 66

Met Lys Phe Thr Leu Leu Ser Gly Leu Val Ala Gln Ala Leu Ser Val
1               5                   10                  15

Ser Ala Gly Ser Ile Leu Trp Asp Gly Arg Phe Asn Asp Leu Thr Ser
            20                  25                  30

Ala Thr Asp Leu Ser Lys Trp Ser Trp Ser Ser Gln Val Gly Pro Tyr
        35                  40                  45

Gln Tyr Tyr Ile His Gly Pro Ser Glu Val Thr Ser Tyr Val Asn Leu
    50                  55                  60

Ser Pro Ser Phe Lys Asn Pro Ala Asp Ser Gly Ser Ser Gln Gly Ala
65                  70                  75                  80

Lys Ile Thr Leu Asp Lys Thr Ala Phe Trp Asn Gly Gln Thr Met Arg
                85                  90                  95

Arg Thr Glu Leu Ile Pro Gln Thr Thr Ala Ala Ile Asn Lys Gly Lys
            100                 105                 110

Val Phe Tyr His Phe Ser Leu Met Arg Lys Asp Thr Asn Ala Pro Ala
        115                 120                 125

Leu Thr Arg Glu His Gln Ile Ala Phe Phe Glu Ser His Phe Thr Glu
    130                 135                 140

Leu Lys Ser Gly Trp Gln Ser Gly Ala Ala Gly Thr Ser Asp Pro Leu
145                 150                 155                 160

Leu Arg Trp Cys Ile Gly Gly Gln Thr Lys Trp Ser Val Asn Trp Asp
                165                 170                 175

Ala Asp Val Trp His Asn Val Ala Tyr Glu Ile Asp Phe Asp Ala Asn
            180                 185                 190

Thr Val Gly Phe Trp His Ser Thr Gly Ser Asp Ala Leu Thr Gln Val
        195                 200                 205

Ile Ala Pro Gln Ala Ala Gly Thr Ser Ser Asn Gly Ala Asp Trp His
    210                 215                 220

Val Gly Val Leu Glu Leu Pro Arg Asp Gly Tyr Ala Asp Ala Thr Glu
225                 230                 235                 240

Asp Phe Tyr Phe Ser Gly Val Tyr Ile Glu Ser Gly Ser Ile Thr Thr
                245                 250                 255

Ser Val Ala Gly Pro Gly Ser Ser Ser Asn Pro Gly Thr Pro Ser
            260                 265                 270

Ala Pro Ser Ser Ser Ser Ala Val Pro Val Lys Pro Ser Thr Ser Ser

```
                275                 280                 285
Ala Ser Val Ala Pro Val Lys Pro Ser Thr Ser Ser Thr Ser Ser Ser
            290                 295                 300
Thr Thr Val Ala Ala Val Thr Ser Ser Ala Ala Pro Val Lys Pro Ser
305                 310                 315                 320
Thr Ser Ser Ala Ser Ser Ser Thr Thr Val Ala Ala Val Thr Ser Ala
                325                 330                 335
Ser Ala Ala Pro Ala Val Thr Ser Ser Lys Ala Gly Thr Lys Thr Cys
            340                 345                 350
Thr Arg Lys Ser Ser Ala Ala Pro Ala Ala Thr Thr Ser Ala Gly Ser
                355                 360                 365
Cys Thr Ala Ala Arg Tyr Ala Gln Cys Gly Gly Lys Gly Phe Ser Gly
            370                 375                 380
Cys Thr Ala Cys Ala Ser Pro Tyr Lys Cys Asn Lys Val Asn Asp Trp
385                 390                 395                 400
Tyr Ser Gln Cys Tyr
                405

<210> SEQ ID NO 67
<211> LENGTH: 261
<212> TYPE: PRT
<213> ORGANISM: Neurospora crassa

<400> SEQUENCE: 67

Met Lys Ser Thr Thr Leu Leu Ala Ala Val Leu Ser Ala Phe Ser Thr
1               5                   10                  15
Thr His Ala Ala Leu Leu Trp Asp Gly Arg Phe Asn Asp Phe Thr Ser
                20                  25                  30
Ala Ser Asp Leu Asn Lys Trp Ser Trp Ser Asn Gln Val Gly Pro Tyr
            35                  40                  45
Gln Tyr Tyr Ile His Gly Ser Ser Pro Val Asp Lys Tyr Ile Ser Leu
        50                  55                  60
Ser Glu Ala Tyr Lys Asn Pro Asn Asp Thr His Ser Arg Gln Gly Ala
65                  70                  75                  80
Arg Phe Thr Leu Asp Asn Thr Ala Tyr Trp Asn Gly Gln Asn Met Arg
                85                  90                  95
Arg Ile Glu Leu Ile Pro Gln Thr Lys Glu Ala Ile Asn Arg Gly Lys
            100                 105                 110
Val Tyr Tyr His Phe Ser Ile Met Arg Ser Asp Lys Asn Ala Pro Ser
        115                 120                 125
Val Tyr Arg Glu His Gln Ile Cys Phe Phe Glu Ser His Phe Thr Glu
    130                 135                 140
Leu Lys Ser Gly Trp Ile Ser Gly Glu Ser Gly Ala Ser Asn Pro Asn
145                 150                 155                 160
Leu Gln Trp Met Thr Asn Gln Arg Ser Gly Trp Lys Thr Glu Trp Lys
                165                 170                 175
Ala Gly Val Trp His Asn Val Ala Tyr Glu Ile Asp Phe Ser Ala Asn
            180                 185                 190
Lys Val Gly Phe Trp His Ser Glu Gly Gly Glu Pro Leu Lys Leu Val
        195                 200                 205
Val Ala Pro Val Ser Val Ser Thr Ser Ser Asn Gly Ala Asp Trp His
    210                 215                 220
Leu Gly Ile Leu Glu Leu Pro Arg Asn Gly Tyr Gly Asp Thr Thr Glu
225                 230                 235                 240
```

```
Asp Phe Tyr Phe Ser Gly Val Tyr Ile Glu Thr Gly Pro Ile Thr Thr
                245                 250                 255

Ala Ile Gly Gly Pro
            260

<210> SEQ ID NO 68
<211> LENGTH: 260
<212> TYPE: PRT
<213> ORGANISM: Pyrenophora tritici-repentis

<400> SEQUENCE: 68

Met Phe Gly Gln Thr Thr Ile Ile Gly Ala Leu Ile Ser Ala Val Ser
1               5                   10                  15

Ala Gly Thr Ile Leu Trp Asp Gly Arg Phe Asn Asp Met Thr Ser Ser
            20                  25                  30

Ala Asp Leu Asp Lys Trp Ser Trp Ala Asn Gln Val Gly Asn Tyr Gln
        35                  40                  45

Tyr Tyr Ile His Gly Ser Gly Ala Thr Ser Lys Tyr Val Asn Leu Ser
    50                  55                  60

Pro Asn Tyr Lys Asn Pro Gly Asp Thr Gly Ser Lys Gln Gly Ala Arg
65                  70                  75                  80

Ile Thr Ile Asp Ser Thr Ala Lys Trp Asn Ser Asp Met Trp Arg Thr
                85                  90                  95

Glu Leu Ile Pro Gln Thr Lys Ala Ala Ile Asn Gln Gly Thr Val Tyr
            100                 105                 110

Tyr His Tyr Ser Ile Lys Arg Ser Ser Thr Asn Val Pro Ser Ala Thr
        115                 120                 125

Asn Glu His Gln Ile Cys Phe Phe Glu Ser His Phe Thr Glu Leu Lys
    130                 135                 140

Tyr Gly Trp Ile Ser Gly Glu Ser Gly Thr Ser Asn Thr Asn Leu Gln
145                 150                 155                 160

Trp Met Val Ser Gly Gln Ser Lys Trp Lys Thr Glu Leu Lys Ala Asp
                165                 170                 175

Glu Trp His Asn Val Val Tyr Glu Ile Asn Phe Ser Ser Lys Gln Val
            180                 185                 190

Ser Phe Trp His Ser Thr Gly Asn Asn Thr Leu Val Lys Thr Ala Gly
        195                 200                 205

Pro Phe Ser Thr Ser Thr Ser Ser Asn Gly Ala Asp Trp His Leu Gly
    210                 215                 220

Val Leu Arg Leu Pro Arg Gln Gly Asn Asp Gly Ser Gly Ala Glu Asp
225                 230                 235                 240

Trp Tyr Phe Ser Gly Val Tyr Val Glu Ser Gly Ser Leu Thr Thr Ser
                245                 250                 255

Val Ala Ser Pro
            260

<210> SEQ ID NO 69
<211> LENGTH: 350
<212> TYPE: PRT
<213> ORGANISM: Pyrenophora tritici-repentis

<400> SEQUENCE: 69

Met Phe Gly Lys Ser Ala Leu Met Ser Ala Leu Leu Ser Ala Ala Ser
1               5                   10                  15

Ala Glu Thr Ile Trp Asp Gly Arg Phe Asn Asp Met Thr Ser Ser Ala
            20                  25                  30
```

```
Asp Leu Ser Lys Trp Ser Phe Ala Asn Gln Val Gly Ser Tyr Gln Tyr
            35                  40                  45

Tyr Ile His Gly Ser Gly Ala Val Thr Asp Tyr Val Asn Leu Asp Ala
 50                  55                  60

Lys Phe Lys Asn Pro Ala Asp Thr Ala Ser Lys Gln Gly Val Lys Ile
 65                  70                  75                  80

Thr Ile Asp Asp Thr Ser Lys Trp Asn Gly Gln Thr Met Leu Arg Thr
                 85                  90                  95

Glu Leu Ile Pro Gln Thr Lys Ala Ala Ile Asn Lys Gly Lys Val Tyr
            100                 105                 110

Tyr His Phe Ser Ile Lys Ala Ser Ser Glu Asn Ala Pro Thr Thr Thr
            115                 120                 125

Asn Glu His Gln Leu Ala Phe Phe Glu Ser His Phe Thr Glu Leu Lys
130                 135                 140

Tyr Gly Ala Ser Gly Ser Ala Asn Lys Asn Leu Gln Trp His Val Gly
145                 150                 155                 160

Gly Val Ser Lys Trp Asp Val Glu Leu Val Ala Asp Glu Trp His Asn
                165                 170                 175

Val Ala Tyr Glu Ile Asp Phe Asp Gly Gly Ser Val Thr Phe Trp His
            180                 185                 190

Ser Thr Gly Ser Asp Ala Leu Lys Lys Thr Ala Gly Pro Phe Thr Ala
            195                 200                 205

Ser Thr Ser Ser Asn Gly Ala Asp Trp His Leu Gly Val Leu Arg Leu
210                 215                 220

Pro Gly Asn Asn Asp Pro Lys Gly Ala Glu Asp Trp Phe Phe Ser Gly
225                 230                 235                 240

Val Tyr Ile Glu Asp Gly Thr Leu Thr Thr Ala Val Gly Ser Gly Ala
                245                 250                 255

Gly Gly Ala Ala Ser Pro Gln Lys Pro Ala Pro Ala Ala Ser Ser Thr
            260                 265                 270

Pro Ala Ala Ser Ser Thr Phe Val Thr Ser Thr Ile Ala Pro Ala Lys
            275                 280                 285

Thr Pro Val Ala Glu Pro Ala Asp Thr Pro Ala Asp Val Pro Ala Thr
            290                 295                 300

Ser Ala Thr Pro Thr Pro Thr Pro Thr Pro Ala Pro Val Pro Thr Ala
305                 310                 315                 320

Gly Ser Gly Ser Gly Ser Asp Val Pro Leu Pro Lys Glu Phe Thr Ile
                325                 330                 335

Leu Glu Phe Ile Thr Trp Leu Lys Ala Lys Thr Gly Lys Asn
            340                 345                 350

<210> SEQ ID NO 70
<211> LENGTH: 367
<212> TYPE: PRT
<213> ORGANISM: Neosartorya fischeri

<400> SEQUENCE: 70

Met Arg Ser Phe Ile Ser Leu Leu Ala Phe Pro Ala Ser Ser Leu Ala
1               5                   10                  15

Gly Ser Val Leu Trp Ser Gly Ile Phe Asp Ser Ser Ala Thr Val Glu
            20                  25                  30

Asp Phe Asp Lys Trp Ser Trp Ser Asn Gln Ile Gly Ser Trp Gln Trp
            35                  40                  45

Tyr Ile His Gly Ser Gly Lys Thr Ser Glu Leu Gly Leu Ser Pro
 50                  55                  60
```

```
Asp Phe Lys Asn Pro Ala Thr Ser Asp Ala Gln Gly Val Arg Ile
 65                  70                  75                  80

Thr Ile Asp Gly Thr Ser Phe Trp Asn Gly Gln Asn Met Glu Arg Ser
             85                      90                  95

Glu Leu Ile Pro Gln Thr Thr Ala Asn Leu Gly Ser Gly His Leu Tyr
            100                 105                 110

Tyr His Phe Ser Leu Ser Thr Lys Thr Thr Asn Ala Pro Asp Ala Ser
            115                 120                 125

Phe Glu His Gln Ile Ala Phe Phe Glu Ser His Phe Thr Glu Leu Lys
130                 135                 140

Tyr Gly Ala Ser Gly Ser Ser Asp Asn Thr Leu Arg Trp Asn Ala Gly
145                 150                 155                 160

Gly Gln Thr His Trp Ser Val Gln Leu Glu Pro Gly Asn Trp Tyr Asn
            165                 170                 175

Phe Ala Tyr Asp Ile Asp Phe Ala Ser Gln Lys Val Gly Leu Trp Ala
            180                 185                 190

Ser Asn Gly Ser Asp Pro Leu Thr Glu Val Val Ser Pro Val Ser Ala
            195                 200                 205

Ser Thr Ser Thr Asn Ser Ala Asp Trp His Val Gly Gln Leu Arg Leu
210                 215                 220

Pro Asn Gly Gly Ala Ser Asn Asp Ala Pro Glu Asp Trp Phe Trp Ser
225                 230                 235                 240

Gly Ile Tyr Val Glu Gln Ala Pro Ile Thr Lys Glu Ile Gly Ser Pro
            245                 250                 255

Gly Ser Ser Ser Gly Ser Ser Ser Ser Ser Ser Ala Ser
            260                 265                 270

Ser Ala Ser Asn Pro Ser Ala Ser Thr Ser Ser Thr Pro Gln Ala Thr
            275                 280                 285

Ala Arg Pro Ser Ser Thr Pro Ser Thr Glu Pro Ala Ala Thr Pro Ala
290                 295                 300

Ser Gln Ala Val Thr Thr Pro Ala Ala Ser Ala Pro Asn Thr Asn Ala
305                 310                 315                 320

Ala Thr Pro Ala Glu Pro Ser Ser Ala Gln Leu Pro Thr Pro Thr Thr
            325                 330                 335

Ala Ala Gln Leu Leu Ala Asp Leu Arg Ala Ala Leu Gly Ala Leu Leu
            340                 345                 350

Ser Arg Ser Asn Ser Val His Ala Arg Asp Phe Ala Arg Arg Gly
            355                 360                 365

<210> SEQ ID NO 71
<211> LENGTH: 257
<212> TYPE: PRT
<213> ORGANISM: Neosartorya fischeri

<400> SEQUENCE: 71

Met Lys Pro Trp Leu Leu Phe Leu Pro Leu Val Arg Cys Asp Val Ile
 1               5                  10                  15

Trp Asn Gly Phe Phe Asp Ala Asn Phe Thr Val Asp His Phe Asp Gln
                20                  25                  30

Trp Ser Trp Ser Asn Gln Ile Pro Pro Tyr Gln Trp Tyr Ile His Gly
            35                  40                  45

Ser Gln Pro Thr Pro His Tyr Leu Gly Leu Ser Pro Ala Phe Lys Asn
        50                  55                  60

Pro Ala Ser Lys Val Asp Ala Gln Gly Ile Arg Ile Thr Ile Asp Ser
```

```
                65                  70                  75                  80
Ser Ser Ser Trp Asn Gly Gln Thr Met Met Arg Ser Glu Ile Ile Pro
                    85                  90                  95

Gln Lys Ala Ala Gly Val Asn Leu Gly Gln Gly His Leu Tyr Tyr His
                    100                 105                 110

Phe Ser Val Ser Thr Gly Glu Thr Asn Ala Pro Asp Pro Gly Leu Glu
                    115                 120                 125

His Gln Ile Ala Phe Phe Glu Asn His Phe Thr Glu Leu Lys Tyr Gly
                    130                 135                 140

Arg Leu Ser Gly Thr Ala Asp Asp Asn Thr Leu Arg Trp Met Val Gly
145                 150                 155                 160

Gly Gln Thr Lys Trp Asp Thr Gln Leu Val Pro Gly Thr Trp Tyr Asn
                    165                 170                 175

Phe Ala Tyr Asp Ile Asp Phe Asp Ala Lys Thr Val Gly Leu Trp Ala
                    180                 185                 190

Ser Thr Gly Ala Glu Ala Leu Lys Lys Val Val Glu Asn Ile Gly Ala
                    195                 200                 205

Asn Thr Phe Thr Asp Ser Gln Asp Trp His Val Gly Glu Leu Arg Leu
                    210                 215                 220

Asp Asn Gly Val Asn Ala Pro Ala Glu Asp Trp Phe Trp Ser Gly Val
225                 230                 235                 240

Tyr Ile Glu Ser Gly Met Val Thr Thr Asp Val Ala Gly Pro Ser Asp
                    245                 250                 255

Tyr

<210> SEQ ID NO 72
<211> LENGTH: 346
<212> TYPE: PRT
<213> ORGANISM: Chaetomium globosum

<400> SEQUENCE: 72

Met Lys Phe Ser Val Leu Ser Ser Ile Leu Ala Asn Ala Leu Ser Val
1               5                   10                  15

Ser Ala Gly Thr Ile Leu Trp Asp Gly Arg Phe Asn Asp Leu Ser Ser
                    20                  25                  30

Ser Thr Asp Leu Asn Asn Trp Ser Trp Gly Asn Gln Val Gly Pro Tyr
                    35                  40                  45

Gln Tyr Tyr Ile His Gly Ser Ser Val Thr Ser Tyr Val Asn Leu
                    50                  55                  60

Ser Pro Asp Tyr Lys Asn Pro Ala Asp Ser Gly Ser Lys Gln Gly Ala
65                  70                  75                  80

Lys Ile Thr Leu Asp Asn Thr Ala Tyr Trp Asn Gly Gln Asn Met Arg
                    85                  90                  95

Arg Thr Glu Leu Ile Pro Gln Thr Thr Ala Pro Ile Ala Gln Gly Lys
                    100                 105                 110

Val Tyr Tyr His Phe Ser Leu Met Arg Lys Asp Thr Asn Ala Pro Ala
                    115                 120                 125

Thr Thr Arg Glu His Gln Ile Ala Phe Phe Glu Ser His Phe Thr Glu
                    130                 135                 140

Leu Lys Ala Gly Trp Leu Ser Gly Ala Pro Gly Val Ser Asp Thr Leu
145                 150                 155                 160

Leu Arg Trp Cys Val Gly Gly Gln Thr Lys Trp Ser Thr Glu Trp Glu
                    165                 170                 175

Ala Asn Val Trp His Asn Val Ala Tyr Glu Ile Asp Phe Ser Ala Asn
```

```
            180                 185                 190
Thr Val Ala Phe Trp His Ser Thr Gly Gly Asp Ala Leu Thr Gln Lys
                195                 200                 205

Ile Ala Pro Val Ser Thr Ser Thr Ser Ser Asn Gly Ala Asp Trp His
    210                 215                 220

Val Gly Val Leu Glu Leu Pro Arg Ser Gly Tyr Ser Asp Ser Asn Glu
225                 230                 235                 240

Asp Tyr Tyr Trp Ser Gly Val Tyr Ile Glu Ser Gly Ser Leu Thr Thr
                245                 250                 255

Asn Val Ala Gly Pro Gly Ala Pro Ser Gly Gly Gly Ser Ser Ser
                260                 265                 270

Ser Ala Val Ser Ser Ser Thr Lys Ala Pro Val Ser Ser Thr Thr
    275                 280                 285

Leu Ala Thr Ser Thr Thr Thr Pro Ala Pro Ala Thr Ser Thr Thr
                290                 295                 300

Ala Gly Pro Val Gly Cys Thr Ala Gly Gln Trp Ala Gln Cys Asp Gly
305                 310                 315                 320

Thr Gly Tyr Ser Gly Cys Lys Ala Cys Ala Ser Pro Tyr Lys Cys Asn
                325                 330                 335

Tyr Val Asn Asp Trp Tyr Ser Gln Cys Tyr
                340                 345

<210> SEQ ID NO 73
<211> LENGTH: 574
<212> TYPE: PRT
<213> ORGANISM: Botryotinia fuckeliana

<400> SEQUENCE: 73

Met His Phe Ser Lys Lys Ala Leu Ala Ala Leu Ile Gly Ser Ala Thr
1               5                   10                  15

Ser Ala Asn Gly Ala Ile Leu Trp Asp Gly Arg Phe Asp Ser Ser Ser
                20                  25                  30

Met Ala Asp Leu Glu Ala Trp Ser Trp Ser Asn Ala Val Gly Asp Tyr
            35                  40                  45

Gln Asn Tyr Ile His Gly Thr Ser Asn Ile Thr Ser Tyr Val Ala Leu
    50                  55                  60

Asp Ser Thr Tyr Lys Asn Pro Ala Asp Ser Gly Ser Ala Leu Gly Ala
65                  70                  75                  80

Lys Ile Thr Leu Asp Ser Thr Ser Tyr Trp Glu Gly Gln Asn Met Arg
                85                  90                  95

Arg Thr Glu Leu Ile Pro Gln Thr Ser Ala Ala Ile Gly Ser Gly Lys
            100                 105                 110

Val Tyr Tyr His Phe Ser Met Met Arg Glu Asp Thr Asn Ala Pro Ser
    115                 120                 125

Ile Tyr Arg Glu His Gln Ile Cys Phe Phe Glu Ser His Phe Thr Glu
130                 135                 140

Met Lys Ser Gly Trp Ile Ser Gly Glu Ser Gly Ser Ser Asp Pro Leu
145                 150                 155                 160

Leu Arg Trp Asp Val Ser Ser Thr Ser Gln Trp Ser Thr Asn Trp Thr
                165                 170                 175

Ala Gly Val Trp His Asn Ile Ala Tyr Gly Ile Asp Phe Ser Ala Gly
            180                 185                 190

Ser Val Glu Phe Tyr His Ser Thr Gly Ser Asp Ala Leu Thr Leu Thr
    195                 200                 205
```

```
Val Pro Ala Val Lys Val Ser Ala Ser Ser Asn Gly Ala Asp Trp His
    210             215                 220
Leu Gly Val Leu Glu Leu Pro Val Thr Gly Gln Thr Asp Gly Thr Glu
225             230                 235                 240
Asp Phe Tyr Phe Ser Gly Val Tyr Ile Glu Ser Gly Ser Leu Thr Thr
            245                 250                 255
Ser Val Ala Gly Pro Gly Ala Val Val Ser Ser Ser Ser Ala
            260                 265                 270
Thr Ser Ser Val Asp Ser Ser Ser Val Ala Ser Ser Ser Val Val Ser
        275                 280                 285
Ile Ala Ser Ser Ser Val Val Glu Ala Ser Ser Ser Leu Ala Ser
    290                 295                 300
Ser Ala Thr Ser Ile Glu Ala Val Ser Thr Gln Ala Ala Ile Pro Ser
305             310                 315                 320
Ser Ser Ala Ile Val Ser Ser Val Thr Ser Ala Val Ala Gln
            325                 330                 335
Val Gln Ala Ser Ser Ser Ile Val Ser Ser Pro Ser Ser Thr Lys
        340                 345                 350
Lys Ser Cys Thr Lys Lys Val Ala Ser Ala Thr Pro Ile Ser Ser Ala
355                 360                 365
Ala Ala Gln Gln Ser Ser Thr Lys Lys Ser Cys Thr Lys Lys Ala Ser
    370                 375                 380
Ser Ala Thr Ala Ile Thr Ser Ala Val Ala Ile Ala Ser Gln Ala Ser
385             390                 395                 400
Gly Ser Ile Val Glu Phe Thr Thr Gln Thr Val Thr Ser Val Asp
            405                 410                 415
Ile Ile Pro Thr Thr Val Tyr Val Thr Ala Gly Gly Ser Thr Phe Leu
            420                 425                 430
Thr Thr Ser Ser Val Ser Ser Thr Tyr Thr Ser Glu Ser Ala Val Ile
        435                 440                 445
Thr Ser Ser Ser Val Leu Ser Ile Ala Ala Pro Ser Thr Phe Val Thr
    450                 455                 460
Ser Lys Lys Ser Cys Thr Lys Lys Ala Ser Ser Ala Ala Ile Ala Ser
465             470                 475                 480
Ser Leu Ala Gly Asn Val Asn Val Ala Ala Ser Ser Ala Val Leu
            485                 490                 495
Thr Ser Ala Gly Ala Ser Ser Lys Pro His Thr Thr Leu Thr Met Thr
        500                 505                 510
Val Thr Gln Thr Thr Ser Thr Thr Val Ala Ser Ser Ala Gly Ala Thr
    515                 520                 525
Ser Thr Gly Gly Ser Ser Gly Glu Ile Ala Leu Tyr Met Gln Cys
530                 535                 540
Gly Gly Lys Asn Trp Thr Gly Thr Gly Thr Cys Val Ser Gly Ser Thr
545             550                 555                 560
Cys Thr Val Gln Asn Asp Tyr Tyr Ser Gln Cys Ile Ser Ala
            565                 570

<210> SEQ ID NO 74
<211> LENGTH: 521
<212> TYPE: PRT
<213> ORGANISM: Sclerotinia sclerotiorum

<400> SEQUENCE: 74

Met His Phe Ser Lys Lys Ala Leu Ala Ala Leu Ile Gly Ser Val Thr
1               5                   10                  15
```

-continued

```
Ser Ala Asn Cys Ala Ile Leu Trp Asp Gly Arg Phe Asp Ser Ser Thr
             20                  25                  30

Met Ala Asp Leu Glu Ala Trp Ser Trp Ser Asn Ala Val Gly Asp Tyr
         35                  40                  45

Gln Asn Tyr Ile His Gly Thr Ser Asn Phe Thr Asn Tyr Ile Thr Leu
 50                      55                  60

Gly Ser Ser Phe Lys Asn Pro Ala Asp Ser Gly Ser Ser Leu Gly Ala
 65                  70                  75                  80

Lys Ile Thr Leu Asp Ser Thr Ser Tyr Trp Gln Gly Gln Asn Met Arg
                 85                  90                  95

Arg Thr Glu Leu Ile Pro Gln Thr Lys Ala Ala Ile Ala Ser Gly Lys
            100                 105                 110

Val Tyr Tyr His Phe Ser Met Met His Met Glu Ala Asn Ala Pro Ser
            115                 120                 125

Ile Tyr Arg Glu His Gln Ile Cys Phe Phe Glu Ser His Phe Thr Glu
130                 135                 140

Met Lys Ser Gly Trp Ile Ser Gly Glu Ser Gly Ser Ser Asp Pro Leu
145                 150                 155                 160

Leu Arg Trp Asp Val Ser Gly Asn Ser Lys Trp Ser Thr Asn Trp Thr
                165                 170                 175

Ser Gly Val Trp His Asn Val Ala Tyr Gly Ile Asp Phe Ser Ala Gly
            180                 185                 190

Ser Val Glu Phe Tyr His Ser Thr Gly Ser Asp Pro Leu Thr Leu Thr
            195                 200                 205

Val Pro Ala Val Ser Val Ser Ala Ser Asn Gly Ala Asp Trp His
            210                 215                 220

Leu Gly Val Leu Glu Leu Pro Val Ser Gly Gln Ala Asp Gly Thr Glu
225                 230                 235                 240

Asp Phe Tyr Phe Ser Gly Val Tyr Ile Glu Ser Gly Ser Leu Thr Thr
                245                 250                 255

Ser Val Ala Gly Pro Gly Gly Ala Val Val Ser Ser Ser Ser Ser Ala
            260                 265                 270

Ser Thr Leu Val Glu Ser Ser Ile Ala Leu Ser Ser Val Pro
            275                 280                 285

Gly Val Glu Ala Ser Ser Ala Val Ala Ser Ser Glu Thr Ser Val Gln
290                 295                 300

Ala Ile Ser Thr Gln Val Ser Ile Ser Ser Ser Thr Val Leu Ser Val
305                 310                 315                 320

Thr Gln Ser Ser Ser Val Ala Ile Pro Ala Gln Gln Ser Ser Ser Val
                325                 330                 335

Ile Ala Ser Pro Ser Thr Thr Thr Lys Lys Pro Cys Thr Lys Lys Val
            340                 345                 350

Ser Pro Gly Thr Thr Thr Thr Asn Ile Pro Gln Val Ser Ser Pro Ser
            355                 360                 365

Ser Ala Ser Ile Ile Glu Phe Thr Ser Thr Lys Ala Ile Thr Ser Ile
            370                 375                 380

Glu Ile Ile Pro Thr Thr Ile Tyr Ile Thr Ala Gly Gly Ser Thr Ile
385                 390                 395                 400

Leu Ser Thr Ser Ser Val Ser Lys Thr Tyr Thr Ser Gln Ser Ala Ile
                405                 410                 415

Ile Thr His Ser Ser Ile Leu Pro Ile Ala Ile Pro Thr Phe Leu
            420                 425                 430
```

-continued

```
Thr Ser Lys Lys Pro Cys Thr Lys Pro Ser Pro Ser Ser Ser Ser
            435                 440                 445

Ser Leu Ser Gly Asn Leu Asn Ile Ala Ser Thr Leu Ser Ser Ser Ser
450                 455                 460

Gly Ile Leu Thr Pro Ser Pro Ser Ser Ile Pro His Thr Thr Leu Thr
465                 470                 475                 480

Thr Thr Ile Thr Gln Thr Ser Ser Thr Val Ser Ser Ala Ser
            485                 490                 495

Ala Thr Ser Thr Ala Gly Ser Gly Ser Ala Gly Thr Ile Ala Lys Tyr
            500                 505                 510

Ala Gln Cys Val Gln Asn Val Glu Val
            515                 520

<210> SEQ ID NO 75
<211> LENGTH: 262
<212> TYPE: PRT
<213> ORGANISM: Moniliophthora perniciosa

<400> SEQUENCE: 75

Met Tyr Arg Leu Thr Val Ala Thr Thr Phe Ala Ile Leu Ala Ser Ile
1               5                   10                  15

Ala Ser Ala Gly Thr Lys Leu Trp Asp Gly Ser Phe Asn Ser Tyr Ala
            20                  25                  30

Ser Ala Ala Asp Phe Asp Lys Trp Ser Trp Ala Asn Gln Val Gly Thr
        35                  40                  45

Tyr Gln Trp Tyr Ile His Gly Ser Gln Ala Thr Ser His Tyr Leu Ala
    50                  55                  60

Val Ser Pro Asp Tyr Lys Asn Pro Ala Met Thr Ser Glu Gln Arg Gly
65                  70                  75                  80

Leu Lys Ser Thr Ile Asp Ser Gly Ala Thr Trp Asn Gly Gln Thr Met
                85                  90                  95

Ala Arg Thr Glu Leu Ile Pro Gln Thr Thr Ala Asn Leu Gly Ser Gly
            100                 105                 110

Asn Leu Phe Tyr His Phe Ser Val Lys Arg Ser Asn Thr Asn Ala Pro
        115                 120                 125

Asp Pro Thr Lys Glu His Gln Val Ala Phe Phe Glu Ser His Phe Thr
    130                 135                 140

Glu Leu Lys Tyr Gly Val Gly Ser Asn Pro Ser Asp Leu Gln Trp His
145                 150                 155                 160

Val Gly Gly Val Ser Lys Trp Ser Thr Pro Phe Thr Ala Asp Thr Trp
                165                 170                 175

Phe Asn Phe Ala Tyr Asp Ile Asp Phe Ser Lys Ser Thr Val Gly Leu
            180                 185                 190

Trp Ala Ser Thr Gly Ser Ser Pro Leu Val Lys Val Gln Asn Ile
        195                 200                 205

Ala Ala Ser Thr Ser Thr Asn Ser Ala Asp Trp His Leu Gly Val Leu
    210                 215                 220

Arg Val Ile Cys Ser Gly Val Val Glu Asp Trp Tyr Phe Ser Gly Val
225                 230                 235                 240

Tyr Val Glu Asn Gly Thr Ile Thr Thr Ala Ile Gly Ser Gly Leu Val
                245                 250                 255

His Tyr Arg Ser Thr Thr
            260

<210> SEQ ID NO 76
```

-continued

```
<211> LENGTH: 325
<212> TYPE: PRT
<213> ORGANISM: Coprionopsis cinerea

<400> SEQUENCE: 76
```

| | | | | | | | | | | | | | | | |
|---|---|---|---|---|---|---|---|---|---|---|---|---|---|---|---|
| Met | Leu | Gly | Leu | Pro | Trp | Val | Phe | Leu | Ser | Leu | Leu | Ala | Val | Ser | Ala |
| 1 | | | | 5 | | | | | 10 | | | | | 15 | |
| Asn | Ala | Gly | Arg | Ile | Val | Trp | Asp | Gly | Ser | Phe | Asn | Asn | Tyr | Thr | Thr |
| | | | 20 | | | | | 25 | | | | | 30 | | |
| Pro | Ala | Asp | Phe | Asp | Arg | Trp | Ser | Trp | Ala | Asn | Gln | Val | Gly | Thr | Tyr |
| | | 35 | | | | | 40 | | | | | 45 | | | |
| Gln | Trp | Tyr | Ile | Lys | Gly | Ser | Gly | Pro | Thr | Ser | Arg | Tyr | Leu | Asn | Leu |
| | 50 | | | | | 55 | | | | | 60 | | | | |
| Asp | Pro | Ser | Tyr | Lys | Asn | Pro | Ala | Ile | Thr | Ser | Glu | Leu | Arg | Gly | Leu |
| 65 | | | | | 70 | | | | | 75 | | | | | 80 |
| Lys | Val | Thr | Ile | Asp | Thr | Thr | Ala | Thr | Trp | Asn | Ser | Gln | Met | Met | Arg |
| | | | | 85 | | | | | 90 | | | | | 95 | |
| Thr | Glu | Leu | Ile | Pro | Gln | Thr | Asn | Ala | Asn | Leu | Gly | Gln | Gly | Asn | Leu |
| | | | | 100 | | | | | 105 | | | | | 110 | |
| Phe | Tyr | His | Phe | Ser | Ile | Lys | Arg | Thr | Asn | Thr | Asn | Ala | Pro | Asp | Pro |
| | | | 115 | | | | | 120 | | | | | 125 | | |
| Thr | Leu | Glu | His | Gln | Val | Met | Phe | Phe | Glu | Ser | His | Phe | Thr | Glu | Leu |
| | 130 | | | | | 135 | | | | | 140 | | | | |
| Lys | Tyr | Gly | Val | Gly | Ser | Asn | Pro | Ser | Asn | Leu | Gly | Trp | Tyr | Ala | Gly |
| 145 | | | | | 150 | | | | | 155 | | | | | 160 |
| Gly | Thr | Glu | Arg | Trp | Ser | Thr | Pro | Phe | Thr | Ala | Asp | Thr | Trp | Phe | Asn |
| | | | | 165 | | | | | 170 | | | | | 175 | |
| Phe | Ala | Tyr | Asp | Ile | Asp | Phe | Thr | Ala | Lys | Thr | Val | Gly | Leu | Trp | Ala |
| | | | 180 | | | | | 185 | | | | | 190 | | |
| Ser | Thr | Asn | Gly | Asn | Pro | Leu | Val | Lys | Val | Val | Gln | Asn | Val | Pro | Ala |
| | | 195 | | | | | 200 | | | | | 205 | | | |
| Asn | Thr | Phe | Thr | Asp | Ser | Arg | Asp | Phe | His | Val | Gly | Val | Leu | Arg | Ile |
| | 210 | | | | | 215 | | | | | 220 | | | | |
| Val | Asn | Arg | Asn | Pro | Pro | Glu | Asp | Trp | Tyr | Val | Ser | Gly | Val | Tyr | Ile |
| 225 | | | | | 230 | | | | | 235 | | | | | 240 |
| Glu | Glu | Gly | Pro | Ile | Thr | Thr | Gln | Ile | Gly | Asp | Gly | Ser | Ser | Pro | Gly |
| | | | | 245 | | | | | 250 | | | | | 255 | |
| Pro | Glu | Pro | Pro | Val | Val | Thr | Asn | Pro | Pro | Val | Thr | Thr | Pro | Pro |
| | | | 260 | | | | | 265 | | | | | 270 | | |
| Val | Val | Thr | Pro | Pro | Pro | Val | Thr | Thr | Thr | Pro | Ser | Gly | Pro |
| | | 275 | | | | | 280 | | | | | 285 | | | |
| Leu | Gln | Thr | Lys | Tyr | Gly | Gln | Cys | Gly | Gly | Asn | Gly | Tyr | Thr | Gly | Pro |
| | 290 | | | | | 295 | | | | | 300 | | | | |
| Thr | Asn | Cys | Val | Glu | Gly | Thr | Thr | Cys | Val | Ala | Val | Ser | Pro | Pro | Tyr |
| 305 | | | | | 310 | | | | | 315 | | | | | 320 |
| Tyr | Tyr | Gln | Cys | Gln | | | | | | | | | | | |
| | | | | 325 | | | | | | | | | | | |

```
<210> SEQ ID NO 77
<211> LENGTH: 341
<212> TYPE: PRT
<213> ORGANISM: Podospora anserina

<400> SEQUENCE: 77
```

| | | | | | | | | | | | | | | | |
|---|---|---|---|---|---|---|---|---|---|---|---|---|---|---|---|
| Met | Lys | Phe | His | Val | Leu | Ser | Gly | Leu | Val | Ala | Gln | Val | Leu | Ser | Val |
| 1 | | | | 5 | | | | | 10 | | | | | 15 | |

Ser Ala Gly Thr Ile Leu Trp Asp Gly Arg Phe Asn Asp Met Thr Ser
            20                  25                  30

Ser Ala Asp Leu Asn Lys Trp Ser Trp Gly Asn Gln Val Gly Pro Tyr
        35                  40                  45

Gln Tyr Tyr Ile His Gly Ser Ser Pro Val Ser Ala Tyr Val Asn Leu
    50                  55                  60

Ser Pro Asp Tyr Lys Asn Pro Ala Asp Thr Gly Ser Arg Gln Gly Ala
65                  70                  75                  80

Lys Ile Thr Leu Asp Asn Thr Ala Tyr Trp Asn Gly Gln Asn Met Arg
                85                  90                  95

Arg Thr Glu Leu Ile Pro Gln Thr Thr Ala Ala Ile Asn Gln Gly Lys
            100                 105                 110

Val Tyr Tyr His Phe Ser Leu Met Arg Lys Asp Ile Asn Ala Pro Ala
        115                 120                 125

Thr Thr Arg Glu His Gln Ile Ala Phe Phe Glu Ser His Phe Thr Glu
    130                 135                 140

Leu Lys Ser Gly Trp Leu Ser Gly Ala Pro Gly Ile Ser Asp Thr Leu
145                 150                 155                 160

Leu Arg Trp Cys Ile Asp Phe Ala Ala Gly Thr Val Gly Phe Trp His
                165                 170                 175

Ser Thr Gly Ser Asp Pro Leu Thr Arg Lys Val Ala Pro Val Lys Thr
            180                 185                 190

Ser Thr Ser Ser Asn Gly Ala Asp Trp His Val Gly Val Leu Glu Leu
        195                 200                 205

Pro Arg Ser Gly Tyr Pro Asp Ser Asn Glu Asp Phe Tyr Trp Ser Gly
    210                 215                 220

Val Tyr Ile Glu Ser Gly Ser Leu Thr Thr Ser Val Ala Gly Pro Gly
225                 230                 235                 240

Gln Pro Ile Pro Gly Asp Gly Ser Ser Ser Ser Ser Ser Ser Ser Ser
                245                 250                 255

Ser Val Pro Ser Ser Thr Ser Thr Arg Val Ser Ser Thr Ser Thr Pro
            260                 265                 270

Ala Pro Val Ser Ser Thr Thr Leu Val Thr Ser Thr Thr Arg Val Ser
        275                 280                 285

Ser Thr Ser Thr Ser Ser Ala Ala Pro Val Gln Thr Thr Pro Ser Gly
    290                 295                 300

Cys Thr Ala Gly Gln Tyr Ala Gln Cys Asp Gly Ile Gly Phe Ser Gly
305                 310                 315                 320

Cys Lys Thr Cys Ala Ala Pro Tyr Thr Cys Lys Tyr Gly Asn Asp Trp
                325                 330                 335

Tyr Ser Gln Cys Leu
            340

<210> SEQ ID NO 78
<211> LENGTH: 379
<212> TYPE: PRT
<213> ORGANISM: Aspergillus oryzae

<400> SEQUENCE: 78

Met Gln Ser Leu Ile Thr Leu Leu Ala Leu Pro Ala Ser Thr Leu Ala
1               5                   10                  15

Gly Ser Val Leu Trp Ser Gly Ile Ser Asp Ser Ser Leu Thr Val Asp
            20                  25                  30

Asp Ile Asp Lys Trp Ser Trp Ser Asn Gln Val Gly Ala Trp Gln Trp

```
                35                  40                  45
Tyr Ile His Gly Ser Gly Lys Thr Ser Glu Tyr Leu Gly Ile Ser Pro
 50                  55                  60

Glu Phe Lys Asn Pro Ala Ala Asp Ala Gln Gly Leu Arg Ile Thr
 65                  70                  75                  80

Ile Asp Gly Thr Ser Phe Trp Asn Gly Gln Thr Met Glu Arg Ser Glu
                 85                  90                  95

Leu Ile Pro Gln Thr Lys Ala Asp Leu Gly Ser Gly His Leu Tyr Tyr
                100                 105                 110

His Phe Ser Leu Ser Thr Lys Glu Thr Asn Ala Pro Asn Pro Ser Phe
            115                 120                 125

Glu His Gln Ile Ala Phe Phe Glu Ser His Phe Thr Glu Leu Lys Tyr
            130                 135                 140

Gly Ala Ser Gly Ser Ser Asp Asn Thr Leu Ser Trp Asn Ala Asp Gly
145                 150                 155                 160

Lys Ser His Trp Ser Val Gln Leu Glu Ala Gly Thr Trp Tyr Asn Phe
                165                 170                 175

Ala Tyr Asp Ile Asp Phe Asp Ser Lys Lys Val Gly Leu Trp Ala Ser
                180                 185                 190

Asn Gly Ser Glu Pro Leu Thr Gln Val Val Glu Pro Val Ser Ala Ser
            195                 200                 205

Thr Ser Thr Asn Ser Ala Asp Trp His Val Gly Gln Leu Arg Leu Pro
210                 215                 220

Gly Ser Glu Ser Asp Asp Ala Ala Glu Asp Trp Phe Trp Ser Gly Val
225                 230                 235                 240

Tyr Ile Glu Glu Gly Pro Ile Thr Thr Glu Ile Gly Ser Glu Ser Ser
                245                 250                 255

Ser Gly Ser Ser Ser Ala Gly Pro Ser Ser Thr Thr Ile Ala Thr
            260                 265                 270

Thr Ala Pro Ala Ser Ser Thr Ala His Ser Ala Thr Ser Thr Gly Gly
            275                 280                 285

Ile Thr Ala Thr Val Ser Ser Val Gly Leu Thr Thr Ala Thr Pro
290                 295                 300

Ser Pro Val Ser Thr Ala Val Ser Ser Val Thr Pro Ser Ser Leu
305                 310                 315                 320

Asn Ala Ala Pro Thr Lys Ser Thr Glu Val Ala Thr Pro Thr Ser Ser
                325                 330                 335

Ser Val Ala Thr Phe Ala Ser Pro Thr Ser Ala Ala Glu Phe Leu Thr
            340                 345                 350

Asp Ile Arg Ala Leu Leu Lys Thr Leu Leu Ser Arg Ser Glu Ala Gly
            355                 360                 365

Ser Val His Ala Arg Asp Phe Ile Arg Arg Gly
            370                 375

<210> SEQ ID NO 79
<211> LENGTH: 410
<212> TYPE: PRT
<213> ORGANISM: Aspergillus niger

<400> SEQUENCE: 79

Met Lys Gly Ala Ala Phe Leu Val Phe Pro Ala Ser Thr Leu Ala Gly
 1               5                  10                  15

Ser Val Leu Trp Ser Gly Ile Phe Asn Ser Ser Tyr Thr Val Ala Asp
                20                  25                  30
```

```
Phe Asp Glu Trp Ser Trp Ser Asn Gln Ile Ala Pro Trp Gln Trp Tyr
             35                  40                  45

Ile His Gly Asp Gly Lys Thr Ser Glu Tyr Leu Ala Leu Ser Ser Asp
 50                  55                  60

Tyr Lys Asn Pro Ala Ala Ser Asp Ala Gln Gly Leu Gln Thr Arg Leu
 65                  70                  75                  80

Val Leu Pro Pro Pro His Ala His Asn Thr Phe Ser His Ser Thr Asn
                 85                  90                  95

Thr Met Asn Glu Gln Asp Ser Thr Ser Phe Trp Glu Gly Gln Ser Met
            100                 105                 110

Gln Arg Thr Glu Leu Ile Pro Gln Met Ser Pro Ser Ser Ser Ala Ser
            115                 120                 125

Asp Leu Gly Ser Gly His Leu Tyr Tyr His Phe Ser Leu Ser Ala Ser
130                 135                 140

Ser Thr Asn Pro Pro Ser Ser Ser Glu His Gln Ile Ala Phe Phe
145                 150                 155                 160

Glu Ser His Phe Thr Glu Leu Gln Tyr Gln Asp Asn Thr Leu Lys Trp
                165                 170                 175

Asn Ala Gly Gly Asp Thr His Tyr Ser Val Glu Leu Glu Thr Gly Lys
            180                 185                 190

Trp Tyr Asn Phe Ala Tyr Asp Ile Asp Phe Asp Asn Gln Lys Val Gly
            195                 200                 205

Leu Trp Ala Ser Asn Gly Ser Asp Ala Leu Thr Glu Val Val Ser Pro
            210                 215                 220

Val Ser Ala Ser Ala Ser Ser Asn Gly Glu Asp Phe His Val Gly Val
225                 230                 235                 240

Leu Ser Leu Thr Gly Asp Gly Thr Glu Asp Trp Phe Trp Ser Gly Val
                245                 250                 255

Tyr Ile Glu Lys Gly Asp Leu Thr Lys Ser Ile Gly Asp Gly Ser Ser
            260                 265                 270

Ser Glu Ser Ser Ser Ser Gly Ser Ala Thr Thr Ala Gln Ala Val
            275                 280                 285

Glu Ser Thr Ser Ser Ala Ala Ala Ala Thr Ser Ala Ala Thr Thr
290                 295                 300

Ser Val Glu Ala Thr Thr Ala Ala Ala Thr Pro Thr Gln Asn Val
305                 310                 315                 320

Ala Val Ala Ser Ser Ser Thr Thr Ser Ala Ser Thr Thr Ser Ala Ala
                325                 330                 335

Thr Thr Ser Ser Glu Ser Thr Ala Ala Ala Thr Pro Ser Ala Ser Asn
            340                 345                 350

Pro Val Ile Ala Thr Pro Ser Ala Ala Pro Ser Ala Ala Pro Ser Ala
            355                 360                 365

Ala Ala Ala Ser Gly Ser Ala Ala Leu Pro Val Pro Thr Thr Ala Ser
            370                 375                 380

Gln Ile Leu Thr Asp Val Arg Ala Leu Leu Thr Ala Leu Leu Ala Arg
385                 390                 395                 400

Gln Gly Val His Ala Arg Asp Phe Ala Val
                405                 410

<210> SEQ ID NO 80
<211> LENGTH: 255
<212> TYPE: PRT
<213> ORGANISM: Emericella nidulans

<400> SEQUENCE: 80
```

-continued

```
Met Lys Ser Thr Ser Ile Leu Pro Leu Leu Ser Thr Leu Thr Pro Leu
1               5                   10                  15

Ala Ser Ala Ala Thr Val Trp Ser Gly Leu Phe Asn Glu Ser Tyr Thr
            20                  25                  30

Val Ala Asp Phe Asp Lys Trp Ser Trp Ser Ser Gln Ile Pro Pro Tyr
        35                  40                  45

Gln Trp Tyr Ile His Gly Ser Glu Glu Thr Ala His Tyr Leu Ser Leu
    50                  55                  60

Ser Ser Glu Tyr Lys Asn Pro Asn Ser Thr Leu Asp Glu Ala Gln Gly
65                  70                  75                  80

Leu Lys Thr Thr Leu Asp Asn Thr Ala Ser Trp Asn Gly Gln Thr Met
                85                  90                  95

Met Arg Thr Glu Leu Ile Pro Gln Val Glu Ser Gly Val Asp Ile Gly
            100                 105                 110

Ser Gly Lys Lys Tyr Tyr His Phe Ser Leu Ser Val Asp Glu Asp Gly
        115                 120                 125

Leu Pro Asn Val Glu Leu Glu His Gln Ile Ala Phe Phe Glu Ser His
    130                 135                 140

Phe Thr Glu Leu Lys Tyr Gly Gly Ser Ser Asp Thr Ala Ser Ser Leu
145                 150                 155                 160

Thr Phe Tyr Ala Asn Ser Ala Ala Gln Trp Ser Thr Ala Leu Glu Ala
                165                 170                 175

Gly Val Trp Tyr Asn Phe Ala Tyr Gly Ile Asp Phe Asp Gly Gly Ser
            180                 185                 190

Val Glu Leu Tyr Thr Ser Thr Gly Ala Asp Asp Leu Glu Leu Ala Val
        195                 200                 205

Gln Ala Val Ser Ala Ser Ala Ser Asn Ser Gln Asp Trp His Val
    210                 215                 220

Gly Val Leu Arg Leu Asp Asn Gly Val Asp Gly Gly Glu Ser Trp
225                 230                 235                 240

Tyr Trp Ser Gly Val Tyr Val Glu Asp Gly Glu Val Thr Leu Ala
                245                 250                 255
```

<210> SEQ ID NO 81
<211> LENGTH: 445
<212> TYPE: PRT
<213> ORGANISM: Podospora anserina

<400> SEQUENCE: 81

```
Met Ala Asp Arg Pro Ser Arg Gly Glu Arg Ser Arg Val Val Ser Arg
1               5                   10                  15

Gln Gly Ala Ser Arg Ile Ser His Phe Ile Glu Leu Gly Ile Pro Asn
            20                  25                  30

Leu Thr Ile Lys Met His Ser Arg Asn Val Leu Ala Ala Val Ala
        35                  40                  45

Leu Ala Gly Ala Pro Ser Val His Ala Val Leu Arg Phe Ser Cys Ser
    50                  55                  60

Glu Leu Val Thr Glu Arg Leu Asp Pro Leu Val Phe Pro Gly Ala Met
65                  70                  75                  80

Gln Ser Pro His Val His Gln Ile Val Gly Gly Asn Met Phe Asn Val
                85                  90                  95

Thr Met Asp Pro Asn Arg His Asn Ile Gly Glu Glu Ala Thr Cys Thr
            100                 105                 110

Thr Cys Thr Phe Ser Glu Asp Phe Ser Asn Tyr Trp Thr Ala Ile Leu
```

```
                115                 120                 125
Tyr Phe Arg Ala Arg Asn Gly Thr Leu Ile Arg Val Pro Gln Arg Pro
130                 135                 140

Asn Ile Asp Phe Asp Gly Ala Arg Gly Gly Gly Met Thr Val Tyr Tyr
145                 150                 155                 160

Thr Ala Thr Tyr Gln Asn His Lys Pro Thr Ala Phe Gln Pro Gly Phe
                165                 170                 175

Arg Met Ile Val Gly Asn Pro Met Tyr Arg Thr Gln Ala Glu Ala Ser
            180                 185                 190

Arg Tyr Arg Gln Met Thr Phe Thr Cys Leu Glu Thr Leu Ser Thr Arg
            195                 200                 205

Thr Gly Glu Thr Thr Glu Met Pro Lys Gln Pro Cys Arg Glu Gly Ile
210                 215                 220

Met Ser Asn Val Arg Phe Pro Thr Cys Trp Asp Gly Lys Thr Leu Asp
225                 230                 235                 240

Pro Pro Asp His Ser Ser His Val Ala Tyr Pro Ser Ser Gly Thr Phe
                245                 250                 255

Glu Ser Gly Gly Pro Cys Pro Ala Ser His Pro Val Arg Ile Pro Gln
            260                 265                 270

Leu Phe Tyr Glu Val Leu Trp Asp Thr Arg Arg Phe Asn Asp Arg Ser
            275                 280                 285

Leu Trp Pro Glu Asp Gly Ser Gln Pro Phe Val Trp Ser Tyr Gly Asp
290                 295                 300

Tyr Thr Gly Tyr Gly Thr His Gly Asp Tyr Val Phe Gly Trp Lys Gly
305                 310                 315                 320

Asp Ser Leu Gln Arg Ala Met Asp Ala Asn Cys Asp Phe Tyr Cys Pro
                325                 330                 335

Gln Leu Lys Thr Gln Ser Ile Ala Thr Gly Asn Gln Cys Arg Gln Asn
            340                 345                 350

Gln Lys Val Ala Glu Asn Ile Asp Gly Pro Phe Asp Arg Leu Pro Gly
            355                 360                 365

Asn Val Glu Ile Thr Gly Pro Gln Pro Gly Ala Ser Asn Pro Asn Pro
370                 375                 380

Gly Asn Gly Gly Gly Ser Thr Gln Thr Pro Val Gln Pro Thr Pro Val
385                 390                 395                 400

Pro Asn Pro Gly Asn Gly Gly Cys Ser Val Gln Lys Trp Gly Gln
                405                 410                 415

Cys Gly Gly Gln Gly Trp Ser Gly Cys Thr Val Cys Ala Ser Gly Ser
            420                 425                 430

Thr Cys Arg Ala Gln Asn Gln Trp Tyr Ser Gln Cys Leu
            435                 440                 445

<210> SEQ ID NO 82
<211> LENGTH: 190
<212> TYPE: PRT
<213> ORGANISM: Artificial
<220> FEATURE:
<223> OTHER INFORMATION: synthetically constructed consensus
      hemicellulase enzyme
<220> FEATURE:
<221> NAME/KEY: VARIANT
<222> LOCATION: (1)..(1)
<223> OTHER INFORMATION: May be S or Y
<220> FEATURE:
<221> NAME/KEY: misc_feature
<222> LOCATION: (2)..(3)
<223> OTHER INFORMATION: Xaa can be any naturally occurring amino acid
<220> FEATURE:
```

```
<221> NAME/KEY: VARIANT
<222> LOCATION: (5)..(5)
<223> OTHER INFORMATION: May be I, F or L
<220> FEATURE:
<221> NAME/KEY: VARIANT
<222> LOCATION: (6)..(6)
<223> OTHER INFORMATION: May be D or N
<220> FEATURE:
<221> NAME/KEY: VARIANT
<222> LOCATION: (11)..(11)
<223> OTHER INFORMATION: May be S, A or G
<220> FEATURE:
<221> NAME/KEY: VARIANT
<222> LOCATION: (14)..(14)
<223> OTHER INFORMATION: May be V or I
<220> FEATURE:
<221> NAME/KEY: VARIANT
<222> LOCATION: (15)..(15)
<223> OTHER INFORMATION: May be P or G
<220> FEATURE:
<221> NAME/KEY: VARIANT
<222> LOCATION: (16)..(16)
<223> OTHER INFORMATION: May be S or P
<220> FEATURE:
<221> NAME/KEY: VARIANT
<222> LOCATION: (17)..(17)
<223> OTHER INFORMATION: May be W or Y
<220> FEATURE:
<221> NAME/KEY: VARIANT
<222> LOCATION: (19)..(19)
<223> OTHER INFORMATION: May be W or Y
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: VARIANT
<222> LOCATION: (27)..(27)
<223> OTHER INFORMATION: May be T or V
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: VARIANT
<222> LOCATION: (33)..(33)
<223> OTHER INFORMATION: May be L, V or I
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (41)..(45)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: VARIANT
<222> LOCATION: (49)..(49)
<223> OTHER INFORMATION: May be R or K
<220> FEATURE:
<221> NAME/KEY: VARIANT
<222> LOCATION: (52)..(52)
<223> OTHER INFORMATION: May be I or L
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: VARIANT
<222> LOCATION: (55)..(55)
<223> OTHER INFORMATION: May be T or S
```

```
<220> FEATURE:
<221> NAME/KEY: VARIANT
<222> LOCATION: (56)..(56)
<223> OTHER INFORMATION: May be S or A
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: VARIANT
<222> LOCATION: (62)..(62)
<223> OTHER INFORMATION: May be T or N
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: VARIANT
<222> LOCATION: (66)..(66)
<223> OTHER INFORMATION: May be S or T or I
<220> FEATURE:
<221> NAME/KEY: misc_feature
<222> LOCATION: (73)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: VARIANT
<222> LOCATION: (81)..(81)
<223> OTHER INFORMATION: May be L, V or K
<220> FEATURE:
<221> NAME/KEY: VARIANT
<222> LOCATION: (82)..(82)
<223> OTHER INFORMATION: May be Y or F
<220> FEATURE:
<221> NAME/KEY: VARIANT
<222> LOCATION: (87)..(87)
<223> OTHER INFORMATION: May be L, V or I
<220> FEATURE:
<221> NAME/KEY: misc_feature
<222> LOCATION: (88)..(92)
<223> OTHER INFORMATION: Xaa can be any naturally occurring amino acid
<220> FEATURE:
<221> NAME/KEY: misc_feature
<222> LOCATION: (96)..(99)
<223> OTHER INFORMATION: Xaa can be any naturally occurring amino acid
<220> FEATURE:
<221> NAME/KEY: VARIANT
<222> LOCATION: (103)..(103)
<223> OTHER INFORMATION: May be L, V or I
<220> FEATURE:
<221> NAME/KEY: VARIANT
<222> LOCATION: (104)..(104)
<223> OTHER INFORMATION: May be C or A
<220> FEATURE:
<221> NAME/KEY: VARIANT
<222> LOCATION: (113)..(113)
<223> OTHER INFORMATION: May be M or L
<220> FEATURE:
<221> NAME/KEY: VARIANT
<222> LOCATION: (115)..(115)
<223> OTHER INFORMATION: May be S, T or Y
<220> FEATURE:
<221> NAME/KEY: misc_feature
<222> LOCATION: (119)..(124)
<223> OTHER INFORMATION: Xaa can be any naturally occurring amino acid
<220> FEATURE:
<221> NAME/KEY: VARIANT
<222> LOCATION: (125)..(125)
<223> OTHER INFORMATION: May be F or L
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: VARIANT
<222> LOCATION: (130)..(130)
```

```
<223> OTHER INFORMATION: May be S, D or A
<220> FEATURE:
<221> NAME/KEY: misc_feature
<222> LOCATION: (131)..(133)
<223> OTHER INFORMATION: Xaa can be any naturally occurring amino acid
<220> FEATURE:
<221> NAME/KEY: VARIANT
<222> LOCATION: (135)..(135)
<223> OTHER INFORMATION: May be L or F
<220> FEATURE:
<221> NAME/KEY: VARIANT
<222> LOCATION: (136)..(136)
<223> OTHER INFORMATION: May be W, Y or F
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: VARIANT
<222> LOCATION: (139)..(139)
<223> OTHER INFORMATION: May be N, T or E
<220> FEATURE:
<221> NAME/KEY: misc_feature
<222> LOCATION: (141)..(142)
<223> OTHER INFORMATION: Xaa can be any naturally occurring amino acid
<220> FEATURE:
<221> NAME/KEY: VARIANT
<222> LOCATION: (144)..(144)
<223> OTHER INFORMATION: May be P or A
<220> FEATURE:
<221> NAME/KEY: misc_feature
<222> LOCATION: (146)..(147)
<223> OTHER INFORMATION: Xaa can be any naturally occurring amino acid
<220> FEATURE:
<221> NAME/KEY: VARIANT
<222> LOCATION: (148)..(148)
<223> OTHER INFORMATION: May be V or A
<220> FEATURE:
<221> NAME/KEY: VARIANT
<222> LOCATION: (149)..(149)
<223> OTHER INFORMATION: May be V or A
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: VARIANT
<222> LOCATION: (151)..(151)
<223> OTHER INFORMATION: May be A, N P
<220> FEATURE:
<221> NAME/KEY: misc_feature
<222> LOCATION: (152)..(154)
<223> OTHER INFORMATION: Xaa can be any naturally occurring amino acid
<220> FEATURE:
<221> NAME/KEY: VARIANT
<222> LOCATION: (155)..(155)
<223> OTHER INFORMATION: May be N, S A
<220> FEATURE:
<221> NAME/KEY: VARIANT
<222> LOCATION: (156)..(156)
<223> OTHER INFORMATION: May be T or A
<220> FEATURE:
<221> NAME/KEY: VARIANT
<222> LOCATION: (157)..(157)
<223> OTHER INFORMATION: May be F, S or A
<220> FEATURE:
<221> NAME/KEY: VARIANT
<222> LOCATION: (158)..(158)
<223> OTHER INFORMATION: May be T or S
<220> FEATURE:
<221> NAME/KEY: VARIANT
<222> LOCATION: (159)..(159)
<223> OTHER INFORMATION: May be N or D
<220> FEATURE:
<221> NAME/KEY: VARIANT
<222> LOCATION: (160)..(160)
<223> OTHER INFORMATION: May be S or G
<220> FEATURE:
<221> NAME/KEY: VARIANT
```

```
<222> LOCATION: (161)..(161)
<223> OTHER INFORMATION: May be Q or A
<220> FEATURE:
<221> NAME/KEY: VARIANT
<222> LOCATION: (163)..(163)
<223> OTHER INFORMATION: May be W or F
<220> FEATURE:
<221> NAME/KEY: VARIANT
<222> LOCATION: (165)..(165)
<223> OTHER INFORMATION: May be I, L, V or F
<220> FEATURE:
<221> NAME/KEY: VARIANT
<222> LOCATION: (167)..(167)
<223> OTHER INFORMATION: May be I, Q, V or E
<220> FEATURE:
<221> NAME/KEY: VARIANT
<222> LOCATION: (169)..(169)
<223> OTHER INFORMATION: May be R, K or E
<220> FEATURE:
<221> NAME/KEY: VARIANT
<222> LOCATION: (170)..(170)
<223> OTHER INFORMATION: May be L, V or I
<220> FEATURE:
<221> NAME/KEY: misc_feature
<222> LOCATION: (172)..(179)
<223> OTHER INFORMATION: Xaa can be any naturally occurring amino acid
<220> FEATURE:
<221> NAME/KEY: VARIANT
<222> LOCATION: (182)..(182)
<223> OTHER INFORMATION: May be W, Y or F
<220> FEATURE:
<221> NAME/KEY: VARIANT
<222> LOCATION: (183)..(183)
<223> OTHER INFORMATION: May be Y or F
<220> FEATURE:
<221> NAME/KEY: VARIANT
<222> LOCATION: (184)..(184)
<223> OTHER INFORMATION: May be W or F
<220> FEATURE:
<221> NAME/KEY: VARIANT
<222> LOCATION: (187)..(187)
<223> OTHER INFORMATION: May be V or I
<220> FEATURE:
<221> NAME/KEY: VARIANT
<222> LOCATION: (188)..(188)
<223> OTHER INFORMATION: May be Y or F
<220> FEATURE:
<221> NAME/KEY: VARIANT
<222> LOCATION: (189)..(189)
<223> OTHER INFORMATION: May be V or I

<400> SEQUENCE: 82

Xaa Xaa Xaa Asp Xaa Xaa Lys Trp Ser Trp Xaa Asn Gln Xaa Xaa Xaa
 1               5                  10                  15

Xaa Gln Xaa Tyr Ile His Gly Ser Xaa Xaa Xaa Xaa Tyr Ile Xaa
            20                  25                  30

Xaa Ser Xaa Xaa Phe Lys Asn Pro Xaa Xaa Xaa Xaa Gln Gly Xaa
        35                  40                  45

Xaa Ile Thr Xaa Asp Xaa Xaa Xaa Trp Asn Gly Gln Xaa Met Xaa
    50                  55                  60

Arg Xaa Glu Leu Ile Pro Gln Thr Xaa Xaa Xaa Xaa Xaa Gly Xaa
65                  70                  75                  80

Xaa Xaa Tyr His Phe Ser Xaa Xaa Xaa Xaa Xaa Asn Ala Pro Xaa
                85                  90                  95

Xaa Xaa Xaa Glu His Gln Xaa Xaa Phe Phe Glu Ser His Phe Thr Glu
            100                 105                 110

Xaa Lys Xaa Gly Trp Gly Xaa Xaa Xaa Xaa Xaa Xaa Xaa Ile Asp
        115                 120                 125

Phe Xaa Xaa Xaa Xaa Val Xaa Xaa Ser Xaa Gly Xaa Xaa Ser Xaa
    130                 135                 140
```

```
Leu Xaa Xaa Xaa Xaa Xaa Xaa Xaa Xaa Xaa Xaa Xaa Xaa Xaa Xaa
145                 150                 155                 160

Xaa Asp Xaa His Xaa Gly Xaa Leu Xaa Xaa Pro Xaa Xaa Xaa Xaa
                165             170                 175

Xaa Xaa Xaa Glu Asp Xaa Xaa Xaa Ser Gly Xaa Xaa Xaa Glu
            180                 185                 190
```